(12) United States Patent
Tohyama et al.

(10) Patent No.: US 6,451,740 B2
(45) Date of Patent: Sep. 17, 2002

(54) URACIL COMPOUNDS AND USE THEREOF

(75) Inventors: Yoshitomo Tohyama, Ashiya; Yuzuru Sanemitsu, Kobe; Tomohiko Gotou, Minoo, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/729,312

(22) Filed: Dec. 5, 2000

(30) Foreign Application Priority Data

Dec. 7, 1999 (JP) ............................................ 11-348025
Jun. 2, 2000 (JP) ........................................ 2000-165751

(51) Int. Cl.[7] ........................ A01N 43/54; C07D 239/54
(52) U.S. Cl. ........................ 504/243; 544/312; 544/314
(58) Field of Search ................................ 544/312, 314; 504/243

(56) References Cited

U.S. PATENT DOCUMENTS

| | | | |
|---|---|---|---|
| 4,859,229 A | 8/1989 | Wenger et al. .................. | 71/92 |
| 5,981,436 A | 11/1999 | Drewes et al. .............. | 504/243 |
| 6,074,989 A | 6/2000 | Andree et al. .............. | 504/243 |

FOREIGN PATENT DOCUMENTS

| | | |
|---|---|---|
| DE | 198 53 864 A1 | 1/2000 |
| WO | WO 93/11669 | 6/1993 |
| WO | WO 97/01541 | 1/1997 |
| WO | WO 97/01542 | 1/1997 |
| WO | WO 97/05116 | 2/1997 |
| WO | WO 97/33875 | 9/1997 |
| WO | WO 97/33876 | 9/1997 |
| WO | WO 98/27067 | 6/1998 |
| WO | WO 98/27068 | 6/1998 |
| WO | WO 98/41093 | 9/1998 |
| WO | WO/ 02866 * | 1/2000 |
| WO | WO 00/02866 | 1/2000 |
| WO | WO 01/34575 A1 | 5/2001 |

* cited by examiner

*Primary Examiner*—Mark L Bergh
*Assistant Examiner*—Kahsay Habte
(74) *Attorney, Agent, or Firm*—Sughrue Mion, PLLC

(57) ABSTRACT

The present invention relates to an uracil compound of the formula [I]:

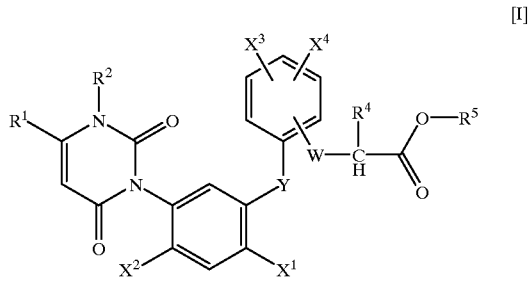

wherein W represents oxygen, sulfur, imino or $C_1$ to $C_3$ alkylimino; Y represents oxygen, sulfur, imino or $C_1$ to $C_3$ alkylimino; $R^1$ represents $C_1$ to $C_3$ alkyl or $C_1$ to $C_3$ haloalkyl; $R^2$ represents $C_1$ to $C_3$ alkyl; $R^4$ represents hydrogen or methyl; $R^5$ represents $C_1$ to $C_6$ alkyl, $C_1$ to $C_6$ haloalkyl, or the like; $X^1$ represents halogen, cyano or nitro; $X^2$ represents hydrogen or halogen; and each of $X^3$ and $X^4$ independently represents hydrogen, halogen, $C_1$ to $C_6$ alkyl, or the like. The present compound has an excellent herbicidal activity.

48 Claims, No Drawings

URACIL COMPOUNDS AND USE THEREOF

The present invention relates to uracil compounds and use thereof.

An object of the present invention is to provide compounds having excellent herbicidal activity.

Recently, a number of herbicides are commercially available and used. However, since there are many kinds of weeds to be controlled and generation thereof occurs over a long period of time, a herbicide is required having higher herbicidal effect, having wider herbicidal spectrum and causing no problem of phytotoxicity on crops.

U.S. Pat. No. 4,859,229 discloses that certain kinds of phenyluracil compounds have herbicidal activity, however, these phenyluracil compounds do not always have sufficient ability as a herbicide. Also WO 97/01541, and WO 98/41093 disclose that kinds of substituted phenoxyphenyl uracil compounds have herbicidal activity, however, the compounds do not always have sufficient ability as a herbicide.

The present inventors have intensively investigated to find compounds having excellent herbicidal activity, and resultantly, found that uracil compounds of the following formula [I] have excellent herbicidal activity, leading to completion of the present invention. Namely, the present invention provides uracil compounds [I] of the formula [I] (hereinafter, referred to as present compound):

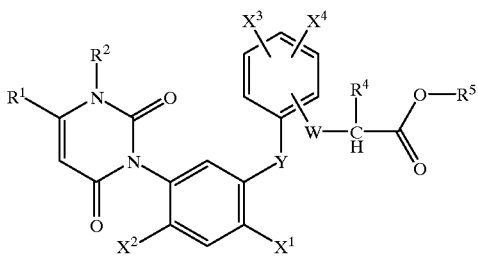

[I]

wherein, W represents oxygen, sulfur, imino or $C_1$ to $C_3$ alkylimino, Y represents oxygen, sulfur, imino or $C_1$ to $C_3$ alkylimino, $R^1$ represents $C_1$ to $C_3$ alkyl or $C_1$ to $C_3$ haloalkyl, $R^2$ represents $C_1$ to $C_3$ alkyl, $R^4$ represents hydrogen or methyl, $R^5$ represents hydrogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, or $C_3$ to $C_6$ haloalkynyl, $X^1$ represents halogen, cyano, or nitro, $X^2$ represents hydrogen or halogen, and each of $X^3$ and $X^4$ independently represents hydrogen, halogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, $C_3$ to $C_6$ haloalkynyl, $C_1$ to $C_6$ alkoxy $C_1$ to $C_6$ alkyl, $C_1$ to $C_6$ alkoxy, $C_1$ to $C_6$ haloalkoxy, $C_1$ to $C_6$ alkoxycarbonyl $C_1$ to $C_6$ alkoxy or cyano,
and herbicides comprising each of these compounds as an effective component.

Further, the present invention also provides aniline compounds [XXXII] of the formula [XXXII]:

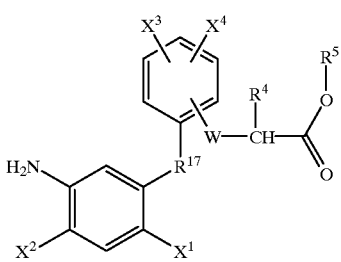

[XXXII]

wherein, W represents oxygen, sulfur, imino or $C_1$ to $C_3$ alkylimino, $R^{17}$ represents oxygen or sulfur, $R^4$ represents hydrogen or methyl, $R^5$ represents $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, $C_3$ to $C_6$ haloalkynyl, $X^1$ represents halogen, cyano, or nitro, $X^2$ represents hydrogen or halogen, and each of $X^3$ and $X^4$ independently represents hydrogen, halogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, $C_3$ to $C_6$ haloalkynyl, $C_1$ to $C_6$ alkoxy $C_1$ to $C_6$ alkyl, $C_1$ to $C_6$ alkoxy, $C_1$ to $C_6$ haloalkoxy, $C_1$ to $C_6$ alkoxycarbonyl $C_1$ to $C_6$ alkoxy or cyano, compounds [XXXIV] of the formula [XXXIV]:

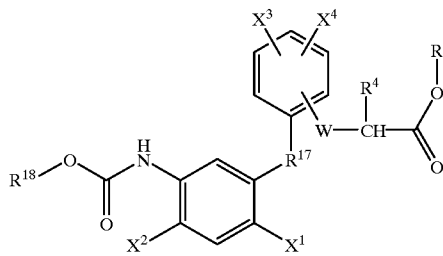

[XXXIV]

wherein, W represents oxygen, sulfur, imino or $C_1$ to $C_3$ alkylimino, $R^{17}$ represents oxygen or sulfur, $R^4$ represents hydrogen or methyl, $R^5$ represents $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, or $C_3$ to $C_6$ haloalkynyl, $R^{18}$ represents $C_1$ to $C_6$ alkyl or phenyl, $X^1$ represents halogen, cyano, or nitro, $X^2$ represents hydrogen or halogen, and each of $X^3$ and $X^4$ independently represents hydrogen, halogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, $C_3$ to $C_6$ haloalkinyl, $C_1$ to $C_6$ alkoxy $C_1$ to $C_6$ alkyl, $C_1$ to $C_6$ alkoxy group, $C_1$ to $C_6$ haloalkoxy, $C_1$ to $C_6$ alkoxycarbonyl $C_1$ to $C_6$ alkoxy or cyano group, and
compounds [XXXIII] of the formula [XXXIII]:

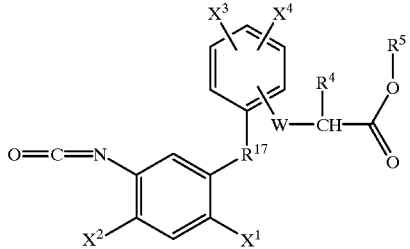

[XXXIII]

wherein, W represents oxygen, sulfur, imino or $C_1$ to $C_3$ alkylimino, $R^{17}$ represents oxygen or sulfur, $R^4$ represents hydrogen or methyl, $R^5$ represents $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, or $C_3$ to $C_6$ haloalkynyl, $X^1$ represents halogen, cyano, nitro, $X^2$ represents hydrogen or halogen, and each of $X^3$ and $X^4$ independently represents hydrogen, halogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl group, $C_3$ to $C_6$ haloalkynyl group, $C_1$ to $C_6$ alkoxy $C_1$ to $C_6$ alkyl, $C_1$ to $C_6$ alkoxy, $C_1$ to $C_6$ haloalkoxy, $C_1$ to $C_6$ alkoxycarbonyl $C_1$ to $C_6$ alkoxy or cyano,
which are useful as intermediates for producing the present compounds.

In the present invention, the $C_1$ to $C_3$ alkylimino represented by W includes methylimino, ethylimino and the like, the $C_1$ to $C_3$ alkylimino represented by Y includes methylimino, ethylimino and the like, the $C_1$ to $C_3$ alkyl represented by $R^1$ means methyl, ethyl, propyl, isopropyl, the $C_1$ to $C_3$ haloalkyl represented by $R^1$ includes bromomethyl, chloromethyl, fluoromethyl, dichloromethyl, trichloromethyl, difluoromethyl, trifluoromethyl, pentafluoroethyl, 1,1-difluoroethyl, 3,3,3-trifluoropropyl and the like, the $C_1$ to $C_3$ alkyl represented by $R^2$ means methyl, ethyl, propyl, isopropyl, the $C_1$ to $C_6$ alkyl represented by $R^5$ includes methyl, ethyl, propyl, isopropyl, butyl, s-butyl, t-butyl and the like, the $C_1$ to $C_6$ haloalkyl represented by $R^5$ includes bromomethyl, chloromethyl, fluoromethyl, dichloromethyl, trichloromethyl, difluoromethyl, chlorodifluoromethyl, bromodifluoromethyl, trifluoromethyl, pentafluoroethyl, 2-fluoroethyl, 1,1-difluoroethyl, 2,2,2-trichloroethyl, 3,3,3-trifluoropropyl, 3,3,3-trichloropropyl and the like, the $C_3$ to $C_6$ alkenyl represented by $R^5$ includes allyl, 1-methylallyl, 1,1-dimethylallyl, 2-methylallyl, 1-butenyl, 2-butenyl, 3-butenyl and the like, the $C_3$ to $C_6$ haloalkenyl represented by $R^5$ includes 1-chloroallyl, 1-bromoallyl, 2-chloroallyl, 3,3-dichloroallyl and the like, the $C_3$ to $C_6$ alkynyl represented by $R^5$ includes 2-propynyl, 1-methyl-2-propynyl, 1,1-dimethyl-2-propynyl, 2-butynyl, 3-butynyl, 1-methyl-2-butynyl and the like, the $C_3$ to $C_6$ haloalkynyl represented by $R^5$ includes 3-chloro-2-propynyl, 3-bromo-2-propynyl, 1-fluoro-2-propynyl, 1-chloro-2-propynyl, 1-bromo-2-propynyl, 1-chloro-2-butynyl and the like, the $C_1$ to $C_6$ alkyl represented by $R^{18}$ includes methyl, ethyl, propyl, isopropyl, butyl, s-butyl, t-butyl and the like, the halogen represented by $X^1$ means fluorine, chlorine, bromine, iodine, the halogen represented by $X^2$ means fluorine, chlorine, bromine, iodine, the halogen represented by $X^3$ and $X^4$ means fluorine, chlorine, bromine, iodine, the $C_1$ to $C_6$ alkyl represented by $X^3$ and $X^4$ includes methyl, ethyl, propyl, isopropyl, butyl, s-butyl, t-butyl and the like, the $C_1$ to $C_6$ haloalkyl represented by $X^3$ and $X^4$ includes bromomethyl, chloromethyl, fluoromethyl, dichloromethyl, trichloromethyl, difluoromethyl, chlorodifluoromethyl, bromodifluoromethyl, trifluoromethyl, pentafluoroethyl, 2-fluoroethyl, 1,1-difluoroethyl, 2,2,2-trichloroethyl, 3,3,3-trifluoropropyl, 3,3,3-trichloropropyl and the like, the $C_3$ to $C_6$ alkenyl represented by $X^3$ and $X^4$ includes allyl, 1-methylallyl, 1,1-dimethylallyl, 2-methylallyl, 1-butenyl, 2-butenyl, 3-butenyl and the like, the $C_3$ to $C_6$ haloalkenyl represented by $X^3$ and $X^4$ includes 1-chloroallyl, 1-bromoallyl, 2-chloroallyl, 3,3-dichloroallyl and the like, the $C_3$ to $C_6$ alkynyl represented by $X^3$ and $X^4$ includes 2-propynyl, 1-methyl-2-propynyl, 1,1-dimethyl-2-propynyl, 2-butynyl, 3-butynyl, 1-methyl-2-butynyl and the like, the $C_3$ to $C_6$ haloalkynyl represented by $X^3$ and $X^4$ includes 3-chloro-2-propynyl, 3-bromo-2-propynyl, 1-fluoro-2-propynyl, 1-chloro-2-propynyl, 1-bromo-2-propynyl, 1-chloro-2-butynyl and the like, the $C_1$ to $C_6$ alkoxy $C_1$ to $C_6$ alkyl represented by $X^3$ and $X^4$ includes methoxymethyl, 2-methoxyethyl, 1-methoxyethyl, 3-methoxypropyl, ethoxymethyl, 2-ethoxyethyl, 3-ethoxypropyl, isopropoxymethyl, 2-isopropoxyethyl and the like, the $C_1$ to $C_6$ alkoxy represented by $X^3$ and $X^4$ includes methoxy, ethoxy, propoxy, isopropoxy, butoxy, s-butoxy, t-butoxy and the like, the $C_1$ to $C_6$ haloalkoxy represented by $X^3$ and $X^4$ includes chloromethoxy, bromomethoxy, dichloromethoxy, trichloromethoxy, trifluoromethoxy, 2-fluoroethoxy, 2,2,2-trichloroethoxy and the like, the $C_1$ to $C_6$ alkoxycarbonyl $C_1$ to $C_6$ alkoxy represented by $X^3$ and $X^4$ includes methoxycarbonylmethoxy, ethoxycarbonylmethoxy group, 1-methoxycarbonylethoxy, 1-ethoxycarbonylethoxy, 2-methoxycarbonylethoxy, 2-ethoxycarbonylethoxy and the like.

In the present compounds, those are preferable wherein $R^1$ is methyl substituted with fluorine atom(s) such as trifluoromethyl, difluoromethyl and the like, or ethyl substituted with fluorine atom(s) such as pentafluoroethyl, 1,1-difluoroethyl and the like, more preferably trifluoromethyl, $R^2$ is methyl or ethyl, more preferably methyl, $R^5$ is $C_1$ to $C_3$ alkyl such as methyl, ethyl and propyl, more preferably methyl or ethyl, $X^1$ is halogen, more preferably chlorine, $X^2$ is halogen, more preferably fluorine, $X^3$ is hydrogen, $X^4$ is hydrogen, W is oxgen, and/or Y is oxgen, from the standpoint of herbicidal activity. The substitution position of W on the benzen ring is preferably ortho position of Y, at this situation, $R^4$ is preferably hydrogen or methyl, more preferably hydrogen.

As the specially prefered compounds, compound wherein $R^1$ is trifluoromethyl, $R^2$ is methyl, $R^4$ is hydrogen, $R^5$ is methyl, $X^1$ is chlorine, $X^2$ is fluorine, $X^3$ is hydrogen, $X^4$ is hydrogen, W is oxgen, Y is oxgen, and the substitution position of W on the benzen ring is ortho position of Y; and compound wherein $R^1$ is trifluoromethyl, $R^2$ is methyl, $R^4$ is hydrogen, $R^5$ is ethyl, $X^1$ is chlorine, $X^2$ is fluorine, $X^3$ is hydrogen, $X^4$ is hydrogen, W is oxgen, Y is oxgen, and the substitution position of W on the benzen ring is ortho position of Y are listed.

In the present compounds, geometrical isomers derived from a double bond, optical isomers derived from asymmetric carbon, and a diastereomer may sometimes present, and the present compound also includes isomers thereof and mixtures of them.

Then, methods for producing the present compounds will be illustrated.

The present compounds can be produced, for example, by the following production methods ((Production Method 1) to (Production Method 6)).

(Production Method 1)

The present compound can be produced by reacting a compound [III] of the formula [III]

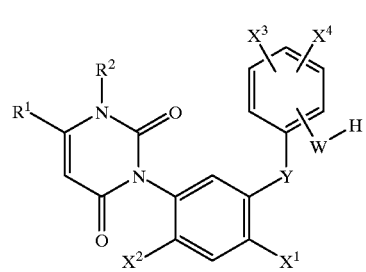

[III]

wherein, $R^1$, $R^2$, W, Y, $X^1$, $X^2$, $X^3$ and $X^4$ are the same as defined above, with a compound [IV] of the formula [IV]

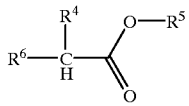

wherein, $R^4$ and $R^5$ are the same as defined above, $R^6$ represents a leaving group such as chlorine, bromine, iodine, methanesulfonyloxy, p-toluenesulfonyloxy and the like, in the presence of a base.

This reaction is conducted usually in a solvent, and the reaction temperature is usually from 0 to 200° C., preferably 20 to 100° C., and the reaction time is usually from an instant to 72 hours.

Regarding the amounts of reagents to be used in the reaction, it is theoretical that the amount of the compound [IV] is 1 mol and the amount of the base is 1 mol based on 1 mol of the compound [III], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, trilsopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

After completion of the reaction, the intended present compound can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the resulted present compound can also be purified by a procedure such as chromatography, re-crystallization and the like.
(Production Method 2)

Of the present compounds, the compound [I] wherein W is oxygen can be produced by reacting a compound [VI of the formula [V]

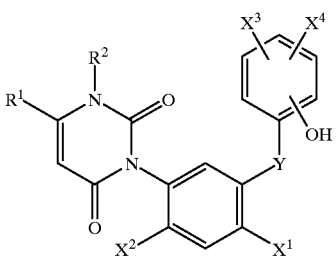

wherein, $R^1$, $R^2$, Y, $X^1$, $X^2$, $X^3$ and $X^4$ are the same as defined above,
with an alcohol compound [VI] of the formula [VI]

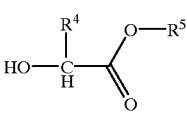

wherein, $R^4$, and $R^5$ are the same as defined above, in the presence of a dehydrating reagent.

This reaction is conducted usually in a solvent, and the reaction temperature is usually from −20 to 150° C., preferably from 0 to 100° C., and the reaction time is usually from an instant to 48 hours.

As the dehydrating reagent, there are listed combinations of triarylphosphines such as triphenylphosphine and the like or trialkylphosphines such as triethylphosphine and the like, and, di(lower alkyl)azodicarboxylates such as diethylazodicarboxylate, diisopropylazodicarboxylate and the like.

Regarding the amounts of reagents to be used in the reaction, the amount of the alcohol compound [VI] is 1 to 3 mol, preferably 1 to 1.5 mol, the amount of the triarylphosphine or trialkylphosphine is 1 to 3 mol, preferably 1 to 1.5 mol, and the amount of the di(lower alkyl)azodicarboxylate is 1 to 3 mol, preferably 1 to 1.2 mol, based on 1 mol of the compound [V]. The ratio of these reagents can be changed optionally depending on the reaction condition.

The solvent to be used in the reaction includes aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, dioxane, THF, ethylene glycol dimethyl ether, diglyme and the like; or mixtures thereof.

After completion of the reaction, the intended present compound can be obtained, for example, by the following operation 1) or 2).

1) A reaction solution is poured into water, this is extracted with an organic solvent, and the resulted organic layer is dried and concentrated, and the residue is subjected to chromatography.

2) A reaction solution is concentrated itself, and the residue is subjected to chromatography.

Further, the resulted present compound can also be purified by a procedure such as re-crystallization and the like.
(Production Method 3)

A compound of the present invention can be produced by using a carboxylic acid compound [VII] of the formula [VII]

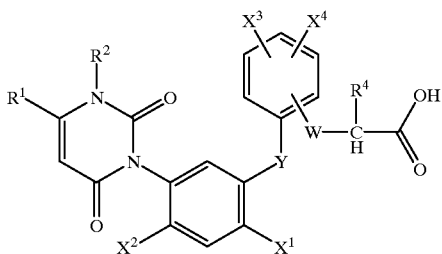

wherein, $R^1$, $R^2$, $R^4$, W, Y, $X^1$, $X^2$, $X^3$, and $X^4$ are the same as defined above,
and an alcohol compound [VIII] of the formula [VIII]

   [VIII]

wherein, $R^5$ is the same as defined above.

This reaction is conducted by, for example, reacting the carboxylic acid compound [VII] with a chlorinating agent to give an acid chloride (hereinafter, referred to as <Process 3-1>), then, reacting the acid chloride and the compound [VIII] in the presence of a base (hereinafter, referred to as <Process 3-2>).

<Process 3-1>

This reaction is conducted in the absence of a solvent or in a solvent, and the reaction temperature is usually from 0 to 150° C., and the reaction time is usually from an instant to 24 hours.

Regarding the amounts of reagents to be used in the reaction, it is theoretical that the amount of the chlorinating agent is 1 mol based on 1 mol of the carboxylic acid compound [VII], and the amounts thereof can be changed optionally depending on the reaction condition.

Examples of the chlorinating agent to be used include thionyl chloride, sulfuryl chloride, phosgene, oxalyl chloride, phosphorus trichloride, phosphorus pentachloride, phosphorus oxychloride and the like.

Examples of the solvent to be used include aliphatic hydrocarbons such as n-hexane, n-heptane, nonane, decane, ligroin, cyclohexane, petroleum ether and the like; aromatic hydrocarbons such as benzene, toluene, xylene, mesitylene and the like; aliphatic halogenated hydrocarbons such as methylene chloride, chloroform, carbon tetrachloride, 1,2-dichloroethane, 1,2,3-trichloropropane and the like; aromatic halogenated hydrocarbons such as chlorobenzene, dichlorobenzene, benzotrifluoride and the like; ethers such as diethyl ether, diisopropyl ether, methyl-t-butyl ether, 1,4-dioxane, tetrahydrofuran, ethylene glycol dimethyl ether, diglyme and the like; or mixtures thereof.

After completion of the reaction, for example, the reaction solution is concentrated, and the residue is used itself in <Process 3-2>.

<Process 3-2>

This reaction is conducted in the absence of a solvent or in a solvent, and the reaction temperature is usually from −20 to 100° C., and the reaction time is usually from an instant to 24 hours.

Regarding the amounts of reagents to be used in the reaction, it is theoretical that each amount of the alcohol compound [VIII] and the base is 1 mol based on 1 mol of the carboxylic acid compound [VII] used in <Process 3-1>, and the amounts thereof can be changed optionally depending on the reaction condition.

Examples of the base to be used include inorganic bases such as sodium hydrogen carbonate, potassium hydrogen carbonate, lithium carbonate, sodium carbonate, potassium carbonate and the like, nitrogen-containing aromatic compounds such as pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine, 5-ethyl-2-methylpyridine and the like, tertiary amines such as triethylamine, diisopropylethylamine, tri-n-propylamine, tri-n-butylamine, benzyldimethylamine, phenetyldimethylamine, N-methylmorpholine, 1,8-diazabicyclo[5.4.0]undec-7-ene, 1,5-diazabicyclo[4.3.0]non-5-ene, 1,4-diazabicyclo[2.2.2]octane and the like.

Examples of the solvent to be used include aliphatic hydrocarbons such as n-hexane, n-heptane, nonane, decane, ligroin, cyclohexane, petroleum ether and the like; aromatic hydrocarbons such as benzene, toluene, xylene, mesitylene and the like; aliphatic halogenated hydrocarbons such as methylene chloride, chloroform, carbon tetrachloride, 1,2-dichloroethane, 1,2,3-trichloropropane and the like; aromatic halogenated hydrocarbons such as chlorobenzene, dichlorobenzene, benzotrifluoride and the like; ethers such as diethyl ether, diisopropyl ether, methyl-t-butyl ether, 1,4-dioxane, tetrahydrofuran, ethylene glycol dimethyl ether, diglyme and the like; or mixtures thereof.

After completion of the reaction, the intended present compound can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the resulted present compound can also be purified by a procedure such as chromatography, re-crystallization and the like.

This reaction is not limited to the above-mentioned methods, and can also be conducted by a method in which a reaction is conducted in the presence of a condensing agent such as 1,1'-carbonyldiimidazole, 1,3-dicyclohexylcarbodiimide and the like, a method in which a reaction is conducted in the presence of an acid catalyst, and other known methods.

(Production Method 4)

Of the present compounds, the compound [I] wherein $X^1$ is nitro or cyano can be produced by reacting an uracil compound [IX] of the formula [IX]

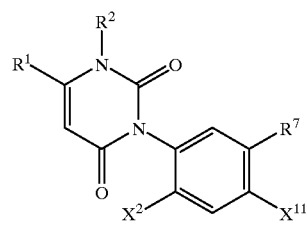   [IX]

wherein, $R^1$, $R^2$ and $X^2$ are the same as defined above, $R^7$ represents fluorine, chlorine, bromine or iodine, and $X^{11}$ represents nitro or cyano, with a compound [X] of the formula [X]

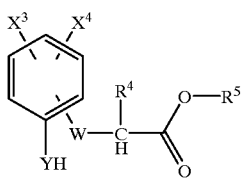

[X]

wherein, $R^4$, $R^5$, W, Y, $X^3$, and $X^4$ are the same as defined above.] in the presence of a base.

This reaction is conducted usually in the absence of a solvent or in a solvent, and the reaction temperature is from 0 to 200° C., and the reaction time is usually from an instant to 24 hours.

Regarding the amounts of reagents to be used in the reaction, it is theoretical that the amount of the compound [X] is 1 mol and the amount of the base is 1 mol based on 1 mol of the uracil compound [IX], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, sodium hydroxide, potassium hydroxide, calcium hydroxide, barium hydroxide and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

This reaction may sometimes be accelerated by using a catalyst. As the catalyst, copper iodide, copper bromide, copper chloride, copper powder and the like are listed, and the amount of the catalyst used in the reaction is from 0.0001 to 0.1 mol based on 1 mol of the uracil compound [IX], and the amounts thereof can be changed optionally depending on the reaction condition.

After completion of the reaction, the intended present compound can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the resulted present compound can also be purified by a procedure such as chromatography, re-crystallization and the like.

(Production Method 5)

Of the present compounds, the compound [I] wherein $X^1$ is fluorine, chlorine, bromine or iodine can be produced by the following scheme.

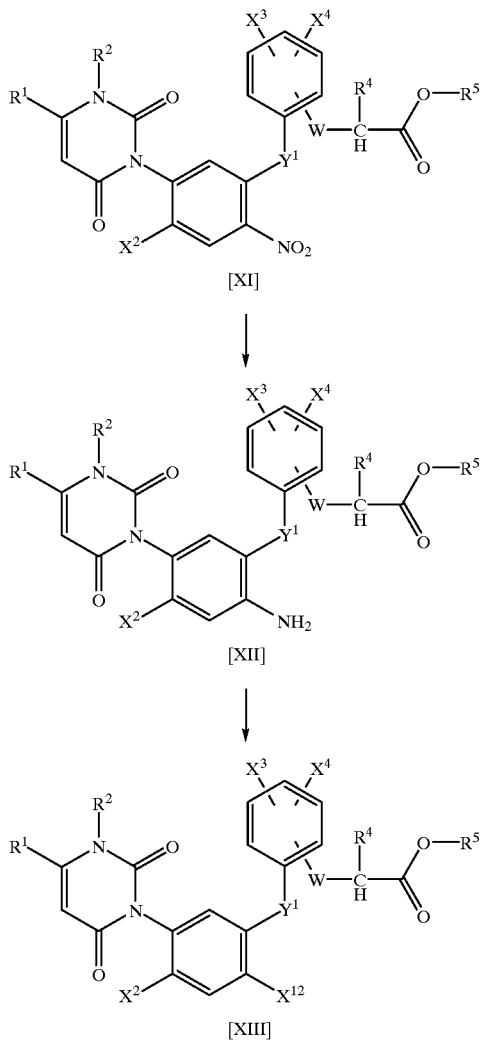

Wherein, $R^1$, $R^2$, $R^4$, $R^5$, W, $X^2$, $X^3$, and $X^4$ are the same as defined above, $X^{12}$ represents fluorine, chlorine, bromine or iodine, and $Y^1$ represents oxygen, sulfur, imino or alkylimino.

<Process 5-1>: A process for producing the compound [XII] from the compound [XI].

The compound [XII] can be produced, for example, by reducing the compound [XI] using an iron powder in the presence of an acid in a solvent.

This reaction is conducted usually in the absence of a solvent or in a solvent, and the reaction temperature is usually from 0 to 200° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [XI], and the amounts thereof can be changed optionally depending on the reaction condition.

As the acid to be used, acetic acid and the like are listed.

As the solvent to be used, there are listed, for example, water, acetic acid, ethyl acetate and the like or mixtures thereof.

After completion of the reaction, an intended material can be obtained by a usual post-treatment operation such as by filtrating, then, pouring a reaction solution into water and the deposited crystals are collected by filtration, or, extracting with an organic solvent, neutralization, concentration and the like.

The intended material can also be purified by a procedure such as chromatography, re-crystallization and the like.

<Process 5-2>: A process for producing the compound [XIII] from the compound [XII].

The compound [XIII] can be produced by i) diazotizing the compound [XII] in a solvent, then, ii) subsequently, reacting the diazo compound with potassium iodide, copper [I] bromide, copper [I] chloride or a mixture of hydrofluoric acid with boric acid (hereinafter, referred to as hydroborofluoric acid) depending on the intended compound, in a solvent.

In the diazotization reaction of the first step, the reaction temperature is usually from −20 to 20° C., and the reaction time is usually from an instant to 5 hours.

Regarding the amounts of reagents to be used in the reaction, it is theoretical that the amount of the diazotization agent is 1 mol based on 1 mol of the compound [XII], and the amounts thereof can be changed optionally depending on the reaction condition.

As the diazotization agent to be used, nitrites such as sodium nitrite, potassium nitrite, isoamyl nitrite, t-butyl nitrite and the like, are listed.

As the solvent to be used, there are listed, for example, acetonitrile, hydrobromic acid, hydrochloric acid, sulfuric acid, water and the like or mixtures thereof.

The reaction solution after completion of the reaction is used as it is in the following reaction.

In the reaction of the second step, the reaction temperature is from 0 to 80° C., and the reaction time is usually from an instant to 24 hours.

Regarding the amounts of reagents to be used in the reaction, each amount of potassium iodide, copper [I] bromide, copper [I] chloride or hydroborofluoric acid is from 1 to 3 mol based on 1 mol of the compound [XII], and the amounts thereof can be changed optionally depending on the reaction condition.

When copper [I] bromide is used, the reaction can also be conducted in the presence of copper [II] bromide, and when copper [I] chloride is used, the reaction can also be conducted in the presence of copper [II] chloride.

As the solvent to be used, there are listed, for example, acetonitrile, diethyl ether, t-butyl methyl ether, hydrobromic acid, hydrochloric acid, sulfuric acid water and the like or mixtures thereof.

After completion of the reaction, an intended present compound can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the resulted present compound can also be purified by a procedure such as chromatography, re-crystallization and the like.

(see, Org. Syn. Coll. Vol. 2, 604 (1943), Vol. 1, 136 (1932))

Further, this reaction is not limited to the above-mentioned methods, and production can also be conducted by reacting the compound [XII] with a diazotizing agent in a solvent in the presence of potassium iodide, copper [I] bromide, copper [I] chloride or hydroborofluoric acid depending on the intended compound (see, Heterocycles., 38, 1581 (1994), and the like).

When copper [I] bromide is used, the reaction can also be conducted in the presence of copper [II] bromide, and when copper [I] chloride is used, the reaction can also be conducted in the presence of copper [II] chloride.

(Production Method 6)

The present compound can be produced by reacting an uracil compound [XXXI] of the formula [XXXI]

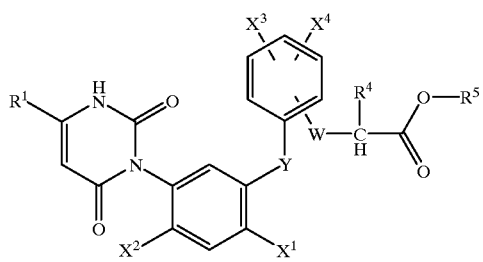

[XXXI]

wherein, $R^1$, $R^4$, $R^5$, W, Y, $X^1$, $X^2$, $X^3$, and $X^4$ are the same as defined above, with a compound [XXXX] of the formula [XXXX]

$$R^{18}-R^2 \quad [XXXX]$$

wherein, $R^{18}$ represents a leaving group such as chlorine, bromine, iodine, methanesulfonyloxy, p-toluenesulfonyloxy and the like and $R^2$ is the same as defined above, in the presence of a base.

This reaction is conducted usually in the absence of a solvent or in a solvent, and the reaction temperature is usually from 0 to 200° C., preferable 20 to 10° C., and the reaction time is usually from an instant to 24 hours.

Regarding the amounts of reagents to be used in the reaction, it is theoretical that the amount of the compound [XXXX] is 1 mol and the amount of the base is 1 mol based on 1 mol of the uracil compound [XXXI], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, metal alkoxides such as sodium methoxide, sodium ethoxide, potassium t-butoxide and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, sodium hydroxide, potassium hydroxide, calcium hydroxide, barium hydroxide and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; alcohols such as methanol, ethanol, ethylene glycol, isopropanol, t-butanol and the like; or mixtures thereof.

After completion of the reaction, an intended present compound can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the resulted present compound can also be purified by a procedure such as chromatography, re-crystallization and the like.

The compound [IV], the alcohol compound [VI], the alcohol compound [VIII] and the compound [X] used in the methods for producing the present compound can be produced by known methods, or, commercially available materials are used.

The carboxylic acid compound [VII] can be produced by acid hydrolysis of the present compound [I].

Some of intermediates used in the method for producing the present compound can be produced, for example, by the following production methods ((Intermediate Production Method 1) to (Intermediate Production Method 16)).

(Intermediate Production Method 1)

Of compound [III], the compound wherein W and Y are oxygen or sulfur (i.e. compound [XIX]) and the compound [XIV] can also be produced by a method described in the following scheme.

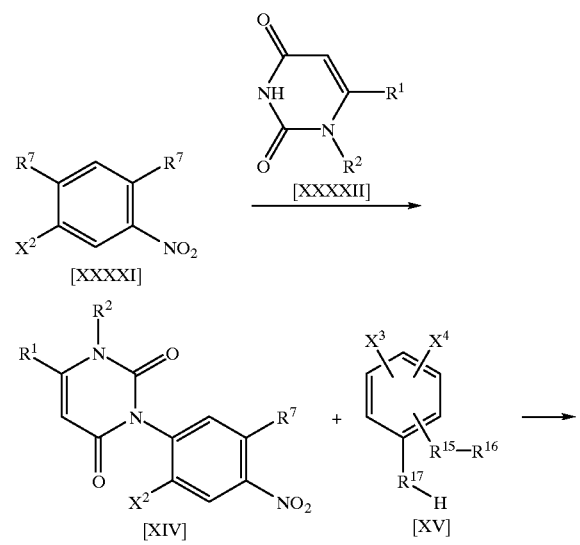

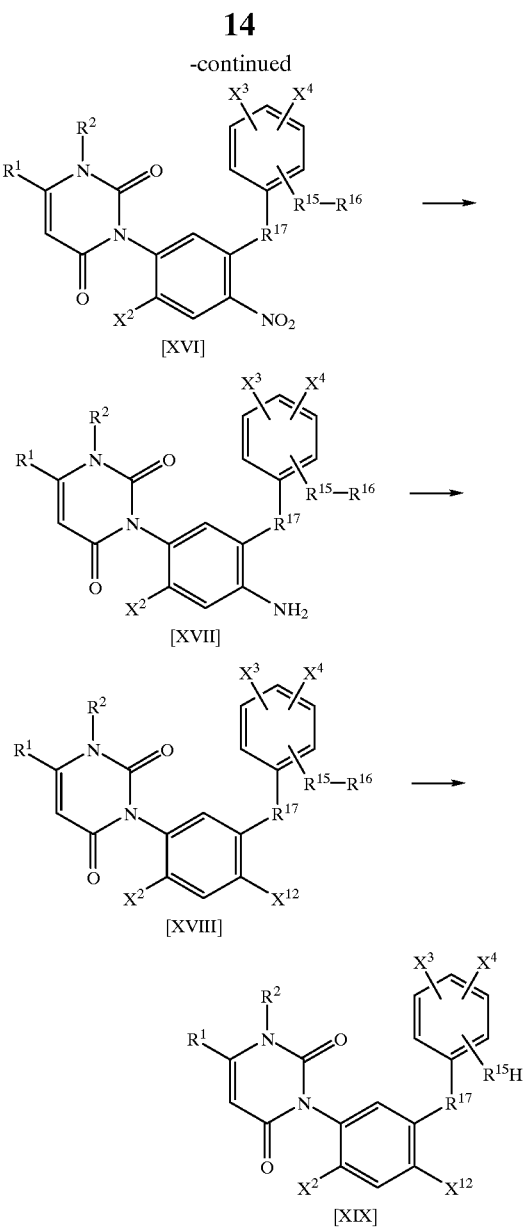

Wherein $R^1$, $R^2$, $R^7$, $X^2$, $X^3$, $X^4$ and $X^{12}$ are the same as defined above, each of $R^5$ and $R^7$ independently represents oxygen or sulfur, and $R^{16}$ represents a protective group such as silyl group such as t-butyldimethylsilyl and the like; $C_1$ to $C_6$ alkyl which may be substituted such as t-butyl, methyl and the like; benzyl which may be substituted such as benzyl and the like; methoxymethyl, acetyl, methoxycarbonyl, ethoxycarbonyl and the like.

<Process A1-1>: A process for producing the compound [XIV] from the compound [XXXXI]

The compound [XIV] can be produced by reacting the compound [XXXXI] with the compound [XXXXII] in the presence of a base.

This reaction is conducted usually in the absence of a solvent or in a solvent, and the reaction temperature is usually from 0 to 200° C., and the reaction time is usually from an instant to 24 hours.

Regarding the amounts of reagents to be used in the reaction, it is theoretical that the amount of the compound [XXXXII] is 1 mol and the amount of the base is 1 mol based on 1 mol of the compound [XXXXI], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

After completion of the reaction, an intended material can be obtained, for example, by the following operation 1), 2) or 3).

1) A reaction solution is poured into water, this is extracted with an organic solvent, and the resulted organic layer is dried and concentrated.

2) The reaction mixture is poured into water and the deposited crystals are collected by filtration.

3) A reaction solution is concentrated itself, or, filtrated if necessary before the filtrate is concentrated.

Further, the intended material can also be purified by a procedure such as chromatography, re-crystallization and the like.

<Process A1-2>: A process for producing the compound [XVI] from the compound [XIV].

The compound [XVI] can be produced by reacting the compound [XIV] with the compound [XV] in the presence of a base.

This reaction is conducted usually in the absence of a solvent or in a solvent, and the reaction temperature is usually from −20 to 200° C., preferable −5 to 80° C., and the reaction time is usually from an instant to 24 hours.

Regarding the amounts of reagents to be used in the reaction, it is theoretical that the amount of the compound [XV] is 1 mol and the amount of the base is 1 mol based on 1 mol of the compound [XIV], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4 -diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

After completion of the reaction, an intended material can be obtained, for example, by the following operation 1) or 2).

1) A reaction solution is poured into water, this is extracted with an organic solvent, and the resulted organic layer is washed with hydrochloric acid, then brine, dried and concentrated.

2) A reaction solution is concentrated itself, or, filtrated if necessary before the filtrate is concentrated.

Further, the intended material can also be purified by a procedure such as chromatography, re-crystallization and the like.

<Process A1-3>: A process for producing the compound [XVII] from the compound [XVI].

The compound [XVII] can be produced, for example, by reducing the compound [XVI] using an iron powder in the presence of an acid in a solvent.

The reaction temperature is usually from 0 to 20° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [XVI], and the amounts thereof can be changed optionally depending on the reaction condition.

As the acid to be used, acetic acid and the like are listed.

As the solvent to be used, there are listed, for example, water, acetic acid, ethyl acetate and the like or mixtures thereof.

After completion of the reaction, and intended material can be obtained by usual post-treatment such as by filtrating, then, pouring a reaction solution into water and collecting the produced crystals by filtration, or, subjecting a reaction solution to extraction with an organic solvent, neutralization, concentration and the like.

The intended material can also be purified by a procedure such as chromatography, re-crystallization and the like.

<Process Al-4>: A process for producing the compound [XVIII] from the compound [XVII].

The compound [XVIII] can be produced by i) diazotizing the compound [XVII] in a solvent, then, ii) subsequently, reacting the diazo compound with potassium iodide, copper (I) bromide, copper (I) chloride or hydroborofluoric acid in a solvent.

In the diazotization reaction of the first step, the reaction temperature is usually from −20 to 20° C., and the reaction time is usually from an instant to 5 hours.

Regarding the amounts of reagents to be used in the reaction, it is theoretical that the amount of the diazotization agent is 1 mol based on 1 mol of a compound of the general formula [XVII], and the amounts thereof can be changed optionally depending on the reaction condition.

As the diazotization agent to be used, nitrites such as sodium nitrite, potassium nitrite, isoamyl nitrite, t-butyl nitrite and the like, are listed.

As the solvent to be used, there are listed, for example, acetonitrile, hydrobromic acid, hydrochloric acid, sulfuric acid, water and the like or mixtures thereof.

The reaction solution after completion of the reaction is used as it is in the following reaction.

In the reaction of the second step, the reaction temperature is from 0 to 80° C., and the reaction time is usually from an instant to 24 hours.

Regarding the amounts of reagents to be used in the reaction, each amount of potassium iodide, copper (I) bromide, copper (I) chloride or hydroborofluoric acid is from 1 to 3 mol based on 1 mol of the compound [XVII], and the amounts thereof can be changed optionally depending on the reaction condition. When copper [I] bromide is used, the reaction can also be conducted in the presence of copper (II) bromide, and when copper (I) chloride is used, the reaction can also be conducted in the presence of copper (II) chloride.

As the solvent to be used, there are listed, for example, acetonitrile, diethyl ether, t-butyl methyl ether, hydrobromic acid, hydrochloric acid, sulfuric acid, water and the like or mixtures thereof.

After completion of the reaction, an intended material can be obtained by a usual post-treatment such as by collecting the produced crystals by filtration (if necessary, by adding water), or, extracting with an organic solvent, concentration and the like.

The intended material can also be purified by a procedure such as chromatography, re-crystallization and the like.

Further, this reaction is not limited to the above-mentioned methods, also be conducted by reacting the compound [XVII] with a diazotizing agent in a solvent (for example, acetonitrile, diethyl ether, t-butyl methyl ether, hydrobromic acid, hydrochloric acid, sulfuric acid, water and the like or mixtures thereof) in the presence of potassium iodide, copper (I) bromide, copper (I) chloride or hydroborofluoric acid.

(see, Heterocycles., 38, 1581 (1994), and the like).

<Process A1-5>: A process for producing the compound [XIX] from the compound [XVIII].

The compound [XIX] can be produced by de-protecting the compound [XVIII] using boron tribromide, HBr/acetic acid, conc. hydrochloric acid, conc. sulfuric acid or the like according to a method described in Protective Groups in Organic Synthesis (published by A Wiley-Interscience publication).

Herein, in the case the compound [XVIII] wherein $R^{16}$ is a benzyl which may be substituted such as benzyl, the compound [XIX] can also be produced by hydrogenation of the compound [XVIII] in the presence of a catalyst.

This reaction is usually conducted in a solvent. The reaction temperature is usually from −20 to 150° C., preferably from 0 to 50° C. The reaction time is usually from an instant to 48 hours. This reaction can also be conducted under positive pressure, and the reaction is usually conducted under a pressure of 1 to 5 atm.

The amount of the catalyst used in this reaction is from 0.001 to 100% by weight based on the compound [XVIII].

As the catalyst to be used in the reaction, anhydrous palladium/carbon, water-containing palladium/carbon, platinum oxide and the like are listed.

The solvent includes carboxylic acids such as formic acid, acetic acid, propionic acid and the like, esters such as ethyl formate, ethyl acetate, butyl acetate, diethyl carbonate and the like; ethers such as 1,4-dioxane, tetrahydrofuran, ethylene glycol dimethyl ether and the like; alcohols such as methanol, ethanol, isopropanol, and the like; water, or mixtures thereof.

After completion of the reaction, an intended material can be obtained by a usual post-treatment operation such as by filtrating a reaction solution before concentrating the solution, or, pouring a reaction solution into water before filtrating the produced crystal, or, pouring a reaction solution into water and subjecting the resulted mixture to extraction with an organic solvent, concentration and the like.

The intended material can also be purified by a procedure such as chromatography, re-crystallization and the like.

(Intermediate Production Method 2)

Of compounds [III], the compound wherein W is NH (i.e. compound [XXIII]) can also be produced by a method described in the following scheme.

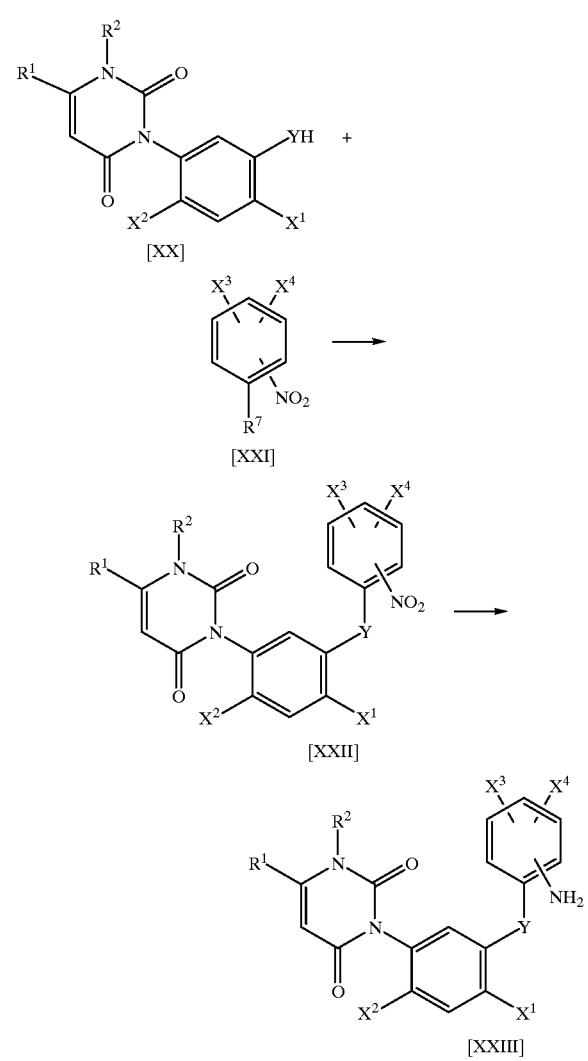

Wherein, $R^1$, $R^2$, $R^7$, Y, $X^1$, $X^2$, $X^3$ and $X^4$ are the same as defined above.

<Process A2-1>: A process for producing the compound [XXII] from the compound [XX]

The compound [XXII] can be produced by reacting the compound [XX] with the compound [XXI] in the presence of a base.

This reaction is conducted usually in the absence of a solvent or in a solvent, and the reaction temperature is usually from 0 to 200° C., and the reaction time is usually from an instant to 24 hours.

Regarding the amounts of reagents to be used in the reaction, it is theoretical that the amount of the compound [XXI] is 1 mol and the amount of the base is 1 mol based on 1 mol of the compound [XX], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

This reaction may sometimes be accelerated by adding a catalyst.

The amount of the catalyst used in the reaction is preferably from 0.0001 to 0.1 mol based on 1 mol of the compound [XX], and the amounts thereof can be changed optionally depending on the reaction condition.

As the catalyst, copper iodide, copper bromide, copper chloride, copper powder and the like are listed.

After completion of the reaction, an intended material can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the intended material can also be purified by a procedure such as chromatography, re-crystallization and the like.

<Process A2-2>: A process for producing the compound [XXIII] from the compound [XXII]

The compound [XXIII] can be produced, for example, by reducing the compound [XXII] using an iron powder in the presence of an acid in a solvent.

The reaction temperature is usually from 0 to 20° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [XXII], and the amounts thereof can be changed optionally depending on the reaction condition.

As the acid to be used, acetic acid and the like are listed.

As the solvent to be used, there are listed, for example, water, acetic acid, ethyl acetate and the like or mixtures thereof.

After completion of the reaction, an intended material can be obtained by a usual post-treatment such as by filtrating, then, collecting the produced crystals by filtration (if necessary, by adding water), or, extracting with an organic solvent, neutralization, concentration and the like.

The intended material can also be purified by a procedure such as chromatography, re-crystallization and the like.
(Intermediate Production Method 3)

Of compounds [III], the compound wherein W is oxygen (i.e. compound [V]) can be produced by a method described in the following scheme.

[XXIII]

[V]

Wherein, $R^1$, $R^2$, Y, $X^1$, $X^2$, $X^3$ and $X^4$ are the same as defined above.

The compound [V] can be produced by i) reacting the compound [XXIII] with diazotizing agent in a solvent, then, ii) subsequently, heating the product in an acidic solvent, or, allowing a copper salt to act on the product in the presence of a copper catalyst.

In the reaction of the first step, the reaction temperature is usually from −20 to 10° C., and the reaction time is usually from an instant to 5 hours.

Regarding the amounts of reagents to be used in the reaction, it is theoretical that the amount of the diazotization agent is 1 mol based on 1 mol of the compound [XXIII], and the amounts thereof can be changed optionally depending on the reaction condition.

As the diazotization agent to be used, nitrites such as sodium nitrite, potassium nitrite, isoamyl nitrite, t-butyl nitrite and the like, are listed.

As the solvent to be used, there are listed, for example, acetonitrile, hydrochloric acid, hydrobromic acid, sulfuric acid, water and the like or mixtures thereof.

The reaction solution after completion of the reaction is used as it is in the following reaction.

In the heating reaction in an acidic solvent of the second step, the reaction temperature is from 60° C. to reflux temperature, and the reaction time is usually from an instant to 48 hours.

As the acidic solvent there are listed, for example, hydrochloric acid, hydrobromic acid, sulfuric acid solution and the like or mixtures thereof.

After completion of the reaction, an intended material can be obtained by usual post-treatment such as by collecting the produced crystals by filtration (if necessary, by adding water), or, extracting with an organic solvent, concentration and the like.

The intended material can also be purified by a procedure such as chromatography, re-crystallization and the like.

The reaction for allowing a copper salt to act in the presence of a copper catalyst in the second step is conducted in a solvent. The reaction temperature is from 0° C. to reflux temperature, and the reaction time is from an instant to 24 hours.

Regarding the amounts of reagents to be used in the reaction, the amount of the copper catalyst is 0.001 to 5 mol and the amount of the copper salt is 1 to 100 mol based on 1 mol of the compound [XXIII], and the amounts thereof can be changed optionally depending on the reaction condition.

As the copper catalyst to be used, copper (I) oxide and the like are listed, and as the copper salt, copper (II) sulfate, copper (II) nitrate and the like are listed.

As the solvent, there are listed, for example, water, hydrochloric acid, sulfuric acid and the like or mixtures thereof.

After completion of the reaction, an intended material can be obtained by a usual post-treatment such as by extracting with an organic solvent, concentration and the like.

The intended material can also be purified by a procedure such as chromatography, re-crystallization and the like.

(Intermediate Production Method 4)

The compound [IX] can be produced by a method described in the following scheme.

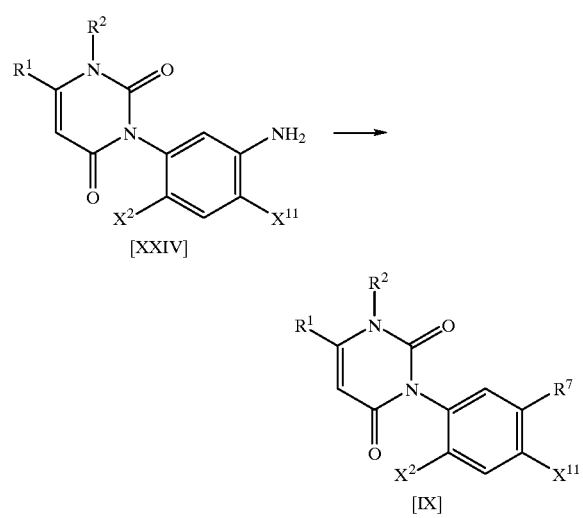

[XXIV]

[IX]

Wherein, $R^1$, $R^2$, $R^7$, $X^2$, and $X^{11}$ are the same as defined above.

The compound [IX] can be produced by diazotizing the compound [XXIV] in a solvent, then, subsequently reacting the diazo compound with a halogenating agent.

<The first step(diazotization reaction)>
reaction temperature: from −20 to 20° C.
reaction time: from an instant to 5 hours
the amount of the diazotizing agent: from 1 mol to excess based on 1 mol of compound [XXIV]
diazotizing agent: nitrites such as sodium nitrite, isoamyl nitrite, t-butyl nitrite and the like Solvent: acetonitrile, hydrochloric acid and the like
<The second step>
reaction temperature: from 0 to 80° C.
reaction time: from an instant to 24 hours
the amounts of the halogenating reagent: from 1 to 3 mol based on 1 mol of compound [XXIV]
halogenating reagent: potassium iodide, copper [I] bromide, copper [I] chloride or hydroborofluoric acid and the like
Solvent: acetonitrile, hydrochloric acid and the like.

The compound [IX] can also be produced by reacting the compound [XXIV] with a diazotizing agent in a solvent in the presence of a halogenating agent.
reaction temperature: from 0 to 80° C.
reaction time: from an instant to 48 hours
the amount of the diazotizing agent: from 1 mol to excess based on 1 mol of compound [XXIV]
diazotizing agent: nitrites such as isoamyl nitrite, t-butyl nitrite and the like
the amounts of the halogenating reagent: from 1 to 3 mol based on 1 mol of compound [XXIV]
halogenating reagent: potassium iodide, copper [I] bromide, copper [I] chloride or hydroborofluoric acid and the like
Solvent: acetonitrile and the like.

When copper [I] bromide is used, the reaction can also be conducted in the presence of copper [II] bromide, and when copper [I] chloride is used, the reaction can also be conducted in the presence of copper [II] chloride.

(Intermediate Production Method 5)

Of compounds [X], the compound wherein W is oxygen or sulfur (i.e. compound [XXVI]) can be produced by a method described in the following scheme.

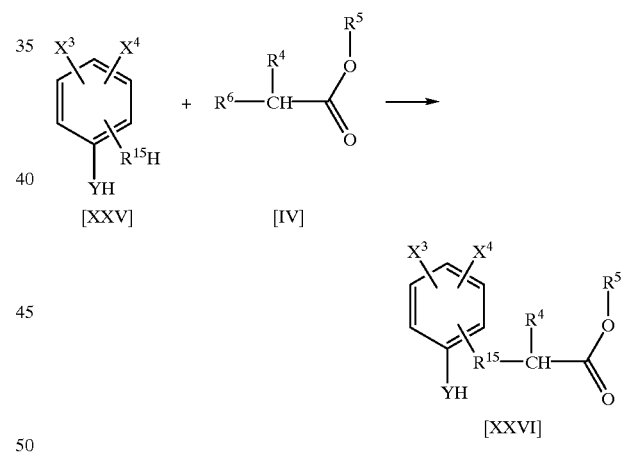

[XXV]    [IV]

[XXVI]

Wherein, $R^4$, $R^5$, $R^6$, $R^{15}$, Y, $X^3$ and $X^4$ are the same as defined above.

The compound [XXVI] can be produced by reacting the compound [XXV] with the compound [IV] in a solvent in the presence of a base.
reaction temperature: from 0 to 200° C.
reaction time: from an instant to 72 hours
amount of compound [IV]: 1 to 3 mol based on 1 mol of compound [XXV]
amount of a base: 1 to 3 mol based on 1 mol of compound [XXV]
base: triethylamine, potassium carbonate, sodium hydride and the like
solvent: tetrahydrofuran, acetonitrile, N,N-dimethylformamide, dimethyl sulfoxide, methanol, water and the like; or mixtures thereof.

(Intermediate Production Method 6)

Of compounds [X], the compound wherein Y is oxygen or sulfur (i.e. compound [XXX]) can be produced by a method described in the following scheme.

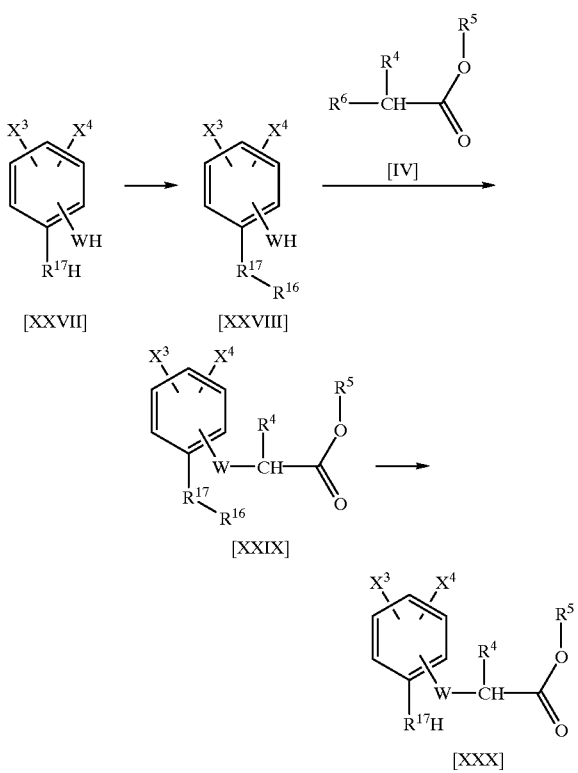

Wherein, $R^4$, $R^5$, $R^6$, $R^{16}$, $R^{17}$, W, n, $X^3$ and $X^4$ have the same meanings as described above.

<Process A6-1>: A process for producing the compound [XXVIII] from the compound [XXVII]

The compound [XXVIII] can be produced by reacting the compound [XXVII] with t-butyldimethylsilyl chloride, isobutene, benzyl chloride, benzyl bromide and the like (see, Protective Groups in Organic Synthesis (A Wiley-Interscience publication)).

<Process A6-2>: A process for producing the compound [XXIX] from the compound [XXVIII]

The compound [XXIX] can be produced by reacting the compound [XXVIII] with the compound [IV] in a solvent in the presence of a base.

reaction temperature: from 0 to 200° C.
reaction time: from an instant to 72 hours
amount of compound [IV]: 1 to 3 mol based on 1 mol of compound [XXVIII]
amount of a base: 1 to 3 mol based on 1 mol of compound [XXVIII]
base: triethylamine, potassium carbonate, sodium hydride and the like
solvent: tetrahydrofuran, acetonitrile, N,N-dimethylformamide, dimethyl sulfoxide, methanol, water and the like; or mixtures thereof <Process A6-3>: A process for producing the compound [XXX] from the compound [XXIX]

The compound [XXX] can be produced by de-protection of the compound [XXIX] according to a method described in "Yuki Kagaku Jikken no Tebiki (published by Manual of Organic Chemical Experiment)", vol. 4, (published by Kagaku Dojin sha), Protective Groups in Organic Synthesis (A Wiley-Interscience publication). Specifically, the compound [XXIX] wherein $R^{18}$ is silyl such as t-butyldimethylsilyl and the like can be de-protected by reacting trifluoroacetic acid or tetrabutylammonium fluoride and the like in a solvent such as methylene chloride, ethyl acetate, water or the like. The compound [XXIX] wherein $R^{18}$ is benzyl which may be substituted such as benzyl and the like can be de-protected by reacting with hydrogen in the presence of a catalyst.

reaction temperature: −20 to 150° C., preferably from 0 to 50° C.
reaction time:from an instant to 48 hours
amount of the catalyst: from 0.001 to 100% by weight based on the compound [XXIX]
catalyst: anhydrous palladium/carbon, water-containing palladium/carbon, platinum oxide and the like
solvent: acetic acid, ethyl acetate, methanol and the like (Intermediate Production Method 7)

Of compounds [XXXI], the compound wherein Y is oxygen or sulfur can be produced by a method described in the following scheme.

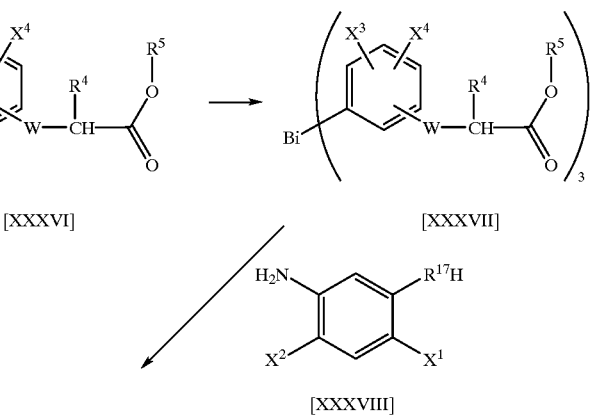

-continued

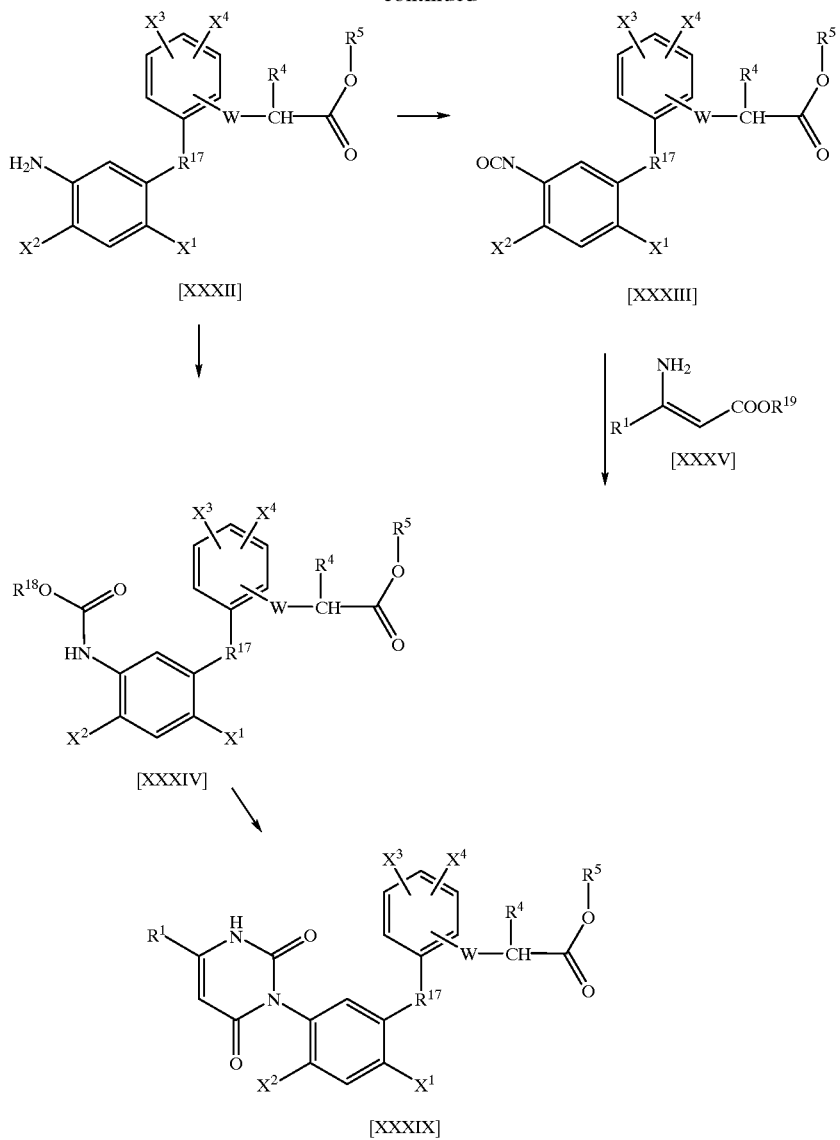

Wherein, $R^1$, $R^4$, $R^5$, $R^7$, $R^{17}$, W, $X^1$, $X^2$, $X^3$ and $X^4$ are the same as defined above, $R^{18}$ represents $C_1$ to $C_6$ alkyl (for example, methyl, ethyl and the like) or phenyl, $R^{19}$ represents $C_1$ to $C_6$ alkyl (for example, methyl, ethyl and the like).

<Process A7-1>: A process for producing the compound [XXXII] from the compound [XXXVI]

The compound [XXXII] can be produced by converting the compound [XXXVI] into the compound [XXXVII], then reacting with the compound [XXXVIII] (see, Bioorganic and Medicinal Chemistry Letters, vol. 5, p. 1035, (1995).

<Process A7-2>: A process for producing the compound [XXXIII] from the compound [XXXII]

The compound [XXXIII] can be produced by a method according to a known method described in U.S. Pat. No. 4,859,229 and the like from the compound [XXXII].

Specifically, the compound [XXXIII] can be produced by isocyanating the compound [XXXII] in a solvent or in the absence of a solvent.

Isocyanating agent: phosgene, trichloromethyl chloroformate, oxalyl chloride and the like Amount of isocyanating agent: from 1 mol to excess based on 1 mol of the compound [XXXII]

Solvent: aromatic hydrocarbons such as benzene, toluene and the like, halogenated aromatic hydrocarbons such as chlorobenzene and the like, esters such as ethyl acetate and the like Reaction Temperature: from room temperature to reflux temperature Reaction Time: from an instant to 48 hours After completion of the reaction, an intended material can be obtained by concentrating a reaction solution itself, and the like. This compound can also be purified by an operation such as re-crystallization and the like.

<Process A7-3>: A process for producing the compound [XXXIV] from the compound [XXXII]

The compound [XXXIV] can be produced by a method according to a known method described in U.S. Pat. No. 4,879,229 and the like from the compound [XXXII].

Specifically, the compound [XXXIV] can be produced by reacting the compound [XXXII] with a compound [b-4] of the formula [b-4]

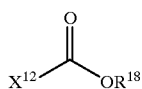

[b-4]

wherein, $R^{18}$ and $X^{12}$ are the same as defined above, in the presence of a base.

This reaction is usually conducted in a solvent, and also can be conducted in the absence of a solvent. The reaction temperature is usually from −20 to 200° C. The reaction time is usually from an instant to 48 hours.

The amount of the compound [b-4] used in the reaction is from 0.5 mol to excess, preferably from 1.0 to 1.2 mol based on 1 mol of the compound [XXXII].

The amount of the base used in the reaction is from 0.5 mol to excess, preferably from 1.0 to 1.2 mol based on 1 mol of the compound [XXXII].

The base includes inorganic bases such as sodium carbonate, sodium hydroxide and the like, organic bases such as pyridine, 4-dimethylaminopyridine, N,N-dimethylaniline, N,N-diethylaniline, triethylamine, diisopropylethylamine and the like.

The solvent include aliphatic halogenated hydrocarbons such as chloroform and the like, ethers such as tetrahydrofuran, 1,4-dioxane and the like, nitrites such as acetonitrile and the like, esters such as ethyl acetate, water or mixtures thereof, and the like.

After completion of the reaction, an intended material can be obtained by a usual post-treatment operation such as by filtrating the reaction solution before concentrating the solution itself, or, pouring the reaction solution into water and collecting the produced crystals by filtration, or, pouring the reaction solution into water and subjecting the mixture to extraction with an organic solvent, concentration and the like. This compound can also be purified by an operation such as re-crystallization, chromatography and the like.

<Process A7-4>: A process for producing the compound [XXXIX] from the compound [XXXIII]

The compound [XXXIX] can be produced by a method according to a known method described in U.S. Pat. No. 4,879,229 and the like from the compound [XXXIII] and the compound [XXXV].

Specifically, the compound [XXXIX] can be produced by reacting the compound [XXXIII] with the compound [XXXV] in a solvent in the presence of a base.

Amount of the compound [XXXV]: 0.5 mol to excess, preferably from 0.8 to 1.2 mol based on 1 mol of the compound [XXXIII]

Base: inorganic bases such as sodium hydride and the like, metal alkoxides such as sodium methoxide, sodium ethoxide and the like Amount of a base: 0.5 mol to excess, preferably from 0.8 to 1.2 mol based on 1 mol of a compound of the general formula [XXXIII]

Solvent: aromatic hydrocarbons such as benzene, toluene and the like; halogenated aromatic hydrocarbons such as chlorobenzene and the like; amides such as N,N-dimethylformamide and the like; ethers such as tetrahydrofuran and the like; halogenated aliphatic hydrocarbons such as chloroform and the like; sulfur compounds such as dimethyl sulfoxide and the like; and mixtures thereof Reaction temperature: −40° C. to solvent reflux temperature Reaction time: instant to 72 hours After completion of the reaction, an intended material can be obtained by a post-treatment operation such as by filtrating a reaction solution before concentrating the solution itself, or, adding an acid to a reaction solution and collecting the produced crystals by filtration, or, adding an acid to a reaction solution, then, subjecting the mixture to extraction with an organic solvent, concentration and the like. As the acid to be added, hydrochloric acid, acetic acid, trifluoroacetic acid, p-toluenesulfonic acid, or aqueous solutions thereof and the like. This compound can also be purified by an operation such as re-crystallization, chromatography and the like.

The resulted compound [XXXIX] can also be reacted with the compound [XXXX] according to a method described in (Production Method 6) without conducting post-treatment such as isolation and the like, to produce the present compound.

<Process A7-5>: A process for producing the compound [XXXIX] from the compound [XXXIV]

The compound [XXXIX] can be produced by a method according to a known method described in U.S. Pat. No. 4,879,229 and the like from the compound [XXXIV] and the compound [XXXV].

Specifically, the compound [XXXIX] can be produced by reacting the compound [XXXIV] with the compound [XXXV] in the presence of a base.

This reaction is usually conducted in a solvent, and the reaction temperature is usually from −20 to 200° C., preferably from 0 to 130° C. The reaction time is usually from an instant to 72 hours.

The amount of the compound [XXXV] used in the reaction is from 0.5 mol to excess, preferably from 0.8 to 1.2 mol based on 1 mol of the compound [XXXIV].

The amount of the base used in the reaction is from 0.5 mol to excess, preferably from 0.8 to 1.2 mol based on the compound [XXXIV].

The base includes organic bases such as 4-dimethylaminopyridine, diisopropylethylamine and the like, inorganic bases such as sodium carbonate, potassium carbonate, sodium hydride, potassium hydride and the like, metal alkoxides such as sodium methoxide, sodium ethoxide, potassium t-butoxide and the like.

The solvent includes ketones such as acetone, methyl isobutyl ketone and the like; aliphatic hydrocarbons such as hexane, heptane, petroleum ether and the like; aromatic hydrocarbons such as benzene, toluene, ethylbenzene, xylene, mesitylene and the like; ethers such as diethyl ether, diisopropyl ether, 1,4-dioxane, tetrahydrofuran, ethylene glycol dimethyl ether, methyl-t-butyl ether and the like; acid amides such as N,N-dimethylformamide, N,N-dimethylacetamide and the like; tertiary amines such as pyridine, N,N-dimethylaniline, N,N-diethylaniline, triethylamine, diisopropylethylamine and the like; sulfur compounds such as dimethyl sulfoxide, sulfolane and the like; or mixtures thereof and the like.

After completion of the reaction, an intended material can be obtained by a usual post-treatment operation such as by filtrating the reaction solution before concentrating the solution itself, or, adding an acid to the reaction solution and collecting the produced crystals by filtration, or, adding an acid to the reaction solution, then, subjecting the mixture to extraction with an organic solvent, concentration and the like. As the acid to be added, there are listed hydrochloric acid, acetic acid, trifluoroacetic acid, p-toluenesulfonic acid, or aqueous solutions thereof and the like. This compound can also be purified by an operation such as re-crystallization, chromatography and the like.

The resulted compound [XXXIX] can also be reacted with the compound [XXXX] according to the method described in (Production Method 6) without conducting post-treatment such as isolation and the like, to produce the present compound.

(Intermediate Production Method 8)

Of compounds [III], the compound wherein Y and W are oxygen or sulfur can also be produced by a method described in the following scheme.

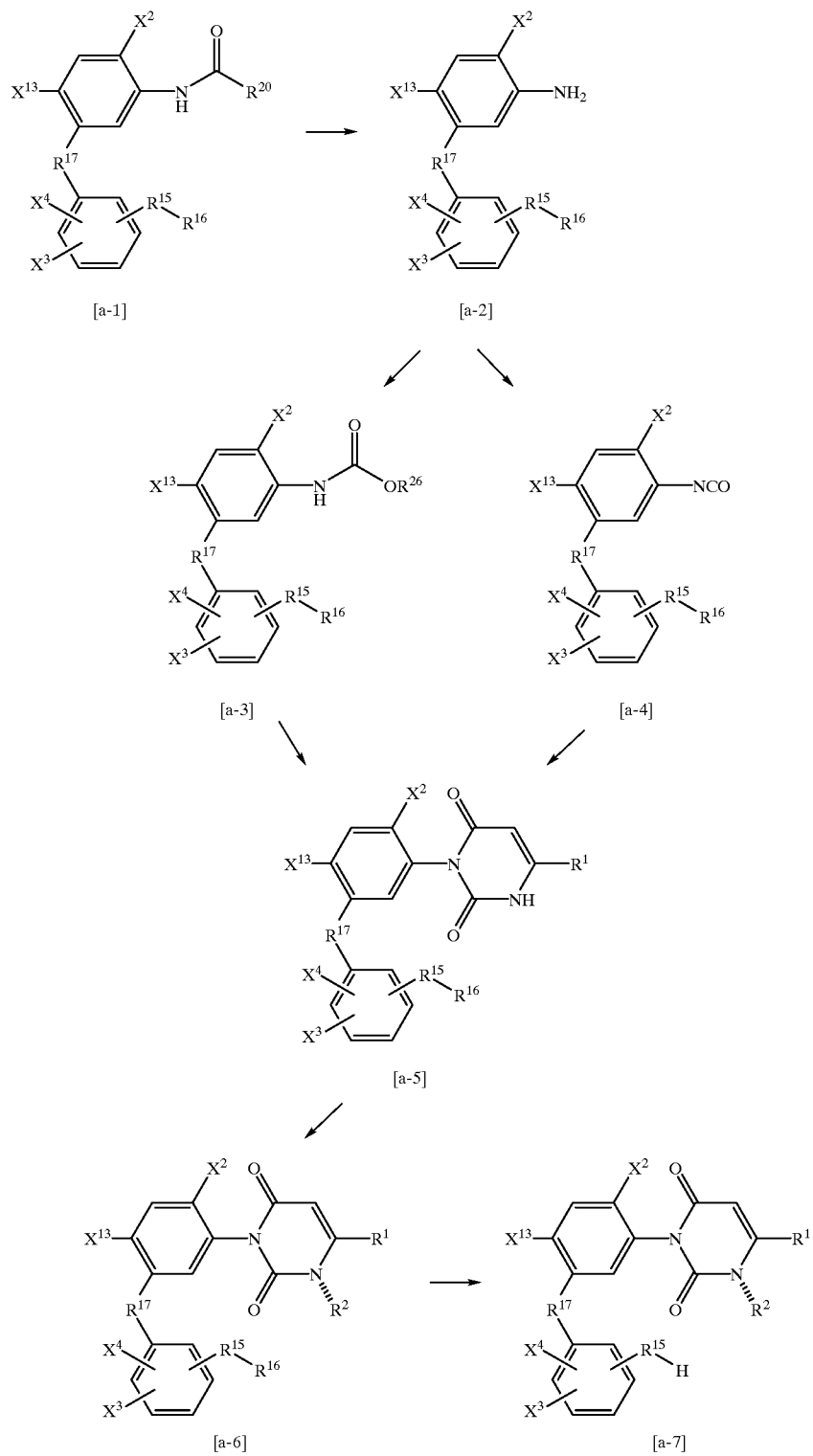

Wherein, $R^1$, $R^2$, $R^{15}$, $R^{16}$, $R^{17}$, $X^2$, $X^3$ and $X^4$ are the same as defined above, $R^{20}$ represents $C_1$ to $C_6$ alkyl which may be substituted such as methyl, ethyl, trifluoromethyl, trichloromethyl and the like, $R^{26}$ represents $C_1$ to $C_6$ alkyl which may be substituted such as methyl, ethyl and the like, phenyl which may be substituted such as phenyl and the like, or phenyl $C_1$ to $C_6$ alkyl which may be substituted such as benzyl and the like, and $X^{13}$ represents nitro, fluorine, chlorine, bromine or iodine.

<Process A8-1>: A process for producing the compound [a-2] from the compound [a-1]

The compound [a-2] can be produced, for example, by de-protecting the compound [a-1] according to a method described in "Yuki Kagaku Jikken no Tebiki (published by Manual of Organic Chemical Experiment)", vol. 4, (published by Kagaku Dojin sha), Protective Groups in Organic Synthesis (A Wiley-Interscience publication), or according to the following method.

This reaction is conducted usually in the absence of a solvent or in a solvent, and the reaction temperature is usually from 0 to 200° C., and the reaction time is usually from an instant to 24 hours. Regarding the amounts of reagents to be used in the reaction, it is theoretical that the amount of the reagent is 1 mol based on 1 mol of the compound [a-1], and the amounts thereof can be changed optionally depending on the reaction condition. As the reagent used, boron trifluoride diethyl etherate, boron trifluoride methanol complex, triethyloxoniumtetrafluoro borate and the like are listed. As the solvent used, there are listed aliphatic hydrocarbons such as hexane, heptane, octane, ligroin and the like; aromatic hydrocarbons such as benzene, toluene, ethylbenzene, xylene, mesitylene and the like; aliphatic halogenated hydrocarbons such as methylene chloride, chloroform, carbon tetrachloride, 1,2-dichloroethane, 1,2,3-trichloropropane and the like, aromatic halogenated hydrocarbons such as chlorobenzene, dichlorobenzene, benzotrifluoride and the like; ethers such as 1,4-dioxane, tetrahydrofuran, ethylene glycol dimethyl ether, methyl-t-butyl ether and the like; alcohols such as methanol, ethanol and the like, or mixtures thereof and the like.

After completion of the reaction, an intended material can be obtained by a post-treatment operation such as by pouring the reaction solution into water, collecting the deposited crystals by filtration and drying them, or, extracting with an organic solvent and drying and concentrating the organic layer, or, concentrating the reaction solution itself, and the like. This compound can also be purified by an operation such as re-crystallization, chromatography and the like.

<Process A8-2>: A process for producing the compound [a-3] from the compound [a-2]

The compound [a-3] can be produced by reacting the compound [a-2] with a compound [b-1] of the formula [b-1]

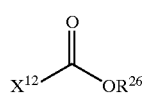

[b-1]

wherein, $R^{26}$ and $X^{12}$ are the same as defined above, in the presence of a base.

This reaction is usually conducted in a solvent, and also can be conducted in the absence of a solvent. The reaction temperature is usually from –20 to 200° C. The reaction time is usually from an instant to 48 hours.

The amount of the compound [b-1] used in the reaction is from 0.5 mol to excess, preferably from 1.0 to 1.2 mol based on 1 mol of the compound [a-2].

The amount of the base used in the reaction is from 0.5 mol to excess, preferably from 1.0 to 1.2 mol based on 1 mol of the compound [a-2].

The base includes inorganic bases such as sodium carbonate, sodium hydroxide and the like, organic bases such as pyridine, 4-dimethylaminopyridine, N,N-dimethylaniline, N,N-diethylaniline, triethylamine, diisopropylethylamine and the like.

The solvent include aliphatic halogenated hydrocarbons such as chloroform and the like, ethers such as tetrahydrofuran, 1,4-dioxane and the like, nitrites such as acetonitrile and the like, esters such as ethyl acetate, water or mixtures thereof, and the like.

After completion of the reaction, an intended material can be obtained by a usual post-treatment operation such as by filtrating the reaction solution before concentrating the solution itself, or, pouring the reaction solution into water and collecting the produced crystals by filtration, or, pouring the reaction solution into water and subjecting the mixture to extraction with an organic solvent, concentration and the like. This compound can also be purified by an operation such as re-crystallization, chromatography and the like.

<Process A8-3>: A process for producing the compound [a-5] from the compound [a-3]

The compound [a-5] can be produced by reacting the compound [a-3] with the compound [XXXV] in the presence of a base.

This reaction is usually conducted in a solvent, and the reaction temperature is usually from –20 to 200° C., preferably from 0 to 130° C. The reaction time is usually from an instant to 72 hours.

The amount of the compound [XXXV] used in the reaction is from 0.5 mol to excess, preferably from 0.8 to 1.2 mol based on 1 mol of the compound [a-3].

The amount of the base used in the reaction is from 0.5 mol to excess, preferably from 0.8 to 1.2 mol based on the compound [a-3].

The base includes organic bases such as 4-dimethylaminopyridine, diisopropylethylamine and the like, inorganic bases such as sodium carbonate, potassium carbonate, sodium hydride, potassium hydride and the like, metal alkoxides such as sodium methoxide, sodium ethoxide, potassium t-butoxide and the like.

The solvent includes ketones such as acetone, methyl isobutyl ketone and the like; aliphatic hydrocarbons such as hexane, heptane, petroleum ether and the like; aromatic hydrocarbons such as benzene, toluene, ethylbenzene, xylene, mesitylene and the like; ethers such as diethyl ether, diisopropyl ether, 1,4-dioxane, tetrahydrofuran, ethylene glycol dimethyl ether, methyl-t-butyl ether and the like; nitro compounds such as nitromethane, nitrobenzene and the like; acid amides such as N,N-dimethylformamide, N,N-dimethylacetamide and the like; tertiary amines such as pyridine, N,N-dimethylaniline, N,N-diethylaniline, triethylamine, diisopropylethylamine and the like; sulfur compounds such as dimethyl sulfoxide, sulfolane and the like; or mixtures thereof and the like.

After completion of the reaction, an intended material can be obtained by a post-treatment operation such as by filtrating the reaction solution before concentrating the solution itself, or, adding an acid to the reaction solution and collecting the produced crystals by filtration, or, adding an acid to the reaction solution, then, subjecting the mixture to extraction with an organic solvent, concentration and the like. As the acid to be added, there are listed hydrochloric acid, acetic acid, trifluoroacetic acid, p-toluenesulfonic acid, or aqueous solutions thereof and the like. This compound can also be purified by an operation such as chromatography, re-crystallization and the like. Further, the compound [a-5] can also be used in a reaction of the following process without isolation.

<Process A8-4>: A process for producing the compound [a-4] from the compound [a-2]

The compound [a-4] can be produced by isocyanating the compound [a-2] by reaction with an isocyanating agent in a solvent or in the absence of a solvent.

Isocyanating agent: phosgene, trichloromethyl chloroformate, oxalyl chloride and the like Amount of isocyanating agent: from 1 mol to excess based on 1 mol of the compound [a-2]

Solvent: aromatic hydrocarbons such as benzene, toluene and the like, halogenated aromatic hydrocarbons such as chlorobenzene and the like, esters such as ethyl acetate and the like Reaction Temperature: from room temperature to reflux temperature Reaction Time: from an instant to 48 hours After completion of the reaction, an intended material can be obtained by concentrating the reaction solution itself, and the like. This compound can also be purified by an operation such as re-crystallization and the like.

<Process A8-5>: A process for producing the compound [a-5] from the compound [a-4]

The compound [a-5] can be produced by reacting the compound [a-4] with the compound [XXXV] in a solvent in the presence of a base.

Amount of the compound [XXXV]: 0.9 to 10 mol based on 1 mol of the compound [a-4]

Base: inorganic bases such as sodium hydride, potassium hydroxide, sodium hydroxide and the like, metal alkoxides such as sodium methoxides, sodium ethoxides and the like Amount of a base: 0.1 to 10 mol based on 1 mol of the compound [a-4]

Solvent: aromatic hydrocarbons such as benzene, toluene and the like; halogenated aromatic hydrocarbons such as chlorobenzene and the like; amides such as N,N-dimethylformamide and the like; ethers such as tetrahydrofuran and the like; halogenated aliphatic hydrocarbons such as chloroform and the like; sulfur compounds such as dimethyl sulfoxide and the like; and mixtures thereof Reaction temperature: −40° C. to solvent reflux temperature Reaction time: instant to 72 hours After completion of the reaction, an intended material can be obtained by a post-treatment operation such as by neutralizing, then, pouring a reaction solution into water, and collecting the deposited crystals and drying them, or, extracting with an organic solvent and drying and concentrating the organic layer, or, concentrating a reaction solution itself, and the like. This compound can also be purified by an operation such as re-crystallization, chromatography and the like.

The resulted compound [a-5] can also be used in a reaction of the following process without isolation.

<Process A8-6>: A process for producing the compound [a-6] from the compound [a-5]

The compound [a-6] can be produced by reacting the compound [a-5] with the compound [XXXX] in the presence of a base.

This reaction is usually conducted in a solvent, and the reaction temperature is usually from −20 to 200° C., preferably from 0 to 100° C. The reaction time is usually from an instant to 48 hours.

The amount of the compound [XXXX] used in the reaction is from 0.5 mol to excess, preferably from 0.8 to 1.2 mol based on 1 mol of the compound [a-5].

The amount of the base used in the reaction is from 0.5 mol to excess, preferably from 0.8 to 1.2 mol based on 1 mol of the compound [a-5].

The base includes organic bases such as pyridine, 4-dimethylaminopyridine, N,N-dimethylaniline, N,N-diethylaniline, triethylamine, diisopropylethylamine and the like, sodium carbonate, potassium carbonate, sodium hydride, potassium hydride and the like.

The solvent include aliphatic hydrocarbons such as hexane, heptane, octane, ligroin, cyclohexane and the like; aromatic hydrocarbons such as benzene, toluene, ethylbenzene, xylene, mesitylene and the like; ethers such as diethyl ether, diisopropyl ether, 1,4-dioxane, tetrahydrofuran, ethylene glycol dimethyl ether, methyl-t-butyl ether and the like; nitro compounds such as nitromethane, nitrobenzene and the like; acid amides such as N,N-dimethylformamide, N,N-dimethylacetamide and the like; tertiary amines such as pyridine, N,N-dimethylaniline, N,N-diethylaniline, triethylamine, diisopropylethylamine and the like; sulfur compounds such as dimethyl sulfoxide, sulfolane and the like; alcohols such as methanol, ethanol, ethylene glycol, isopropanol, t-butnol and the like; or mixtures thereof and the like.

After completion of the reaction, an intended material can be obtained by a usual post-treatment operation such as by filtrating a reaction solution before concentrating the solution itself, or, pouring a reaction solution into water and collecting the produced crystals, or, pouring a reaction solution into water, then, subjecting the mixture to extraction with an organic solvent, concentration and the like.

This compound can also be purified by an operation such as chromatography, re-crystallization and the like.

<Process A8-7>: A process for producing the compound [a-7] from the compound [a-6].

The compound [a-7] can be produced according to the Process A1-5 of the Intermediate Production Method 1 from the compound [a-6]

(Intermediate Production Method 9)

The compound [a-1] can be produced by a method described in the following scheme. (In the scheme, the compound [a-1] is represented as compound [a-9] or compound [a-11].)

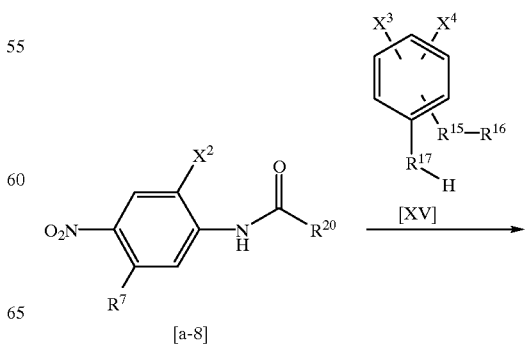

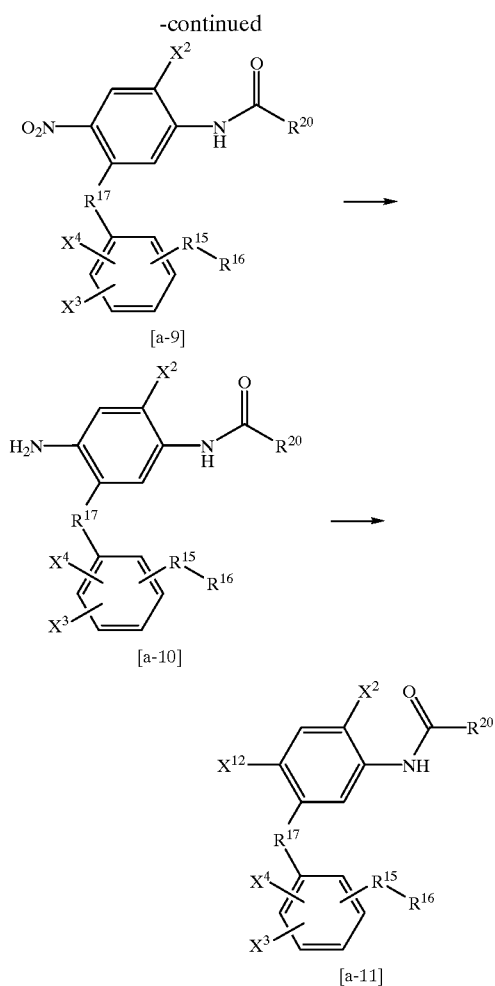

Wherein $R^7$, $R^{15}$, $R^{16}$, $R^{17}$, $R^{20}$, $X^2$, $X^3$, $X^4$ and $X^{12}$ are the same Ad as defined above.

<Process A9-1>: A process for producing the compound [a-9] from the compound [a-8]

The compound [a-9] can be produced by reacting the compound [a-8] with the compound [XV] in the presence of a base.

This reaction is conducted usually in the absence of a solvent or in a solvent, and the reaction temperature is usually from 0 to 200° C., and the reaction time is usually from an instant to 24 hours.

Regarding the amounts of reagents to be used in the reaction, it is theoretical that the amount of the compound [XV] is 1 mol and the amount of the base is 1 mol based on 1 mol of the compound [a-8], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, metal alkoxides such as sodium methoxide, sodium ethoxide, potassium t-butoxide and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, sodium hydroxide, potassium hydroxide, calcium hydroxide, barium hydroxide and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; alcohols such as methanol, ethanol, ethylene glycol, isopropanol, t-butanol and the like; or mixtures thereof.

After completion of the reaction, an intended material can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the intended material can also be purified by a procedure such as chromatography, re-crystallization and the like.

<Process A9-2>: A process for producing the compound [a-10] from the compound [a-9]

The compound [a-10] can be produced, for example, by reducing the compound [a-9] using an iron powder in the presence of an acid in a solvent.

The reaction temperature of this reaction is usually from 0 to 200° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [a-9], and the amounts thereof can be changed optionally depending on the reaction condition.

As the acid to be used, acetic acid and the like are listed.

As the solvent to be used, there are listed, for example, water, acetic acid, ethyl acetate and the like or mixtures thereof.

After completion of the reaction, an intended material can be obtained by a usual post-treatment such as by pouring a reaction solution into water directly or after filtration and collecting the produced crystals, or, extracting with an organic solvent, neutralization, concentration and the like.

The intended material can also be purified by a procedure such as chromatography, re-crystallization and the like.

<Process A9-3>: A process for producing the compound [a-11] from the compound [a-10].

The compound [a-11] can be produced by i) diazotizing the compound [a-10] in a solvent, then, ii) subsequently, reacting the diazo compound with potassium iodide, copper (I) bromide, copper (I) chloride or hydroborofluoric acid in a solvent.

In the diazotization reaction of the first step, the reaction temperature is from −20 to 20° C., and the reaction time is usually from an instant to 5 hours.

Regarding the amounts of reagents to be used in the reaction, it is theoretical that the amount of the diazotization agent is 1 mol based on 1 mol of the compound [a-10], and the amounts thereof can be changed optionally depending on the reaction condition.

As the diazotization agent to be used, nitrites such as sodium nitrite, potassium nitrite, isoamyl nitrite, t-butyl nitrite and the like, are listed.

As the solvent, there are listed, for example, acetonitrile, hydrobromic acid, hydrochloric acid, sulfuric acid, water and the like or mixtures thereof.

The reaction solution after completion of the reaction is used as it is in the following reaction.

In the reaction of the second step, the reaction temperature is from 0 to 80° C., and the reaction time is usually from an instant to 24 hours.

Regarding the amounts of reagents to be used in the reaction, each amount of potassium iodide, copper (I) bromide, copper (I) chloride or hydroborofluoric acid is from 1 to 3 mol based on 1 mol of the compound [a-10], and the amounts thereof can be changed optionally depending on the reaction condition. When copper [I] bromide is used, the reaction can also be conducted in the presence of copper (II) bromide, and when copper (I) chloride is used, the reaction can also be conducted in the presence of copper (II) chloride.

As the solvent to be used, there are listed, for example, acetonitrile, diethyl ether, t-butyl methyl ether, hydrobromic acid, hydrochloric acid, sulfuric acid, water and the like or mixtures thereof.

After completion of the reaction, an intended material can be obtained by collecting the produced crystals by filtration (if necessary, by adding water), or, extracting with an organic solvent, concentration and the like.

The intended material can also be purified by a procedure such as chromatography, re-crystallization and the like.

Further, this reaction is not limited to the above-mentioned methods, and production can also be conducted by reacting the compound [a-10] with the diazotizing agent in a solvent (for example, acetonitrile, diethyl ether, t-butyl methyl ether, hydrobromic acid, hydrochloric acid, sulfuric acid, water or mixtures thereof) in the presence of potassium iodide, copper (I) bromide, copper (I) chloride or hydroborofluoric acid.

(Intermediate Production Method 10)

The compound [III] wherein $X^1$ is nitro, fluorine, chlorine, bromine or iodine, and Y and W are oxygen or sulfur can also be produced by a method described in the following scheme.

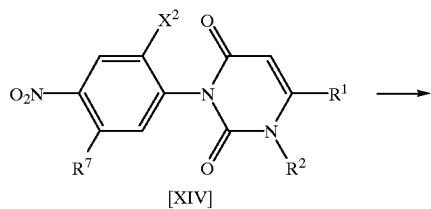

[XIV]

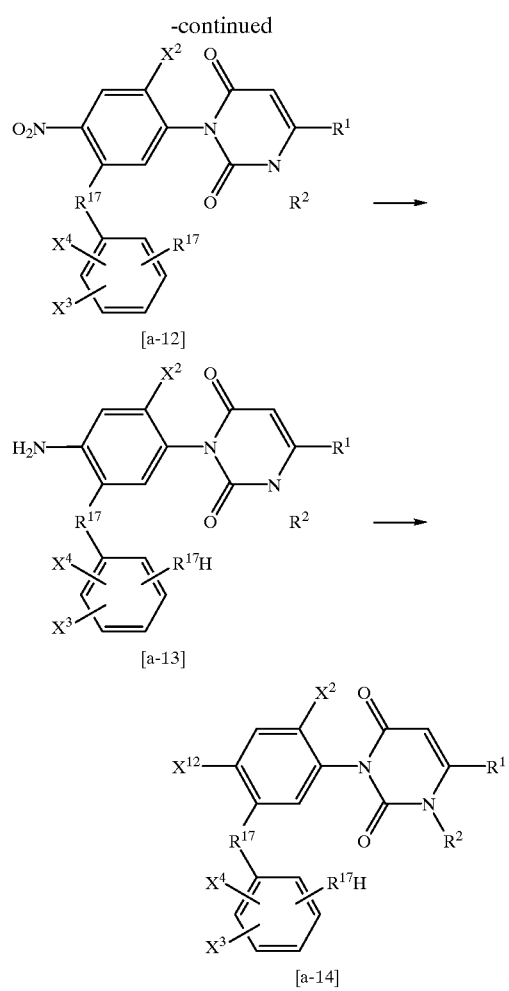

Wherein, $R^1$, $R^2$, $R^7$, $R^{17}$, $X^2$, $X^3$, $X^4$ and $X^{12}$ are the same as defined above.

<Process A10-1>: A process for producing the compound [a-12] from the compound [XIV]

The compound [a-12] can be produced by reacting the compound [XIV] with the compound [b-2] of the formula [b-2]

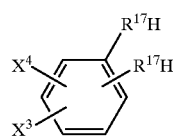

[b-2]

wherein, $R^{17}$, $X^3$ and $X^4$ are the same as defined above, in the presence of a base.

This reaction is conducted usually in the absence of a solvent or in a solvent, and the reaction temperature is usually from 0 to 200° C., and the reaction time is usually from an instant to 24 hours.

Regarding the amounts of reagents to be used in the reaction, it is theoretical that the amount of the compound [b-2] is 1 mol and the amount of the base is 1 mol based on 1 mol of the compound [XIV], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as sulfolane and the like; or mixtures thereof.

After completion of the reaction, an intended material can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the intended material can also be purified by a procedure such as chromatography, re-crystallization and the like.

<Process A10-2>: A process for producing the compound [a-13] from the compound [a-12]

The compound [a-13] can be produced, for example, by reducing the compound [a-12] using an iron powder in the presence of an acid in a solvent.

The reaction temperature of this reaction is usually from 0 to 200° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [a-12], and the amounts thereof can be changed optionally depending on the reaction condition.

As the acid to be used, acetic acid and the like are listed.

As the solvent to be used, there are listed, for example, water, acetic acid, ethyl acetate and the like or mixtures thereof.

After completion of the reaction, an intended material can be obtained by pouring a reaction solution into water directly or after filtration and collecting the produced crystals by filtration, or, extracting with an organic solvent, neutralization, concentration and the like.

The intended material can also be purified by a procedure such as chromatography, re-crystallization and the like.

<Process A10-3>: A process for producing the compound [a-14] from the compound [a-13].

The compound [a-14] can be produced by i) diazotizing the compound [a-13] in a solvent, then, ii) subsequently, reacting the diazo compound with potassium iodide, copper (I) bromide, copper (I) chloride or hydroborofluoric acid in a solvent.

In the diazotization reaction of the first step, the reaction temperature is from −20 to 20° C., and the reaction time is usually from an instant to 5 hours.

Regarding the amounts of reagents to be used in the reaction, it is theoretical that the amount of the diazotization agent is 1 mol based on 1 mol of the compound [a-13], and the amounts thereof can be changed optionally depending on the reaction condition.

As the diazotization agent to be used, nitrites such as sodium nitrite, potassium nitrite and the like, organic nitrous acid compounds such as isoamyl nitrite, t-butyl nitrite and the like, are listed.

As the solvent, there are listed, for example, acetonitrile, hydrobromic acid, hydrochloric acid, sulfuric acid, water and the like or mixtures thereof.

The reaction solution after completion of the reaction is used as it is in the following reaction.

In the reaction of the second step, the reaction temperature is from 0 to 80° C., and the reaction time is usually from an instant to 24 hours.

Regarding the amounts of reagents to be used in the reaction, each amount of potassium iodide, copper (I) bromide, copper (I) chloride or hydroborofluoric acid is from 1 to 3 mol based on 1 mol of the compound [a-13], and the amounts thereof can be changed optionally depending on the reaction condition. When copper (I) bromide is used, the reaction can also be conducted in the presence of copper (II) bromide, and when copper (I) chloride is used, the reaction can also be conducted in the presence of copper (II) chloride.

As the solvent to be used, there are listed, for example, acetonitrile, diethyl ether, t-butyl methyl ether, hydrobromic acid, hydrochloric acid, sulfuric acid, water and the like or mixtures thereof.

After completion of the reaction, an intended material can be obtained by collecting the produced crystals (if necessary, by adding water), or, extracting with an organic solvent, concentration and the like.

The intended material can also be purified by a procedure such as chromatography, re-crystallization and the like.

Further, this reaction is not limited to the above-mentioned methods, and production can also be conducted by reacting the compound [a-13] with the diazotizing agent in a solvent (for example, acetonitrile, diethyl ether, t-butyl methyl ether, hydrobromic acid, hydrochloric acid, sulfuric acid, water or mixtures thereof) in the presence of potassium iodide, copper (I) bromide, copper (I) chloride or hydroborofluoric acid.

(Intermediate Production Method 11)

Of the compounds [III], the compound wherein Y and W are oxygen can also be produced by a method described in the following scheme.

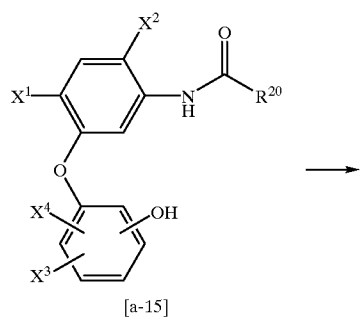

[a-15]

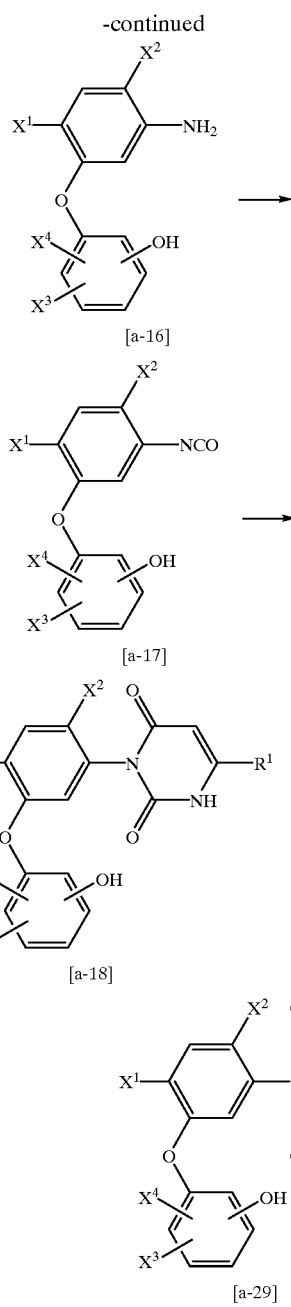

Wherein, $R^1$, $R^2$, $R^{20}$, $X^1$, $X^2$, $X^3$ and $X^4$ are the same as defined above.

<Process A11-1>: A process for producing the compound [a-16] from the compound [a-15]

The compound [a-16] can be produced, for example, by de-protecting the compound [a-15] according to a method described in "Yuki Kagaku Jikken no Tebiki (published by Manual of Organic Chemical Experiment)", vol. 4, (published by Kagaku Dojin sha), Protective Groups in Organic Synthesis (published by A Wiley-Interscience publication), or according to the following method.

This reaction is conducted usually in the absence of a solvent or in a solvent, and the reaction temperature is usually from 0 to 200° C., and the reaction time is usually from an instant to 24 hours. Regarding the amounts of reagents to be used in the reaction, it is theoretical that the amount of the reagent is 1 mol based on 1 mol of the compound [a-15], and the amounts thereof can be changed optionally depending on the reaction condition. As the reagent used, boron trifluoride methanol complex, triethyloxoniumtetrafluoro borate and the like are listed. As the solvent used, there are listed aliphatic hydrocarbons such as hexane, heptane, octane, ligroin and the like; aromatic hydrocarbons such as benzene, toluene, ethylbenzene, xylene, mesitylene and the like; aliphatic halogenated hydrocarbons such as methylene chloride, chloroform, carbon tetrachloride, 1,2-a dichloroethane, 1,2,3-trichloropropane and the like, aromatic halogenated hydrocarbons such as chlorobenzene, dichlorobenzene, benzotrifluoride and the like; ethers such as 1,4-dioxane, tetrahydrofuran, ethylene glycol dimethyl ether, methyl-t-butyl ether and the like; alcohols such as methanol, ethanol and the like, or mixtures thereof and the like.

After completion of the reaction, an intended material can be obtained by a post-treatment operation such as by pouring a reaction solution into water and collecting the deposited crystals and drying them, or, extracting with an organic solvent and drying and concentrating the organic layer, or, concentrating a reaction solution itself, and the like. This compound can also be purified by an operation such as re-crystallization, chromatography and the like.

<Process A11-2>: A process for producing the compound [a-17] from the compound [a-16]

The compound [a-17] can be produced by isocyanating the compound [a-16] by reaction with an isocyanating agent in a solvent or in the absence of a solvent.

Isocyanating agent: phosgene, trichloromethyl chloroformate, oxalyl chloride and the like Amount of isocyanating agent: from 1 mol to excess based on 1 mol of the compound [a-16]

Solvent: aromatic hydrocarbons such as benzene, toluene and the like, halogenated aromatic hydrocarbons such as chlorobenzene and the like, esters such as ethyl acetate and the like Reaction Temperature: from room temperature to reflux temperature Reaction Time: from an instant to 48 hours After completion of the reaction, an intended material can be obtained by concentrating a reaction solution itself, and the like. This compound can also be purified by an operation such as re-crystallization and the like.

<Process A11-3>: A process for producing the compound [a-18] from the compound [a-17]

The compound [a-18] can be produced by reacting the compound [a-17] with the compound [XXXV] in a solvent in the presence of a base.

Amount of the compound [XXXV]: 0.9 to 10 mol based on 1 mol of the compound [a-17]

Base: inorganic bases such as sodium hydride, potassium hydride, sodium hydroxide and the like, metal alkoxides such as sodium methoxide, sodium ethoxide and the in like Amount of a base: 0.1 to 10 mol based on 1 mol of the compound [a-17]

Solvent: aromatic hydrocarbons such as benzene, toluene and the like; halogenated aromatic hydrocarbons such as chlorobenzene and the like; amides such as N,N-dimethylformamide and the like; ethers such as tetrahydrofuran and the like; halogenated aliphatic hydrocarbons such as chloroform and the like; and mixtures thereof Reaction temperature: −40° C. to solvent reflux temperature Reaction time: instant to 72 hours After completion of the reaction, an intended material can be obtained by a post-treatment operation such as by neutralizing, then, pouring a reaction solution into water, and collecting the deposited crystals by filtration, or, extracting with an organic solvent and drying and concentrating the organic layer, or, concentrating a reaction solution itself, and the like. This compound can also be purified by an operation such as re-crystallization, chromatography and the like.

The compound [a-18] can also be used in the reaction of the following process without isolation.

<Process A11-4>: A process for producing the compound [a-29] from the compound [a-18]

The compound [a-29] can be produced by reacting the compound [a-18] with the compound [XXXX] in the presence of a base.

This reaction is usually conducted in a solvent, and the reaction temperature is usually from −20 to 200° C., preferably from 0 to 100° C. The reaction time is usually from an instant to 48 hours.

The amount of the compound [XXXX] used in the reaction is from 0.5 mol to excess, preferably from 0.8 to 1.2 mol based on 1 mol of the compound [a-18].

The amount of the base used in the reaction is from 0.5 mol to excess, preferably from 0.8 to 1.2 mol based on 1 mol of the compound [a-18].

The base includes organic bases such as pyridine, 4-dimethylaminopyridine, N,N-dimethylaniline, N,N-diethylaniline, triethylamine, diisopropylethylamine and the like, sodium carbonate, potassium carbonate, sodium hydride, potassium hydride and the like.

The solvent include aliphatic hydrocarbons such as hexane, heptane, octane, ligroin, cyclohexane, petroleum ether and the like; aromatic hydrocarbons such as benzene, toluene, ethylbenzene, xylene, mesitylene and the like; ethers such as diethyl ether, diisopropyl ether, 1,4-dioxane, tetrahydrofuran, ethylene glycol dimethyl ether, methyl-t-butyl ether and the like; nitro compounds such as nitromethane, nitrobenzene and the like; acid amides such as N,N-dimethylformamide, N,N-dimethylacetamide and the like; tertiary amines such as pyridine, N,N-dimethylaniline, -N,N-diethylaniline, triethylamine, diisopropylethylamine and the like; sulfur compounds such as dimethyl sulfoxide, sulfolane and the like; or mixtures thereof and the like.

After completion of the reaction, an intended material can be obtained by a usual post-treatment operation such as by filtrating a reaction solution before concentrating the solution itself, or, pouring a reaction solution into water and collecting the produced crystals, or, pouring a reaction solution into water, then, subjecting the mixture to extraction with an organic solvent, concentration and the like. This compound can also be purified by an operation such as chromatography, re-crystallization and the like.

(Intermediate Production Method 12)

The compound [XXXII] wherein $X^1$ is nitro, fluorine, chlorine, bromine or iodine can also be produced by a method described in the following scheme.

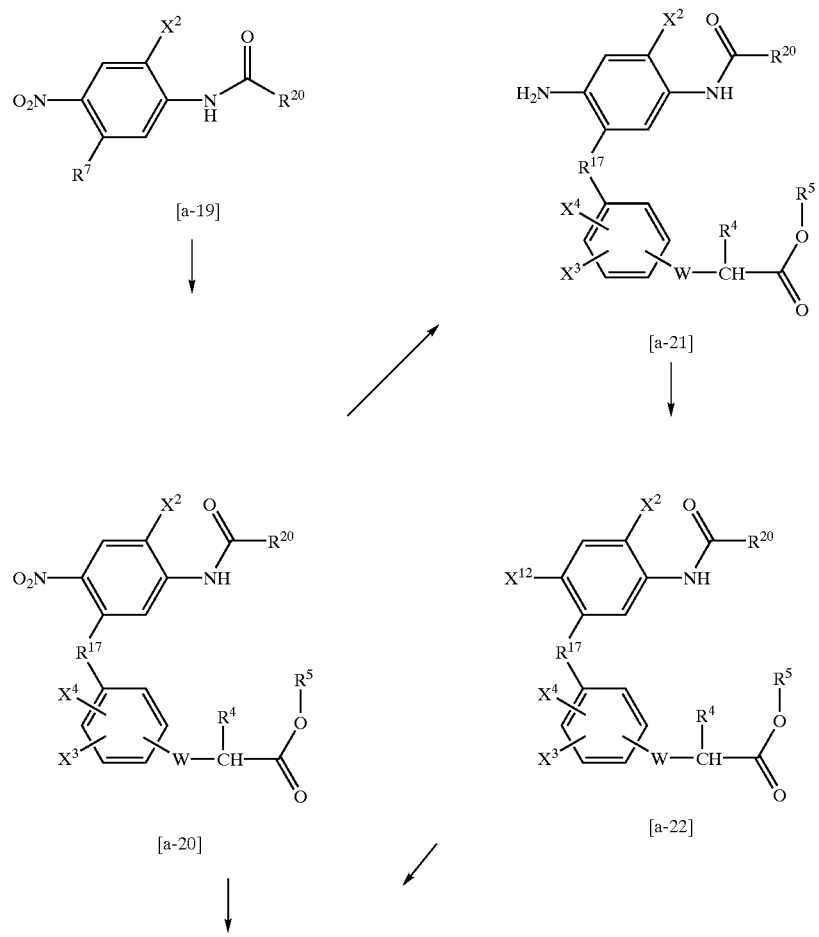

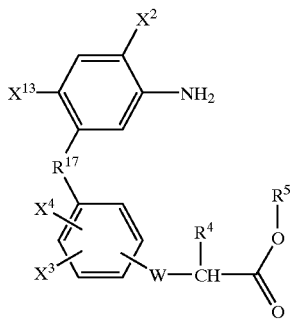

[a-23]

Wherein, $R^4$, $R^5$, $R^7$, $R^{17}$, $R^{20}$, W, $X^2$, $X^3$, $X^4$, $X^{12}$ and $X^{13}$ are the same as defined above.

<Process A12-1>: A process for producing the compound [a-20] from the compound [a-19]

The compound [a-20] can be produced by reacting the compound [a-19] with a compound [b-3] of the formula [b-3]

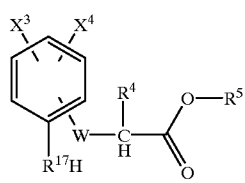

[b-3]

wherein, $R^4$, $R^5$, $R^{17}$, W, Y, $X^3$, and $X^4$ are the same as defined above,
in the presence of a base.

This reaction is conducted usually in the absence of a solvent or in a solvent, and the reaction temperature is usually from 0 to 200° C., and the reaction time is usually from an instant to 24 hours.

Regarding the amounts of reagents to be used in the reaction, it is theoretical that the amount of the compound [b-3] is 1 mol and the amount of the base is 1 mol based on 1 mol of the compound [a-19], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

After completion of the reaction, an intended material can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the intended material can also be purified by a procedure such as chromatography, re-crystallization and the like.

<Process A12-2>: A process for producing the compound [a-21] from the compound [a-20]

The compound [a-21] can be produced, for example, by reducing the compound [a-20] using an iron powder in the presence of an acid in a solvent.

The reaction temperature of this reaction is usually from 0 to 200° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [a-20], and the amounts thereof can be changed optionally depending on the reaction condition.

As the acid to be used, acetic acid and the like are listed.

As the solvent to be used, there are listed, for example, water, acetic acid, ethyl acetate and the like or mixtures thereof.

After completion of the reaction, an intended material can be obtained by usual post-treatment such as by pouring a reaction solution into water directly or after filtration and collecting the produced crystals by filtration, or, extracting with an organic solvent, neutralization, concentration and the like.

The intended material can also be purified by a procedure such as chromatography, re-crystallization and the like.

<Process A12-3>: A process for producing the compound [a-22] from the compound [a-21].

The compound [a-22] can be produced by i) diazotizing the compound [a-21] in a solvent, then, ii) subsequently, reacting the diazo compound with potassium iodide, copper (I) bromide, copper (I) chloride or hydroborofluoric acid in a solvent.

In the diazotization reaction of the first step, the reaction temperature is from −20 to 20° C., and the reaction time is usually from an instant to 5 hours.

Regarding the amounts of reagents to be used in the reaction, it is theoretical that the amount of the diazotization agent is 1 mol based on 1 mol of the compound [a-21], and the amounts thereof can be changed optionally depending on the reaction condition.

As the diazotization agent to be used, nitrites such as sodium nitrite, potassium nitrite, isoamyl nitrite, t-butyl nitrite and the like, are listed.

As the solvent, there are listed, for example, acetonitrile, hydrobromic acid, hydrochloric acid, sulfuric acid, water and the like or mixtures thereof.

The reaction solution after completion of the reaction is used as it is in the following reaction.

In the reaction of the second step, the reaction temperature is from 0 to 80° C., and the reaction time is usually from an instant to 24 hours.

Regarding the amounts of reagents to be used in the reaction, each amount of potassium iodide, copper (I) bromide, copper (I) chloride or hydroborofluoric acid is from 1 to 3 mol based on 1 mol of the compound [a-21], and the amounts thereof can be changed optionally depending on the reaction condition When copper (I) bromide is used, the reaction can also be conducted in the presence of copper (II) bromide, and when copper (I) chloride is used, the reaction can also be conducted in the presence of copper (II) chloride.

As the solvent to be used, there are listed, for example, acetonitrile, diethyl ether, t-butyl methyl ether, hydrobromic acid, hydrochloric acid, sulfuric acid, water and the like or mixtures thereof.

After completion of the reaction, an intended material can be obtained by usual post-treatment such as collecting the produced crystals (if necessary, by adding water), or, extracting with an organic solvent, concentration and the like.

The intended material can also be purified by a procedure such as chromatography, re-crystallization and the like.

Further, this reaction is not limited to the above-mentioned methods, and production can also be conducted by reacting the compound [a-21] with the diazotizing agent in a solvent (for example, acetonitrile, diethyl ether, t-butyl methyl ether, hydrobromic acid, hydrochloric acid, sulfuric acid, water or mixtures thereof) in the presence of potassium iodide, copper (I) bromide, copper (I) chloride or hydroborofluoric acid.

When copper (I) bromide is used, the reaction can also be conducted in the presence of copper (II) bromide, and when copper (I) chloride is used, the reaction can also be conducted in the presence of copper (II) chloride.

<Process A12-4>: A process for producing the compound [a-23] from the compound [a-22]

The compound [a-23] can be produced, for example, by de-protecting the compound [a-22] according to a method described in "Yuki Kagaku Jikken no Tebiki (published by Manual of Organic Chemical Experiment)", vol. 4, (published by Kagaku Dojin sha), Protective Groups in Organic Synthesis (published by A Wiley-Interscience publication), or according to the following method.

This reaction is conducted usually in the absence of a solvent or in a solvent, and the reaction temperature is usually from 0 to 200° C., and the reaction time is usually from an instant to 24 hours. Regarding the amounts of reagents to be used in the reaction, it is theoretical that the amount of the reagent is 1 mol based on 1 mol of the compound [a-22], and the amounts thereof can be changed optionally depending on the reaction condition. As the reagent used, boron trifluoride methanol complex, triethyloxoniumtetrafluoro borate and the like are listed. As the solvent used, there are listed aliphatic hydrocarbons such as hexane, heptane, octane, ligroin and the like; aromatic hydrocarbons such as benzene, toluene, ethylbenzene, xylene, mesitylene and the like; aliphatic halogenated hydrocarbons such as methylene chloride, chloroform, carbon tetrachloride, 1,2-dichloroethane, 1,2,3-trichloropropane and the like, aromatic halogenated hydrocarbons such as chlorobenzene, dichlorobenzene, benzotrifluoride and the like; ethers such as 1,4-dioxane, tetrahydrofuran, ethylene glycol dimethyl ether, methyl-t-butyl ether and the like; alcohols such as methanol, ethanol and the like, or mixtures thereof and the like.

After completion of the reaction, an intended material can be obtained by a post-treatment operation such as by pouring a reaction solution into water and collecting the deposited crystals by filtration and drying them, or, extracting with an organic solvent and drying and concentrating the organic layer, or, concentrating a reaction solution itself, and the like. This compound can also be purified by an operation such as re-crystallization, chromatography and the like.

<Process A12-5>: A process for producing the compound [a-23] from the compound [a-20]

The compound [a-23] wherein $X^{13}$ is nitro can be produced according to the method described in <Process A12-4>from the compound [a-20].

(Intermediate Production Method 13)

The compound [XXXIV] and the compound [a-15] wherein $X^1$ is nitro, fluorine, chlorine, bromine or iodine, the compound [a-20], and the compound [a-22] can also be produced by methods described in the following scheme.

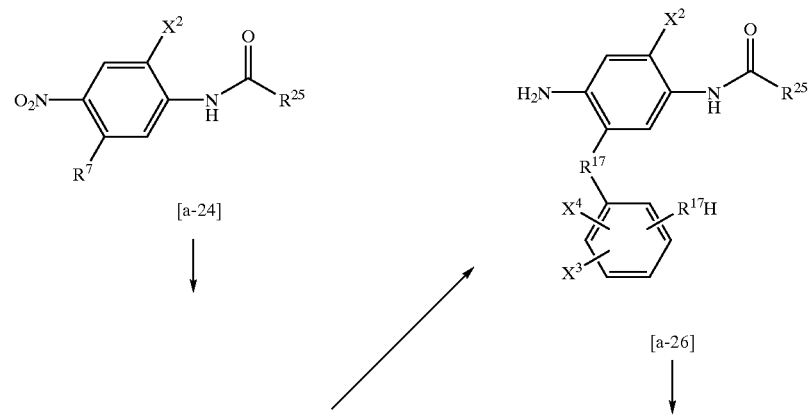

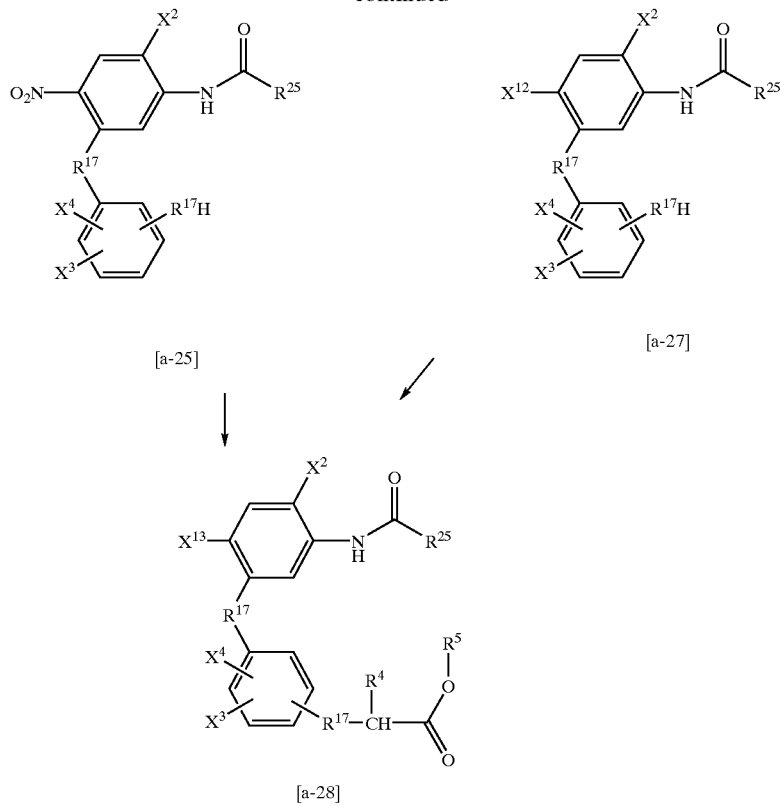

[a-25]   [a-27]

[a-28]

Wherein, $R^4$, $R^5$, $R^7$, $R^{17}$, $X^2$, $X^3$, $X^4$, $X^{12}$ and $X^{13}$ are the same as defined above, $R^{25}$ represents $C_1$ to $C_6$ alkyl which may be substituted such as methyl, ethyl, trifluoromethyl, trichloromethyl and the like: or $C_1$ to $C_6$ alkoxy which may be substituted such as methoxy, ethoxy and the like: or phenoxy which may be substituted such as phenoxy and the like.

<Process A13-1>: A process for producing the compound [a-25] from the compound [a-24]

The compound [a-25] can be produced by reacting the compound [a-24] with the compound [b-2] in the presence of a base.

This reaction is conducted usually in the absence of a solvent or in a solvent, and the reaction temperature is usually from 0 to 200° C., and the reaction time is usually from an instant to 24 hours.

Regarding the amounts of reagents to be used in the reaction, it is theoretical that the amount of the compound [b-2] is 1 mol and the amount of the base is 1 mol based on 1 mol of the compound [a-24], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, sodium hydroxide, potassium hydroxide, calcium hydroxide, barium hydroxide and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

This reaction may sometimes be accelerated by using a catalyst. As the catalyst, copper iodide, copper bromide, copper chloride, copper powder and the like are listed, and the amount of the catalyst used in the reaction is from 0.0001 to 0.1 mol based on 1 mol of the compound [a-24], and the amounts thereof can be changed optionally depending on the reaction condition.

After completion of the reaction, an intended material can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the intended material can also be purified by a procedure such as chromatography, re-crystallization and the like.

<Process A13-2>: A process for producing the compound [a-26] from the compound [a-25]

The compound [a-26] can be produced, for example, by reducing the compound [a-25] using an iron powder in the presence of an acid in a solvent.

The reaction temperature of this reaction is usually from 0 to 200° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [a-25], and the amounts thereof can be changed optionally depending on the reaction condition.

As the acid to be used, acetic acid and the like are listed.

As the solvent to be used, there are listed, for example, water, acetic acid, ethyl acetate and the like or mixtures thereof.

After completion of the reaction, an intended material can be obtained by usual post-treatment such as by pouring a reaction solution in to water directly or after filtration and collecting the produced crystals by filtration, or, extracting with an organic solvent, neutralization, drying, concentration and the like.

The intended material can also be purified by a procedure such as chromatography, re-crystallization and the like.

<Process A13-3>: A process for producing the compound [a-27] from the compound [a-26]

The compound [a-27] can be produced by i) diazotizing the compound [a-26] in a solvent, then, ii) subsequently, reacting the diazo compound with potassium iodide, copper (I) bromide, copper (I) chloride or hydroborofluoric acid in a solvent.

In the diazotization reaction of the first step, the reaction temperature is from −20 to 20° C., and the reaction time is usually from an instant to 5 hours.

Regarding the amounts of reagents to be used in the reaction, it is theoretical that the amount of the diazotization agent is 1 mol based on 1 mol of the compound [a-26], and the amounts thereof can be changed optionally depending on the reaction condition.

As the diazotization agent to be used, nitrites such as sodium nitrite, potassium nitrite, isoamyl nitrite, t-butyl nitrite and the like, are listed.

As the solvent, there are listed, for example, acetonitrile, hydrobromic acid, hydrochloric acid, sulfuric acid, water and the like or mixtures thereof.

The reaction solution after completion of the reaction is used as it is in the following reaction.

In the reaction of the second step, the reaction temperature is from 0 to 80° C., and the reaction time is usually from an instant to 24 hours.

Regarding the amounts of reagents to be used in the reaction, each amount of potassium iodide, copper (I) bromide, copper (I) chloride or hydroborofluoric acid is from 1 to 3 mol based on 1 mol of the compound [a-26], and the amounts thereof can be changed optionally depending on the reaction condition. When copper [I] bromide is used, the reaction can also be conducted in the presence of copper (II) bromide, and when copper (I) chloride is used, the reaction can also be conducted in the presence of copper (II) chloride.

As the solvent to be used, there are listed, for example, acetonitrile, diethyl ether, t-butyl methyl ether, hydrobromic acid, hydrochloric acid, sulfuric acid, water and the like or mixtures thereof.

After completion of the reaction, an intended material can be obtained by usual post-treatment such as by collecting the produced crystals by filtration (if necessary, by adding water), or, extracting with an organic solvent, concentration and the like.

The intended material can also be purified by a procedure such as chromatography, re-crystallization and the like.

Further, this reaction is not limited to the above-mentioned methods, and production can also be conducted by reacting the compound [a-26] with the diazotizing agent in a solvent (for example, acetonitrile, diethyl ether, t-butyl methyl ether, hydrobromic acid, hydrochloric acid, sulfuric acid, water or mixtures thereof) in the presence of potassium iodide, copper (I) bromide, copper (I) chloride or hydroborofluoric acid. When copper [I] bromide is used, the reaction can also be conducted in the presence of copper (II) bromide, and when copper (I) chloride is used, the reaction can also be conducted in the presence of copper (II) chloride.

<Process A13-4>: A process for producing the compound [a-28] from the compound [a-27]

The compound [a-28] can be produced by reacting the compound [a-27] with the compound [IV] in the presence of a base.

This reaction is conducted usually in a solvent, and the reaction temperature is usually from 0 to 200° C., and the reaction time is usually from an instant to 72 hours.

Regarding the amounts of reagents to be used in the reaction, it is theoretical that the amount of the compound [IV] is 1 mol and the amount of the base is 1 mol based on 1 mol of the compound [a-27], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

After completion of the reaction, an intended material can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the intended material can also be purified by a procedure such as chromatography, re-crystallization and the like.

<Process A13-5>: A process for producing the compound [a-28] from the compound [a-25]

The compound [a-28] wherein $X^{13}$ is nitro can be produced by reacting the compound [a-25] with the compound [IV] in the presence of a base.

This reaction is conducted usually in a solvent, and the reaction temperature is usually from 0 to 200° C., and the reaction time is usually from an instant to 72 hours.

Regarding the amounts of reagents to be used in the reaction, it is theoretical that the amount of the compound [IV] is 1 mol and the amount of the base is 1 mol based on 1 mol of the compound [a-25], and the amounts thereof can be changed optionally depending on the reaction condition.

The base to be used includes organic bases such as pyridine, quinoline, benzyldimethylamine, phenetyldimethylamine, N-methylmorpholine, 1,8-diazabicyclo[5.4.0]undec-7-en, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, dichlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl formate, ethyl acetate, butyl acetate, diethyl carbonate and the like; nitriles such as acetonitrile, isobutyronitrile and the like; acid amides such as N,N-dimethylformamide, N,N-dimethylacetamide and the like; sulfur compounds such as dimethyl sulfoxide, sulfolane and the like; or mixtures thereof.

After completion of the reaction, an intended material can be obtained, for example, by the following operation 1) or 2).

1) A reaction solution is poured into water, this is extracted with an organic solvent, and the resulted organic layer is dried and concentrated.

2) A reaction solution is concentrated itself, or, filtrated if necessary before the filtrate is concentrated.

Further, the intended material can also be purified by a procedure such as chromatography, re-crystallization and the like.

(Intermediate Production Method 14)

The compound [III] wherein W is oxygen can also be produced by a method described in the following scheme.

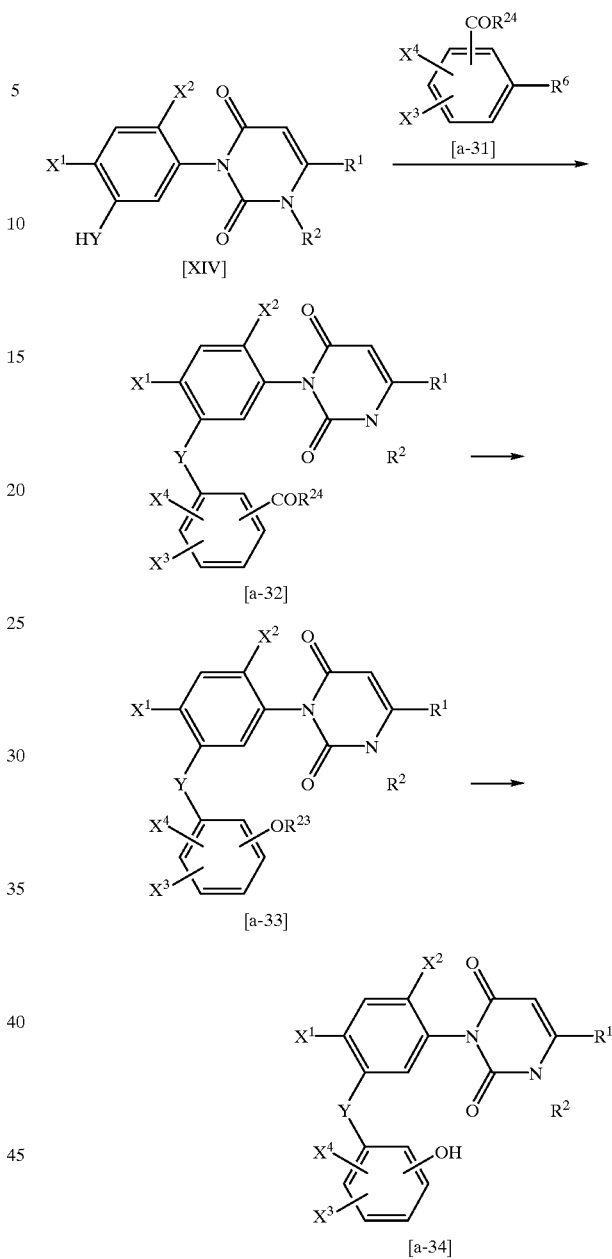

Wherein, $R^1$, $R^2$, $R^6$, $X^1$, $X^2$, $X^3$, $X^4$ and Y are the same as defined above, $R^{23}$ represents formyl, alkylcarbonyl which may be substituted such as acetyl and the like, or alkoxycarbonyl which may be substituted such as methoxycarbonyl and the like, and $R^{24}$ represents hydrogen, alkyl which may be substituted such as methyl and the like, or alkoxy which may be substituted such as methoxy.

(Intermediate Production Method 15)

The compound [III] wherein $X^4$ is hydrogen, fluorine, chlorine, bromine or iodine can also be produced by a method described in the following scheme.

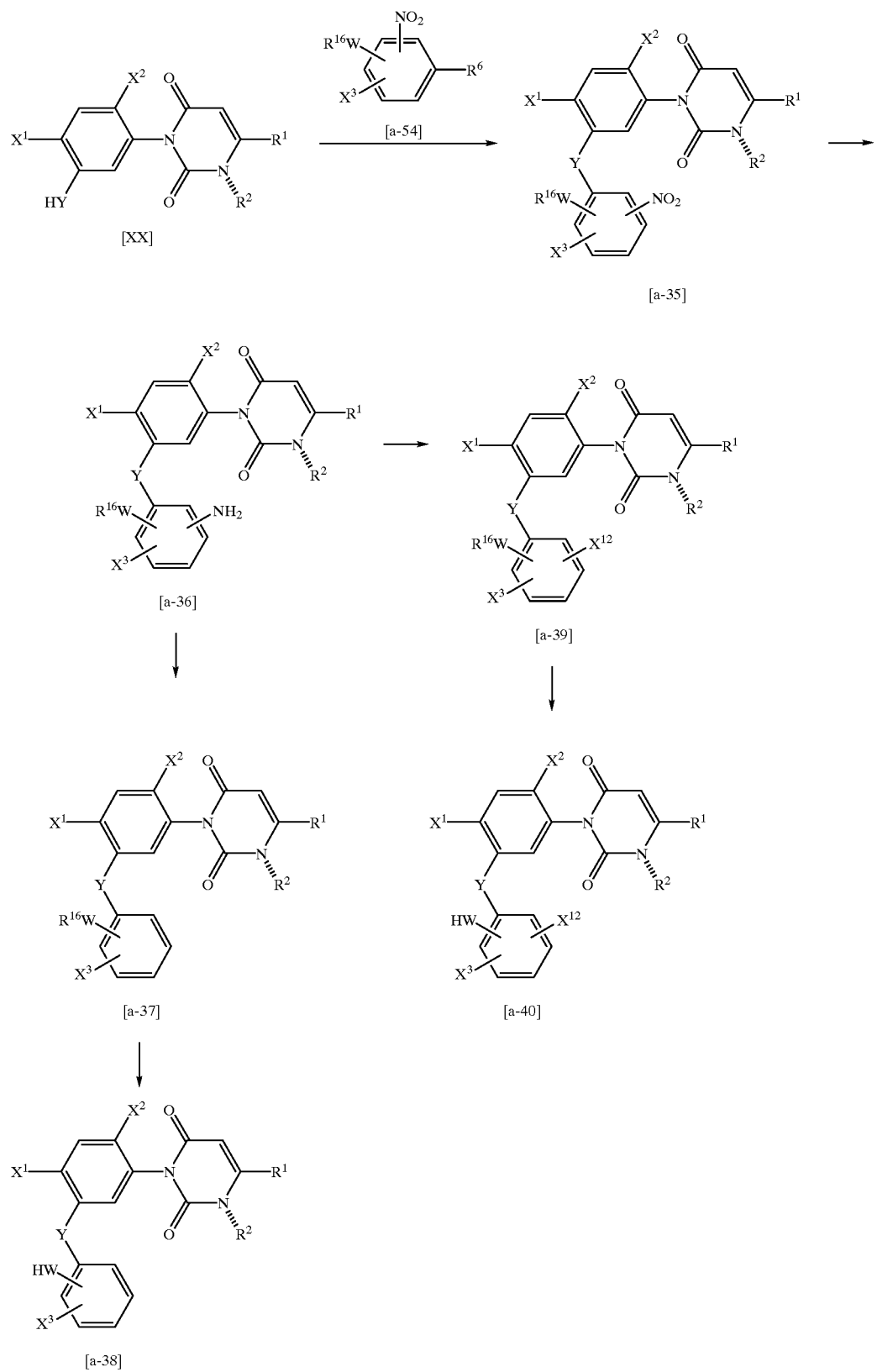

Wherein, $R^1$, $R^2$, $R^6$, $R^{16}$, W, $X^1$, $X^2$, $X^3$, $X^{12}$ and Y are the same as defined above.

(Intermediate Production Method 16)

Compounds [a-25] and [a-27] wherein $R^{25}$ is defined as $R^{20}$ can also be produced by a method described in the following scheme.

[a-41]

[a-42]

Wherein, $R^{16}$, $R^{17}$, $R^{20}$, $X^2$, $X^3$, $X^4$ and $X^{13}$ are the same as defined above.

The compound [a-42] can be produced, from the compound [a-41] according to a method described in Protective Groups in Organic Synthesis (published by A Wiley-Interscience publication) using boron tribromide, HBr/acetic acid, conc. hycrochloric acid or conc. sulfuric acid and the like.

Amount of reagent: from 1 mol to excess based on 1 mol of the compound [a-41]

Solvent: aromatic hydrocarbons such as benzene, toluene and the like, halogenated aliphatic hydrocarbons such as methylene chloride, chloroform and the like, halogenated aromatic hydrocarbons such as chlorobenzene and the like, or the mixture thereof.

Reaction Temperature: from −20° C. to reflux temperature

Reaction Time: from an instant to 48 hours

After completion of the reaction, an intended material can be obtained by a post-treatment operation such as by pouring a reaction solution into water or adding an acid such as conc. hydrochloric acid and the like to a reaction solution and collecting the deposited crystals by filtration, or, extracting a reaction solution with an organic solvent and drying and concentrating the organic layer, or, concentrating a reaction solution itself, and the like. This compound can also be purified by an operation such as re-crystallization, chromatography and the like.

In the case of the compound [a-41) wherein $R^{16}$ is benzyl which may be substituted, the compound [a-42] can also be produced from the compound [a-41] by hydrogenation in the presence of a catalyst.

This reaction is usually conducted in a solvent, the reaction temperature is usually from −20 to 150° C., preferably from 0 to 50° C. The reaction time is usually from an instant to 48 hours.

This reaction can also be conducted under pressure, and the reaction is preferably conducted under a pressure of 1 to 5 atom.

The amount of the catalyst used in this reaction is from 0.001 to 100% by weight based on the compound [a-41], As the catalyst to be used in the reaction, anhydrous palladium/carbon, water-containing palladium/carbon, platinum oxide and the like are listed.

The solvent includes carboxylic acids such as formic acid, acetic acid, propionic acid and the like, esters such as ethyl formate, ethyl acetate, butyl acetate, diethyl carbonate and the like; ethers such as 1,4-dioxane, tetrahydrofuran, ethylene glycol dimethyl ether and the like; alcohols such as methanol, ethanol, propanol, isopropanol, butanol, t-butanol, amyl alcohol, isoamyl alcohol, t-amyl alcohol and the like; water, or mixtures thereof and the like.

After completion of the reaction, an intended material can be obtained by a usual post-treatment operation such as by filtrating a reaction solution before concentrating the solution itself, and the like. The intended material can also be purified by a procedure such as chromatography, re-crystallization and the like.

The compound [XXXXII] can be produced, for example, by a method described in WO98/08824 or a method according to the method described in this publication, and the compound [XXXXI], the compound [XXI], the compound [XXIV], the compound [XX] and the compound [XXV] can be produced by known methods or commercially available products can be used.

The present compounds have excellent herbicidal activity and some of them can exhibit excellent selectivity between crops and weeds. In other words, the present compounds have herbicidal activity against various weeds which may cause some trouble in the foliar treatment and soil treatment on upland fields, such as listed below.

Onagraceous weeds::
large-flowered eveningprimrose (*Oenothera erythrosepala*), cutleaf eveningprimrose (*Oenothera laciniata*),
Ranunculaceous weeds:
roughseeded buttercup (*Ranunculus muricatus*), hairy buttercup (*Ranunculus sardous*)
Polygonaceous weeds:
wild buckwheat (*Polygonum convolvulus*), pale smartweed (*Polygonum lapathiolium*), Pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)
Portulacaceous weeds:
common purslane (*Portulaca oleracea*)
Caryophyllaceous weeds:
common chickweed (*Stellaria media*), sticky chickweed (*Cerastium glomeratum*)
Chenopodiaceous weeds:
common lambsquarters (*Chenopodium album*), kochia (*Kochia scoparia*)
Amaranthaceous weeds:
redroot pigweed (*Amaranthus retroflexus*), smooth pigweed (*Amaranthus hybridus*)
Cruciferous (brassicaceous) weeds:
wild radish (*Raphanus raphanistrum*), wild mustard (*Sinapis arvensis*), shepherdpurse (*Capsella bursa-pastoris*), virginia pepperweed (*Lepidium virginicum*)
Leguminous (fabaceous) weeds:
hemp sesbania (*Sesbania exaltata*), sicklepod (*Cassia obtusifolia*), Florida beggarweed (*Desmodium tortuosum*), white clover (*Trifolium repens*), common vetch (*Vicia sativa*), black medik (*Medicago lupulina*)

Malvaceous weeds:
velvetleaf (*Abutilon theophrasti*), prickly sida (*Sida spinosa*)
Violaceous weeds:
field pansy (*Viola arvensis*), wild pansy (*Viola tricolor*)
Rubiaceous weeds:
catchweed bedstraw (cleavers) (*Galium aparine*)
Convolvulaceous weeds:
ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)
Labiate weeds:
red deadnettle (*Lamium purpureum*), henbit (*Lamium amplexicaule*)
Solanaceous weeds:
jimsonweed (*Datura stramonium*), black nightshade (*Solanum nigrum*)
Scrophulariaceous weeds:
birdseye speedwell (*Veronica persica*), corn speedwell (*Veronica arvensis*), ivyleaf speedwell (*Veronica hederaefolia*)
Composite weeds:
common cocklebur (*Xanthium pensylvanicum*), common sunflower (*Helianthus annuus*), wild camomille (*Matricaria chamomilla*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*), common dandelion (*Taraxacum officinale*)
Boraginaceous weeds:
forget-me-not (*Myosotis arvensis*)
Asclepiadaceous weeds:
common milkweed (*Asclepias syriaca*)
Euphorbiaceous weeds:
sun spurge (*Euphorbia helioscopia*), spotted spurge (*Euphorbia maculata*)
Geraniaceous weeds:
Carolina geranium (*Geranium carolinianum*)
Oxalidaceous weeds:
pink woodsorrel (*Oxalis corymbosa*)
Cucurbitaceous weeds:
burcucumber (*Sicyos angulatus*)
Graminaceous weeds:
barnyardgrass (*Echinochloa crus-galli*), green foxtail (*Setaria viridis*), giant foxtail (*Setaria faberi*), large crabgrass (*Digitaria sanguinalis*), Southern Crabgrass (*Digitaria ciliaris*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*), water foxtail (*Alopecurus geniculatus*)
Commelinaceous weeds:
common dayflower (*Commelina communis*)
Equisetaceous weeds:
field horsetail (*Equisetum arvense*)
Cyperaceous weeds:
rice flatsedge (*Cyperus iria*), purple nutsedge (*Cyperus rotundus*), yellow nutsedge (*Cyperus esculentus*)

Furthermore, some of the present compounds exhibit no significant phytotoxicity on the main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*), and canola (*Brassica napus*); horticultural crops such as flowers and ornamental plants; and vegetable crops. The present compounds can also attain the effective control of various weeds which may cause some trouble in the no-tillage cultivation of soybean (*Glycine max*), corn (*Zea mays*), wheat (*Triticum aestivum*), and other crops. Furthermore, some of the present compounds exhibit no significant phytotoxicity on the crops.

The present compounds also have herbicidal activity against various weeds which may cause some trouble in the flooding treatment on paddy fields, such as listed below.
Graminaceous weeds:
barnyardgrass (*Echinochloa oryzicola*)
Scrophulariaceous weeds:
common falsepimpernel (*Lindernia procumbens*)
Lythraceous weeds:
Indian toothcup (*Rotala indica*), red stem (*Ammannia multiflora*)
Elatinaceous weeds:
waterwort (*Elatine triandra*)
Cyperaceous weeds:
smallflower umbrella sedge (*Cyperus difformis*), hardstem bulrush (*Scirpus juncoides*), needle spikerush (*Eleocharis acicularis*), water nutgrass (*Cyperus serotinus*), water chestnut (*Eleocharis kuroguwai*)
Pontederiaceous weeds:
monochoria (*Monochoria vaginalis*)
Alismataceous weeds:
arrowhead (*Sagittaria pygmaea*), arrowhead (*Sagittaria trifolia*), waterplantain (*Alisma canaliculatum*)
Potamogetonaceous weeds:
roundleaf pondweed (*Potamogeton distinctus*)
Potamogetonaceous weeds:
roundleaf pondweed (*Potamogeton distinctus*)
Umbelliferous weeds:
watercelery sp. (*Oenanthe javanica*)

Furthermore, some of the present compounds exhibit no significant phytotoxicity on transplanted paddy rice.

The present compounds can also attain the control of a wide variety of weeds which are growing or will grow in the orchards, grasslands, lawns, forests, waterways, canals, or other non-cultivated lands in which weed controlling is necessiated such as levee, riverbed, roadside, railroad, green field of park, ground, parking, airport, industrial place (ex. factory, storage equipement), fallow land, vacant lot, and the like. The present compounds also have herbicidal activity against various aquatic weeds, such as water hyacinth (*Eichhornia crassipes*), which are growing or will grow at the waterside such as rivers, canals, waterways or reservoir.

The present compounds have substantially the same characteristics as those of the herbicidal compounds disclosed in the published specification of International Patent Application, WO95/34659. In the case where crops with tolerance imparted by introducing a herbicide tolerance gene described in the published specification are cultivated, the present compounds can be used at larger rates than those used when ordinary crops without tolerance are cultivated, which makes it possible to control other unfavorable weeds more effectively.

When the present compounds are used as the active ingredients of herbicides, they are usually mixed with solid or liquid carriers or diluents, surfactants, and other auxiliary agents to give emulsifiable concentrates, wettable powders, flowables, granules, concentrated emulsions, water-dispersible granules, or other formulations These formulations may contain any of the present compounds as an active ingredient at an amount of 0.001 to 80% by weight, preferably 0.005 to 70% by weight, based on the total weight of the formulation.

The solid carrier or diluent which can be used may include, for example, fine powders or granules of the following materials: mineral matters such as kaolin clay, attapulgite clay, bentonite, acid clay, pyrophyllite, talc, diatomaceous earth, and calcite; organic substances such as walnut shell powder; water-soluble organic substances such as urea; inorganic salts such as ammonium sulfate; and synthetic hydrated silicon oxide. The liquid carrier or diluent which can be used may include, for example, aromatic hydrocarbons such as methylnaphthalene, phenylxylylethane, and alkylbenzene (e.g., xylene); alcohols such as isopropanol, ethylene glycol, and 2-ethoxyethanol; esters such as phthalic acid dialkyl esters; ketones such as acetone, cyclohexanone, and isophorone; mineral oils such as machine oil; vegetable oils such as soybean oil and cottonseed oil; dimethyl sulfoxide, N,N-dimethylformamide, acetonitrile, N-methylpyrrolidone, and water.

The surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters, and polyoxyethylene sorbitan fatty acid esters.

The auxiliary agent may include lignin sulfonates, alginates, polyvinyl alcohol, gum arabic, CMC (carboxymethylcellulose), and PAP (isopropyl acid phosphate).

The present compounds are usually formulated as described above and then used for pre- or post-emergence soil, foliar, or flooding treatment of weeds. The soil treatment may include soil surface treatment and soil incorporation. The foliar treatment may include application over the plants and directed application in which a chemical is applied only to weeds so as to keep off the crop plants.

The present compounds may often exhibit the enhancement of herbicidal activity when used in admixture with other herbicides. They can also be used in admixture with insecticides, acaricides, nematocides, fungicides, bactericides, plant growth regulators, fertilizers, and soil conditioners.

Examples of the herbicide which can be used in admixture with the present compounds are atrazine, cyanazine, dimethametryn, metribuzin, prometryn, simazine, simetryn, chlorotoluron, diuron, fluometuron, isoproturon, linuron, methabenzthiazuron, propanil, bentazone, bromoxynil, ioxynil, pyridate, butamifos, dithiopyr, ethalfluralin, pendimethalin, thiazopyr, trifluralin, acetochlor, alachlor, butachlor, diethatyl-ethyl, dimethenamid, fluthiamide, mefenacet, metolachlor, pretilachlor, propachlor, cinmethylin, acifluorfen, acifluorfen-sodium, benzfendizone, bifenox, butafenacil, chlomethoxynil, fomesafen, lactofen, oxadiazon, oxadiargyl, oxyfluorfen, carfentrazone-ethyl, fluazolate, flumiclorac-pentyl, flumioxazine, fluthiacet-methyl, isopropazol, sulfentrazone, thidiazimin, azafenidin, pyraflufen-ethyl, cinidon-ethyl, difenzoquat, diquat, paraquat, 2,4-D, 2,4-DB, clopyralid, dicamba, fluroxypyr, MCPA, MCPB, mecoprop, quinclorac, triclopyr, azimsulfuron, bensulfuron-methyl, chlorimuron-ethyl, chlorsulfuron, cloransulam-methyl, cyclosulfamuron, diclosulam, ethoxysulfuron, flazasulfuron, flucarbazone, flumetsulam, flupyrsulfuron, halosulfuron-methyl, imazosulfuron, indosulfuron, metosulam, metsulfuron-methyl, nicosulfuron, oxasulfuron, primisulfuron-methyl, procarbazone-sodium, prosulfuron, pyrazosulfuron-ethyl, rimsulfuron, sulfometuron-methyl, sulfosulfuron, triasulfuron, tribenuron-methyl, tritosulfuron, thifensulfuron-methyl, triflusulfuron-methyl, pyribenzoxim, bispyribac-sodium, pyriminobac-methyl, pyrithiobac-sodium, imazameth, imazamethabenz-methyl, imazamox, imazapic, imazapyr, imazaquin, imazethapyr, tepraloxydim, alloxydim-sodium, clethodim, clodinafop-propargyl, dihalofop-butyl, dichlofop-methyl, fenoxaprop-ethyl, fenoxaprop-p-ethyl, fluazifop-buthyl, fluazifop-p-butyl, haloxyfop-methyl, quizalofop-p-ethyl, sethoxydim, tralkoxydim, diflufenican, flurtamone, norflurazone, benzofenap, isoxaflutole, pyrazolate, pyrazoxyfen, sulcotrione, clomazone, mesotrione, isoxachlortole, bialaphos, glufosinate-ammonium, glyphosate, sulfosate, dichlobenil, isoxaben, benthiocarb, butylate, dimepiperate, EPTC, esprocarb, molinate, pyributicarb, triallate, bromobutide, DSMA, MSMA, cafenstrol, daimron, epoprodan, flupoxam, metobenzuron, pentoxazone, piperophos, triaziflam, beflubutamid, benzobicyclon, clomeprop, fentrazamide, flufenacet, florasulam, indanofan, isoxadifen, mesotrione, naploanilide, oxaziclomefone, pethoxyamid, phnothiol, pyridafol.

The above compounds are described in the catalog of Farm Chemicals Handbook, 1995 (Meister Publishing Company); AG CHEM NEW COMPOUND REVIEW, VOL. 13, 1995, VOL. 15, 1997, VOL. 16, 1998 or, VOL. 17, 1999 (AG CHEM INFORMATION SERVICES); or Josouzai Kenkyu Souran (Hakuyu-sha).

When the present compounds are used as the active ingredients of herbicides, the application amount, although it may vary with the weather conditions, formulation types, application times, application methods, soil conditions, crops to be protected, weeds to be controlled, and other factors, is usually in the range of 0.01 to 20,000 g, preferably 1 to 12,000 g, per hectare. In the case of emulsifiable concentrates, wettable powders, flowables, concentrated emulsions, water-dispersible granules, or other similar formulations, they are usually applied after diluted in their prescribed amounts with water (if necessary, containing an adjuvant such as a spreading agent) at a ratio of 10 to 1000 liters per hectare. In the case of granules or some types of flowables, they are usually applied as such without any dilution.

The adjuvant which can be used, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed oil, and sunflower oil.

The present compounds can also be used as the active ingredients of harvesting aids such as defoliants and desiccants for cotton (Gossipyum spp.), and desiccants for potato (*Solanum tuberosum*). In these cases, the present compounds are usually formulated in the same manner as the case where they are used as the active ingredients of herbicides, and used alone or in admixture with other harvesting aids for foliar treatment before the harvesting of crops.

The following production examples, formulation examples and test examples and the like will illustrate the present invention further in detail below, but do not limit the scope of the invention.

First, production examples of present compounds and production examples of intermediates will be shown. The compound numbers of present compounds correspond to numbers described in Tables 1 to 5 described below.

PRODUCTION EXAMPLE 1

Production of Compound 1-1

0.43 g of 4-{2-chloro-4-fluoro-5-[3-methyl-2,6-dioxo-4-(trifluoromethyl)-1,2,3,6-tetrahydropyrimidin-1-yl] phenoxy}phenol (produced in Intermediate Production Example 1) was dissolved in 2.0 ml of N,N-dimethylformamide, and to this was added 0.15 g of anhydrous potassium carbonate, and 0.17 g of methyl 2-bromopropionate was added with stirring at room temperature, then, the mixtures was stirred for 3 hours at 70° C. The reaction solution was cooled to room temperature, then, the reaction solution was poured into ice water, and extracted with ethyl acetate. The organic layer was washed with saturated saline, dried over anhydrous magnesium sulfate, and concentrated. The residues was subjected to silica gel column chromatography to obtain 0.39 g of methyl 2-[4-{2-chloro-4-fluoro-5-[3-methyl-2,6-dioxo-4-(trifluoromethyl)-1,2,3,6-tetrahydropyrimidin-1-yl] phenoxy}phenoxy]propionate [Compound 1-1 of the present invention].

$^1$H-NMR (CDCl$_3$/300 MHz) δ (ppm): 1.61 (d, 3H, J=6.9 Hz), 3.52 (s, 3H), 3.77 (s, 3H), 4.70 (q, 1H, J=6.7 Hz), 6.31 (s, 1H), 6.7 to 6.8 (m, 1H), 6.8 to 6.9 (m, 2H), 6.9 to 7.0 (m, 2H), 7.36 (d, 1H, J=9.0 Hz)

PRODUCTION EXAMPLE 2

Production of Compound 2-1

0.30 g of 3-{2-chloro-4-fluoro-5-[3-methyl-2,6-dioxo-4-(trifluoromethyl)-1,2,3,6-tetrahydropyrimidin-1-yl] phenoxy}phenol (described later, produced in Intermediate Production Example 2) was dissolved in 1.4 ml of N,N-dimethylformamide, and to this was added 0.10 g of anhydrous potassium carbonate, and 0.11 g of methyl 2-bromopropionate was added with stirring at room temperature, then, the mixtures was stirred for 3 hours at 70° C. The reaction solution was cooled to room temperature, then, the reaction solution was poured into ice water, and extracted with ethyl acetate. The organic layer was washed with saturated saline, dried over anhydrous magnesium sulfate, and concentrated. The residues was subjected to silica gel column chromatography to obtain 0.28 g of methyl 2-[3-{2-chloro-4-fluoro-5-[3-methyl-2,6-dioxo-4-(trifluoromethyl)-1,2,3,6-tetrahydropyrimidin-1-yl] phenoxy}phenoxy]propionate [Compound 2-1 of the present invention].

$^1$H-NMR (CDCl$_3$/300 MHz) δ (ppm): 1.60 (d, 3H, J=7.0 Hz), 3.53 (s, 3H), 3.75 (s, 3H), 4.74 (q, 1H, J=6.7 Hz), 6.32 (s, 1H), 6.5 to 6.7 (m, 3H), 6.9 to 7.0 (m, 1H), 7.1 to 7.3 (m, 1H), 7.38 (d, 1H, J=8.9 Hz)

PRODUCTION EXAMPLE 3

Production of Compound 3-1

0.23 g of 2-{2-chloro-4-fluoro-5-[3-methyl-2,6-dioxo-4-(trifluoromethyl)-1,2,3,6-tetrahydropyrimidin-1-yl] phenoxy}phenol was dissolved in 6 ml of N,N-dimethylformamide, and to this was added 0.22 g of anhydrous potassium carbonate, and 0.13 g of methyl 2-bromopropionate was added with stirring at room temperature, then, the mixtures was stirred for 3 hours at 80° C. The reaction solution was cooled to room temperature, then, the reaction solution was poured into ice water, and extracted with ethyl acetate. The organic layer was washed with saturated saline, dried over anhydrous magnesium sulfate, and concentrated. The residues was subjected to silica gel column chromatography to obtain 0.23 g of methyl 2-[2-{2-chloro-4-fluoro-5-[3-methyl-2,6-dioxo-4-(trifluoromethyl)-1,2,3,6-tetrahydropyrimidin-1-yl] phenoxy}phenoxy]propionate [Compound 3-1 of the present invention].

$^1$H-NMR (CDCl$_3$/250 MHz) δ (ppm): 1.47 (d, 3H, J=6.8 Hz), 3.50 (q, 3H, J=0.7 Hz), 3.6 to 3.8 (m, 3H), 4.6 to 4.8 (m, 1H), 6.28 (s, 1H), 6.7 to 6.8 (m, 1H), 6.8 to 6.9 (m, 1H), 6.9 to 7.1 (m, 1H), 7.1 to 7.2 (m, 2H), 7.3 to 7.4 (m, 1H)

Physical values of present compounds produced in the same manner as in Production Example 3 are shown below.

Ethyl 2-[2-{2-chloro-4-fluoro-5-[3-methyl-2,6 dioxo-4-(trifluoromethyl)-1,2,3,6-tetrahydropyrimidin-1-yl] phenoxy}phenoxy]propionate [Compound 3-2 of the present invention]

$^1$H-NMR (CDCl$_3$/250 MHz) δ (ppm): 1.23 (t, 3H, J=7.1 Hz), 1.47 (d, 3H, J=6.8 Hz), 3.50 (s, 3H), 4.1 to 4.3 (m, 2H), 4.6 to 4.8 (m, 1H), 6.3 to 6.4 (m, 1H), 6.7 to 7.0 (m, 3H), 7.0 to 7.2 (m, 2H), 7.3 to 7.4 (m, 1H)

Methyl [2-{2-chloro-4-fluoro-5-[3-methyl-2,6-dioxo-4-(trifluoromethyl)-1,2,3,6-tetrahydropyrimidin-1-yl] phenoxy}phenoxy]acetate [Compound 3-11 of the present invention]

Melting Point: 116.4° C.

Ethyl [2-{2-chloro-4-fluoro-5-[3-methyl-2,6-dioxo-4-(trifluoromethyl)-1,2,3,6-tetrahydropyrimidin-1-yl] phenoxy}phenoxy]acetate [Compound 3-12 of the present invention]

$^1$H-NMR (CDCl$_3$/300 MHz) δ (ppm): 1.26 (t, 3H, J=7.1 Hz), 3.50 (s, 3H), 4.19 (q, 2H, J=7.2 Hz), 4.64 (s, 2H), 6.28 (s, 1H), 6.7 to 6.8 (m, 1H), 6.9 to 7.2 (m, 4H), 7.36 (d, 1H, J=8.8 Hz)

PRODUCTION EXAMPLE 4

Production of Compound 3-189

Process 1:

0.365 g of methyl 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionate (Compound 3-1 of the present invention) was dissolved in 4 ml of 1,4-dioxane, to this was added a mixed solution of 1 ml of conc. hydrochloric acid and 1 ml of water while stirring, then, the mixture was heated for 5 hours and 45 minutes while stirring under reflux condition. Thereafter, the solution was allowed to cool, and ice water was poured into the reaction solution, ethyl acetate and saturated saline were added to the solution which was separated subsequently, and aqueous sodium hydrogen carbonate was added to the organic layer before separation, aqueous hydrochloric acid was added to the aqueous layer to acidify it, then, ethyl acetate was added before separation, the organic layer was washed with saturated saline, and dried over magnesium sulfate, then, concentrated to obtain 0.183 g of 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionic acid.

$^1$H-NMR (CDCl$_3$/250 MHz) δ (ppm): 1.53 (d, 3H, J=6.9 Hz), 3.51 (s, 3H), 4.76 to 4.83 (m, 1H), 6.32 (d, 1H, J=3.5 Hz), 6.63 to 6.67 (m, 1H), 7.0 to 7.1 (m, 2H), 7.1 to 7.2 (m, 2H), 7.38 (d, 1H, J=9.0 Hz)

Process 2:

2-[2-{2-chloro-4-fluoro-5-[3-methyl-2,6-dioxo-4-(trifluoromethyl)-1,2,3,6-tetrahydropyrimidin-1-yl] phenoxy}phenoxy]propionic acid is dissolved in tetrahydrofuran, to this is added thionyl chloride while stirring, then, the mixture is heated while stirring under reflux condition. Then, the solution is allowed to cool, concentrated, then, dissolved in tetrahydrofuran (hereinafter, referred to as Solution A). Tetrahydrofuran is added to 1-pentyl alcohol, and Solution A is added to this, then, pyridine is added. The mixture is stirred at room temperature, then, 2% aqueous hydrochloric acid is poured into the reaction solution, and extracted with ethyl acetate. The organic layer is washed with saturated saline, and dried over magnesium sulfate, then, concentrated. The residue is subjected to silica gel column chromatography (eluent: hexane/ethyl acetate=5/1) to obtain pentyl 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionate [compound 3-189 of the present invention].

PRODUCTION EXAMPLE 5

Production of Compound 3-20

Process 1:

0.4 g of methyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate [Compound 3-11 of the present invention] was dissolved in 4 ml of 1,4-dioxane, to this was added a mixed solution of 1 ml of conc. hydrochloric acid and 1 ml of water while stirring, then, the mixture was heated for 12 hours while stirring under reflux condition. Thereafter, the solution was allowed to cool, and ice water was poured into the reaction solution, ethyl acetate and saturated saline were added to the solution which was separated subsequently, and aqueous sodium hydrogen carbonate was added to the organic layer before separation, aqueous hydrochloric acid was added to the aqueous layer to acidify it, then, ethyl acetate was added before separation, the organic layer was washed with saturated saline, and dried over magnesium sulfate, then, concentrated to obtain 0.252 g of [2-{2-chloro-4-fluoro-5-[3-methyl-2,6-dioxo-4-(trifluoromethyl)-1,2,3,6-tetrahydropyrimidin-1-yl]phenoxy}phenoxy]acetic acid.

$^1$H-NMR (CDCl$_3$/250 MHz) δ (ppm): 3.50 (d, 3H, J=1.2 Hz), 4.66 (s, 2H), 6.31 (s, 1H), 6.69 (d, 1H, J=6.5 Hz), 6.98 to 7.20 (m, 4H), 7.38 (d, 1H, J=8.8 Hz)

Process 2:

1.0 g of [2-{2-chloro-4-fluoro-5-[3-methyl-2,6-dioxo-4-(trifluoromethyl)-1,2,3,6-tetrahydropyrimidin-1-yl]phenoxy}phenoxy]acetic acid was dissolved in tetrahydrofuran, to this was added 0.7 ml of thionyl chloride while stirring, then, the mixture was heated while stirring under reflux condition for 2 hours. Then, the solution was allowed to cool, concentrated, then, dissolved in 3 ml of tetrahydrofuran (hereinafter, referred to as Solution B). 0.7 ml of tetrahydrofuran was added to 0.05 g of allyl alcohol, and trisected portions of Solution B were added, then, 0.17 ml of pyridine was added. The mixture was stirred for 2 hours at room temperature, then, 2% aqueous hydrochloric acid was poured into the reaction solution, and extracted with ethyl acetate. The organic layer was washed with saturated saline, and dried over magnesium sulfate, then, concentrated. The residue was subjected to silica gel column chromatography (eluent: hexane/ethyl acetate=5/1) to obtain 0.08 g of allyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate [compound 3-20 of the present invention].

$^1$H-NMR (CDCl$_3$/300 MHz) δ (ppm): 3.50 (d, 3H, J=1.2 Hz), 4.62 to 4.64 (m, 2H), 4.68 (s, 2H), 5.22 to 5.32 (m, 2H), 5.8 to 6.0 (m, 1H), 6.28 (s, 1H), 6.76 (d, 1H, J=6.5 Hz), 6.91 to 7.14 (m, 4H), 7.35 (d, 1H, J=8.6 Hz)

PRODUCTION EXAMPLE 6

Production of Compound 3-16

0.20 g of 2-{2-chloro-4-fluoro-5-[3-methyl-2,6-dioxo-4-(trifluoromethyl)-1,2,3,6-tetrahydropyrimidin-1-yl]phenoxy}phenol was dissolved in 2 ml of N,N-dimethylformamide, to this was added 0.083 g of potassium carbonate, and the mixture was stirred at room temperature for 50 minutes. To this was added 0.077 g of t-butyl chloroacetate, and the mixture was stirred for 2 hours at 40 to 60° C. After allowing to cool, ice water was poured into the reaction solution, ethyl acetate and saturated saline were added before separation. The organic layer was washed with saturated saline, dried over magnesium sulfate and concentrated. The residue was subjected to silica gel column chromatography (eluent: n-hexane/ethyl acetate=6/1) to obtain 0.39 g of t-butyl 2-{2-chloro-4-fluoro-5-[3-methyl-2,6-dioxo-4-(trifluoromethyl)-1,2,3,6-tetrahydropyrimidin-1-yl]phenoxy}phenoxy]acetate [compound 3-16 of the present invention].

$^1$H-NMR (CDCl$_3$/250 MHz) δ (ppm): 1.44 (s, 9H), 3.49 (d, 3H, J=1.1 Hz), 4.53 (s, 2H), 6.27 (s, 1H), 6.80 (d, 1H, J=6.6 Hz), 6.8 to 7.2 (m, 4H), 7.35 (d, 1H, J=8.9 Hz)

Melting Point: 55.6° C.

PRODUCTION EXAMPLE 7

Production of Compound 3-198

1.5 g of [2-{2-chloro-4-fluoro-5-[3-methyl-2,6-dioxo-4-(trifluoromethyl)-1,2,3,6-tetrahydropyrimidin-1 -yl]phenoxy}phenoxy]acetic acid was dissolved in 6 ml of tetrahydrofuran, to this was added 1 ml of thionyl chloride while stirring, and the mixture was stirred for 2 hours and 10 minutes under reflux condition. Then, the solution was allowed to cool, concentrated, then, dissolved in 3 ml of tetrahydrofuran (hereinafter, referred to as Solution C). 1 ml of tetrahydrofuran was added to 0.273 g of isobutyl alcohol, and trisected portions of Solution C were added, then, 0.25 ml of pyridine was added. Thereafter, the mixture was stirred for 2 hours at room temperature, then, 2% aqueous hydrochloric acid was poured into the reaction solution, and ethyl acetate was added before separation, the organic layer was washed with saturated saline, and dried over magnesium sulfate, then, concentrated. The residue was subjected to silica gel column chromatography (eluent: hexane/ethyl acetate=6/1) to obtain 0.34 g of isobutyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate [compound 3-198 of the present invention].

$^1$H-NMR (CDCl$_3$/250 MHz) δ (ppm): 0.89 (d, 6H, J=6.7 Hz), 1.8 to 2.0 (m, 1H), 3.50 (d, 3H, J=1.2 Hz), 3.92 (d, 2H, J=6.7 Hz), 4.67 (s, 2H), 6.28 (s, 1H), 6.77 (d, 1H, J=6.6 Hz), 6.85 to 7.15 (m, 4H), 7.36 (d, 1H, J=8.9 Hz)

PRODUCTION EXAMPLE 8

Production of Compound 3-11

To 0.93 g of methyl [2-{2-chloro-5-[2,6-dioxo-4-(trifluoromethyl)-1,2,3,6-tetrahydropyrimidin-1-yl]-4-fluorophenoxy}phenoxy]acetate, were added 10 ml of N,N-dimethylformamide and 0.31 g of potassium carbonate, then, 0.58 g of methyl iodide was added to the reaction solution, and the mixture was stirred at room temperature for 2 hours. 50 ml of diluted hydrochloric acid was added to the reaction solution and extracted with ethyl acetate. The organic layer was washed with water and then saturated saline, dried over anhydrous sodium sulfate, and concentrated under reduced pressure. The residue was subjected to silica gel column chromatography to obtain 0.82 g of methyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate [Compound 3-11 of the present invention].

$^1$H-NMR (CDCl$_3$/250 MHz) δ (ppm) 3.49–3.50 (m, 3H), 3.73 (s, 3H), 4.66(s, 2H), 6.28 (s, 1H), 6.76 (d, 1H, J=6.6 Hz), 6.9–7.2 (m, 4H), 7.36 (d, 1H, J=8.9 Hz)

PRODUCTION EXAMPLE 9
Production of Compound 3-12

To ethyl [2-{2-chloro-4-fluoro-5-[2,6-dioxo-4-(trifluoromethyl)-1,2,3,6-tetrahydropyrimidin-1-yl]phenoxy}phenoxy]acetate, are added N,N-dimethylformamide and potassium carbonate, then, methyl iodide is added to the reaction solution, and the mixture is stirred at room temperature. Diluted hydrochloric acid is added to the reaction solution and extracted with ethyl acetate. The organic layer is washed with water and then saturated saline, and dried over anhydrous magnesium sulfate, and concentrated. The residue is subjected to silica gel column chromatography to obtain ethyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate [compound 3-12 of the present invention].

PRODUCTION EXAMPLE 10
Production of Compound 1-2

100 mg of 4-{2-chloro-4-fluoro-5-[3-methyl-2,6-dioxo-4-(trifluoromethyl)-1,2,3,6-tetrahydropyrimidin-1-yl]phenoxy}phenol (produced in Intermediate Production Example 1) was dissolved in 1.0 ml of N,N-dimethylformamide, and to this was added 42 mg of anhydrous potassium carbonate, and 46 mg of ethyl 2-bromopropionate was added with stirring at room temperature, then, the mixtures was stirred for 2 hours at 60° C. The reaction solution was cooled to room temperature, then, the reaction solution was poured into ice water, and extracted with ethyl acetate. The organic layer was washed with saturated saline, dried over anhydrous magnesium sulfate, and concentrated. The residue was subjected to silica gel column chromatography to obtain 85 mg of ethyl 2-[4-{2-chloro-4-fluoro-5-[3-methyl-2,6-dioxo-4-(trifluoromethyl)-1,2,3,6-tetrahydropyrimidin-1-yl]phenoxy}phenoxy]propionate [Compound 1-2 of the present invention].

$^1$H-NMR (CDCl$_3$/300 MHz) δ (ppm): 1.27 (t, 3H, J=7.0 Hz), 1.60 (d, 3H, J=6.9 Hz), 3.52 (s, 3H), 4.23 (q, 2H, J=7.0 Hz), 4.68 (q, 1H, J=6.9 Hz), 6.31 (s, 1H), 6.7–6.8 (m, 1H), 6.8–6.9 (m, 2H), 6.9–7.0 (m, 2H), 7.37 (d, 1H, J=8.9 Hz)

PRODUCTION EXAMPLE 11
Production of Compound 1-11

150 mg of 4-{2-chloro-4-fluoro-5-[3-methyl-2,6-dioxo-4-(trifluoromethyl)-1,2,3,6-tetrahydropyrimidin-1-yl]phenoxy}phenol (described later, produced in Intermediate Production Example 1) was dissolved in 1.0 ml of N,N-dimethylformamide, and to this was added 51 mg of anhydrous potassium carbonate, and 50 mg of methyl bromoacetate was added with stirring at room temperature, then, the mixtures was stirred for 2 hours at 60° C. The reaction solution was cooled to room temperature, then, the reaction solution was poured into ice water, and extracted with ethyl acetate. The organic layer was washed with saturated saline, dried over anhydrous magnesium sulfate, and concentrated. The residue was subjected to silica gel column chromatography to obtain 167 mg of methyl [4-{2-chloro-4-fluoro-5-[3-methyl-2,6-dioxo-4-(trifluoromethyl)-1,2,3,6-tetrahydropyrimidin-1-yl]phenoxy}phenoxy]acetate [Compound 1-11 of the present invention].

$^1$H-NMR (CDCl$_3$/250 MHz) δ (ppm): 3.52 (q, 3H, J=1.1 Hz), 3.81 (s, 3H), 4.62 (s, 2H), 6.32 (s, 1H), 6.74 (d, 1H, J=6.6 Hz), 6.8–6.9 (m, 1H), 6.9–7.0 (m, 2H), 7.37 (d, 1H, J=8.9 Hz)

PRODUCTION EXAMPLE 12
Production of Compound 2-11

100 mg of 3-{2-chloro-4-fluoro-5-[3-methyl-2,6-dioxo-4-(trifluoromethyl)-1,2,3,6-tetrahydropyrimidin-1-yl]phenoxy}phenol (described later, produced in Intermediate Production Example 2) was dissolved in 1 ml of N,N-dimethylformamide, and to this was added 34 mg of anhydrous potassium carbonate, and 37 mg of methyl bromoacetate was added with stirring at room temperature, then, the mixtures was stirred for 1 hours at 60° C. The reaction solution was cooled to room temperature, then, the reaction solution was poured into ice water, and extracted with ethyl acetate. The organic layer was washed with saturated saline, dried over anhydrous magnesium sulfate, and concentrated. The residue was subjected to silica gel column chromatography to obtain 110 mg of methyl [3-{2-chloro-4-fluoro-5-[3-methyl-2,6-dioxo-4-(trifluoromethyl)-1,2,3,6-tetrahydropyrimidin-1-yl]phenoxy}phenoxy]acetate [Compound 2-11 of the present invention].

$^1$H-NMR (CDCl$_3$/300 MHz) δ (ppm): 3.53 (q, 3H, J=0.9 Hz), 3.80 (s, 3H), 4.61 (s, 2H), 6.32 (s, 1H), 6.60 (s, 1H), 6.6–6.7 (m, 2H), 6.92 (d, 1H, J=6.6 Hz), 7.23 (d, 1H, J=7.9 Hz), 7.39 (d, 1H, J=9.0 Hz)

PRODUCTION EXAMPLE 13
Production of Compound 5-7

72 mg of 3-{2-cyano-4-fluoro-5-[3-methyl-2,6-dioxo-4-(trifluoromethyl)-1,2,3,6-tetrahydropyrimidin-1 -yl]phenoxy}phenol (described later, produced in Intermediate Production Example 9) was dissolved in 1.0 ml of N,N-dimethylformamide, and to this was added 31 mg of anhydrous potassium carbonate, and 31 mg of methyl 2-bromopropionate was added with stirring at room temperature, then, the mixtures was stirred for 1 hours at 70° C. The reaction solution was cooled to room temperature, then, the reaction solution was poured into water, and extracted with ethyl acetate. The organic layer was washed with saturated saline, dried over anhydrous magnesium sulfate, and concentrated. The residue was subjected to silica gel column chromatography to obtain 80 mg of methyl 2-[3-{2-cyano-4-fluoro-5-[3-methyl-2,6-dioxo-4-(trifluoromethyl)-1,2,3,6-tetrahydropyrimidin-1-yl]phenoxy}phenoxy]propionate [Compound 5-7 of the present invention].

$^1$H-NMR (CDCl$_3$/250 MHz) δ (ppm): 1.62 (d, 3H, J=6.8 Hz), 3.53 (q, 3H, J=1.4 Hz), 3.77 (s, 3H), 4.75 (q, 1H, J=6.8 Hz), 6.3–6.4 (m, 1H), 6.6–6.8 (m, 3H), 6.8–6.9 (m, 1H), 7.2–7.3 (m, 1H), 7.53 (d, 1H, J=8.4 Hz)

PRODUCTION EXAMPLE 14
Production of Compound 5-22

32 mg of 3-{2-cyano-4-fluoro-5-[3-methyl-2,6-dioxo-4-(trifluoromethyl)-1,2,3,6-tetrahydropyrimidin-1-yl]phenoxy}phenol (described later, produced in Intermediate Production Example 9) was dissolved in 0.5 ml of acetonitrile, and to this 13 mg of methyl bromoacetate and 13 mg of anhydrous potassium carbonate were added, then, the mixtures was stirred for 1.5 hours at 60° C. The reaction solution was cooled to room temperature, then, the reaction solution was subjected to silica gel column chromatography to obtain 26 mg of methyl [3-{2-cyano-4-fluoro-5-[3-methyl-2,6-dioxo-4-(trifluoromethyl)-1,2,3,6-tetrahydropyrimidin-1-yl]phenoxy}phenoxy]acetate [Compound 5-22 of the present invention].

$^1$H-NMR (CDCl$_3$/300 MHz) δ (ppm): 3.53 (q, 3H, J=1.0 Hz), 3.81 (s, 3H), 4.63 (s, 2H), 6.32 (s, 1H), 6.6–6.7 (m, 1H), 6.7–6.8 (m, 2H), 6.85 (d, 1H, J=5.9 Hz), 7.2–7.4 (m, 1H), 7.54 (d, 1H, J=8.4 Hz)

PRODUCTION EXAMPLE 15
Production of Compound 4-19

A mixture of 15.16 g of 2-(methoxycarbonyl)methoxyphenol, 29.23 g of 2,5-difluoro-4-[3-methyl-2,6-dioxo-4-(trifluoromethyl)-1,2,3,6-tetrahydropyrimidin-1-yl]nitrobenzene (produced in Intermediate Production Example 4), 11.5 g of anhydrous potassium carbonate and 160 ml of N,N-dimethylformamide was stirred at room temperature for 30 minutes, and then, stirred at 70° C. for 3 hours. To the mixture, 5 g of 2-(methoxycarbonyl)methoxyphenol was added and stirred for 1 hour. The reaction solution was poured into 2% of aqueous hydrochloric acid solution and extracted with ethyl acetate. The organic layer was washed with saturated saline, dried over anhydrous magnesium sulfate, and concentrated. The residue was subjected to silica gel column chromatography to obtain 17.8 g of 2-{2-(methoxycarbonyl)methoxyphenoxy}-5-fluoro-4-[3-methyl-2,6-dioxo-4-(trifluoromethyl)-1,2,3,6-tetrahydropyrimidin-1-yl]nitrobenzene [Compound 4-19 of the present invention].

$^1$H-NMR (CDCl$_3$/300 MHz) δ (ppm): 3.50 (q, 3H, J=1.0 Hz), 3.70 (s, 3H), 4.63 (s, 2H), 6.28 (s, 1H), 6.88 (d, 1H, J=8.4 Hz), 6.93 (d, 1H, J=6.0 Hz), 7.0–7.1 (m, 1H), 7.1–7.3 (m, 2H), 7.87 (d, 1H, J=8.7 Hz)

PRODUCTION EXAMPLE 16
Production of Compound 3-11 of the Present Invention

A mixture of 11.02 g of isoamyl nitrite and 45 ml of acetonitrile was added dropwise to a mixture of 15.16 g of 5-fluoro-2-{2-(methoxycarbonyl)methoxyphenoxy}-4-[3-methyl-2,6-dioxo-4-(trifluoromethyl)-1,2,3,6-tetrahydropyrimidin-1-yl]aniline (produced in Intermediate Production Example 10), 6.21 g of copper (I) chloride, 12.65 g of copper (II) chloride, and 250 ml of acetonitrile at room temperature, and the mixture was stirred for 2 hour. This reaction solution was poured into 2% hydrochloric acid, and extracted with ethyl acetate. The organic layer was washed with saturated saline, dried over anhydrous magnesium sulfate, and concentrated. The residue was subjected to silica gel column chromatography to obtain 13 g of methyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate [Compound 3-11 of the present invention].

PRODUCTION EXAMPLE 17
Production of Compound 4-20 of the Present Invention

Methyl [2-{2,4-difluoro-5-[3-methyl-2,6-dioxo-4-(trifluoromethyl)-1,2,3,6-tetrahydropyrimidin-1-yl]phenoxy}phenoxy]acetate [Compound 4-20 of the present invention] was produced from 5-fluoro-2-{2-(methoxycarbonyl)methoxyphenoxy}-4-[3-methyl-2,6-dioxo-4-(trifluoromethyl)-1,2,3,6-tetrahydropyrimidin-1-yl]aniline (produced in Intermediate Production Example 10) according to the process of production example 16.

$^1$H-NMR (CDCl$_3$/250 MHz) δ (ppm): 3.52 (s, 3H,), 3.72 (s, 3H), 4.64 (s, 2H), 6.32 (s, 1H), 6.8–7.2 (m, 6H)

PRODUCTION EXAMPLE 18
production of Compound 4-21 of the Present Invention

Methyl [2-{2-bromo-4-fluoro-5-[3-methyl-2,6-dioxo-4-(trifluoromethyl)-1,2,3,6-tetrahydropyrimidin-1-yl]phenoxy}phenoxy]acetate [Compound 4-21 of the present invention] was produced from 5-fluoro-2-{2-(methoxycarbonyl)methoxyphenoxy}-4-[3-methyl-2,6-dioxo-4-(trifluoromethyl)-1,2,3,6-tetrahydropyrimidin-1-yl]aniline (produced in Intermediate Production Example 10) according to the process of production example 16.

$^1$H-NMR (CDCl$_3$/300 MHz) δ (ppm): 3.53 (q, 3H, J=1.0 Hz), 3.72 (s, 3H), 4.65 (s, 2H), 6.33 (s, 1H), 6.72 (d, 1H, J=6.4 Hz), 6.8–7.2 (m, 4H), 7.53 (d, 1H, J=8.6 Hz)

PRODUCTION EXAMPLE 19
Production of Compound 4-22

Methyl [2-{2-cyano-4-fluoro-5-[3-methyl-2,6-dioxo-4-(trifluoromethyl)-1,2,3,6-tetrahydropyrimidin-1-yl]phenoxy}phenoxyacetate [Compound 4-22 of the present invention] was produced from Methyl [2-{2-bromo-4-fluoro-5-[3-methyl-2,6-dioxo-4-(trifluoromethyl)-1,2,3,6-tetrahydropyrimidin-1-yl]phenoxy}phenoxy]acetate [Compound 4-21] according to the forth process of Intermediate production example 9 described below.

$^1$H-NMR (CDCl$_3$/250 MHz) δ (ppm): 3.49 (q, 3H, J=0.8 Hz), 3.71 (s, 3H), 4.63 (s, 2H), 6.27 (s, 1H), 6.79 (d, 1H, J=5.8 Hz), 6.87 (d, 1H, J=8.1 Hz), 7.0–7.1 (m, 1H), 7.1–7.3 (m, 2H), 7.49 (d, 1H, J=8.4 Hz)

INTERMEDIATE PRODUCTION EXAMPLE 1
Production of 4-{2-chloro-4-fluoro-5-[3-methyl-2,6-dioxo-4-(trifluoromethyl)-1,2,3,6-tetrahydropyrimidin-1-yl]phenoxy}phenol First Process:

A mixture of 1.71 g of 4-benzyloxyphenol and 4.0 ml of N,N-dimethylformamide was added dropwise into a mixture of 0.34 g of sodium hydride and 8.5 ml of N,N-dimethylformamide while cooling with ice, and the mixture was stirred for 20 minutes. A mixture of 3.0 g of 2,5-difluoro-4-[3-methyl-2,6-dioxo-4-(trifluoromethyl)-1,2,3,6-tetrahydropyrimidin-1-yl]nitrobenzene (described later, produced in Intermediate Production Example 4) and 7.0 ml of N,N-dimethylformamide was added dropwise at the same temperature, and stirred for 1 hour. This reaction solution was poured into ice water, and extracted with ethyl acetate. The organic layer was washed once with 1N hydrochloric acid and once with saturated saline and dried over anhydrous magnesium sulfate, and concentrated. The residue was subjected to silica gel column chromatography to obtain 2.0 g of 2-(4-benzyloxyphenoxy)-5-fluoro-4-[3-methyl-2,6-dioxo-4-(trifluoromethyl)-1,2,3,6-tetrahydropyrimidin-1-yl]nitrobenzene.

$^1$H-NMR (CDCl$_3$/250 MHz) δ (ppm): 3.51 (q, 3H, J=1.2 Hz), 5.04 (s, 2H), 6.31 (s, 1H), 6.87 (d, 1H, J=5.9 Hz), 6.9 to 7.1 (m, 4H), 7.3 to 7.5 (m, 5H), 7.84 (d, 1H, J=8.6 Hz)

Second Process:

To a mixture of 2.0 g of an iron powder, 6 ml of acetic acid and 0.6 ml of water was added dropwise a solution of 1.9 g of 2-(4-benzyloxyphenoxy)-5-fluoro-4-[3-methyl-2,6-dioxo-4-(trifluoromethyl)-1,2,3,6-tetrahydropyrimidin-1-yl]nitrobenzene in 5.0 ml of acetic acid, while maintaining the temperature of the reaction solution at 35° C. or lower. After completion of the addition, the mixture was stirred for 2 hours, then, the reaction solution was filtrated through Celite and diluted with ethyl acetate. The mixture was neutralized with saturated aqueous sodium bicarbonate, the organic layer was washed with saturated saline, dried over anhydrous magnesium sulfate, and concentrated, then, the resulted residue was subjected to silica gel column chromatography to obtain 1.0 g of 2-(4-benzyloxyphenoxy)-5-fluoro-4-[3-methyl-2,6-dioxo-4-(trifluoromethyl)-1,2,3,6-tetrahydropyrimidin-1-yl]aniline.

$^1$H-NMR (CDCl$_3$/250 MHz) δ (ppm): 3.51 (q, 3H, J=1.3 Hz), 5.02 (s, 2H), 6.30 (s, 1H), 6.58 (d, 1H, J=6.9 Hz), 6.62 (d, 1H, J=10.8 Hz), 7.3 to 7.5 (m, 5H)

Third Process:

0.46 g of isoamyl nitrite was added dropwise to a mixture of 1.0 g of 2-(4-benzyloxyphenoxy)-5-fluoro-4-[3-methyl- 2,6-dioxo-4-(trifluoromethyl)-1,2,3,6-tetrahydropyrimidin-1-yl]aniline, 0.38 g of copper (I) chloride, 0.78 g of copper (II) chloride, and 14 ml of acetonitrile at room temperature, and the mixture was stirred for 1 hour. This reaction solution was poured into 2% hydrochloric acid, and extracted with ethyl acetate. The organic layer was washed with saturated saline, dried over anhydrous magnesium sulfate, and concentrated. The residue was subjected to silica gel column chromatography to obtain 0.73 g of ([4-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene.

$^1$H-NMR (CDCl$_3$/300 MHz) δ (ppm): 3.51 (s, 3H), 5.03 (s, 2H), 6.30 (s, 1H), 6.74 (d, 1H, J=6.5 Hz), 6.9 to 7.0 (m, 4H), 7.2 to 7.5 (m, 6H)

Fourth Process:

To 0.72 g of ([4-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene, were added 2 ml of ethyl acetate, 0.7 ml of ethanol and 36 mg of 10% palladium/carbon, and the mixture was stirred for 5 hours at room temperature under hydrogen atmosphere. The reaction system was purged with nitrogen, then, the reaction solution was filtrated through Celite, the filtrate was concentrated to obtain 0.48 g of 4-{2-chloro-4-fluoro-5-[3-methyl-2,6-dioxo-4-(trifluoromethyl)-1,2,3,6-tetrahydropyrimidin-1-yl]phenoxy}phenol.

$^1$H-NMR (CDCl$_3$/300 MHz) δ (ppm): 3.51 (s, 3H), 5.2 to 5.5 (b, 1H), 6.30 (s, 1H), 6.6 to 7.0 (m, 5H), 7.36 (d, 1H, J=9.0 Hz)

INTERMEDIATE PRODUCTION EXAMPLE 2

Production of 3-{2-chloro-4-fluoro-5-[3-methyl-2,6-dioxo-4-(trifluoromethyl)-1,2,3,6-tetrahydropyrimidin-1 -yl]phenoxy}phenol First Process:

A mixture of 1.71 g of 3-benzyloxyphenol and 4.0 ml of N,N-dimethylformamide was added dropwise into a mixture of 0.34 g of sodium hydride and 8.5 ml of N,N-dimethylformamide while cooling with ice, and the mixture was stirred for 20 minutes. A mixture of 3.0 g of 2,5-difluoro-4-[3-methyl-2,6-dioxo-4-(trifluoromethyl)-1,2,3,6-tetrahydropyrimidin-1-yl]nitrobenzene (described later, produced in Intermediate Production Example 4) and 7.0 ml of N,N-dimethylformamide was added dropwise at the same temperature, and stirred for 1 hour. This reaction solution was poured into ice water, and extracted with ethyl acetate. The organic layer was washed once with 1N hydrochloric acid and once with saturated saline, and dried over anhydrous magnesium sulfate, and concentrated. The residue was subjected to silica gel column chromatography to obtain 2.4 g of 2-(3-benzyloxyphenoxy)-5-fluoro-4-[3-methyl-2,6-dioxo-4-(trifluoromethyl)-1,2,3,6-tetrahydropyrimidin-1-yl]nitrobenzene.

$^1$H-NMR (CDCl$_3$/300 MHz) δ (ppm): 3.53 (q, 3H, J=1.2 Hz), 5.03 (s, 2H), 6.33 (s, 1H), 6.6 to 6.7 (m, 1H), 6.7 to 6.8 (m, 1H), 6.8 to 6.9 (m, 1H), 7.01 (d, 1H, J=6.1 Hz), 7.2 to 7.5 (m, 6H), 7.87 (d, 1H, J=8.6 Hz)

Second Process:

To a mixture of 2.5 g of an iron powder, 8 ml of acetic acid and 0.8 ml of water was added dropwise a solution of 2.4 g of 2-(3-benzyloxyphenoxy)-5-fluoro-4-[3-methyl-2,6-dioxo-4-(trifluoromethyl)-1,2,3,6-tetrahydropyrimidin-1-yl]nitrobenzene in 6.0 ml of acetic acid, while maintaining the temperature of the reaction solution at 35° C. or lower. After completion of the addition, the mixture was stirred for 2 hours, then, the reaction solution was filtrated through Celite and diluted with ethyl acetate. The mixture was neutralized with saturated aqueous sodium bicarbonate, the organic layer was washed with saturated saline, dried over anhydrous magnesium sulfate, and concentrated, then, the resulted residue was subjected to silica gel column chromatography to obtain 1.5 g of 2-(3-benzyloxyphenoxy)-5-fluoro-4-[3-methyl-2,6-dioxo-4-(trifluoromethyl)-1,2,3,6-tetrahydropyrimidin-1-yl]aniline.

Melting Point: 67.0° C.

Third Process:

0.34 g of isoamyl nitrite was added dropwise to a mixture of 1.5 g of 2-(3-benzyloxyphenoxy)-5-fluoro-4-[3-methyl-2,6-dioxo-4-(trifluoromethyl)-1,2,3,6-tetrahydropyrimidin-1-yl]aniline, 0.57 g of copper (I) chloride, 1.17 g of copper (II) chloride, and 21 ml of acetonitrile at room temperature, and the mixture was stirred for 1 hour. This reaction solution was poured into 2% hydrochloric acid, and extracted with ethyl acetate. The organic layer was washed with saturated saline, dried over anhydrous magnesium sulfate, and concentrated. The residue was subjected to silica gel column chromatography to obtain 1.01 g of ([3-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene.

$^1$H-NMR (CDCl$_3$/300 MHz) δ (ppm): 3.53 (q, 3H, J=0.9 Hz), 5.03 (s, 2H), 6.33 (s, 1H), 6.6 to 6.7 (m, 2H), 6.7 to 6.8 (m, 1H), 6.92 (d, 1H, J=6.5 Hz), 7.2 to 7.5 (m, 7H)

Fourth Process:

To 1.01 g of ([3-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene, were added 3 ml of ethyl acetate, 1 ml of ethanol and 50 mg of 10% palladium/carbon, and the mixture was stirred for 5 hours at room temperature under hydrogen atmosphere. The reaction system was purged with nitrogen, then, the reaction solution was filtrated through Celite, the filtrate was concentrated to obtain 0.68 g of 3-{2-chloro-4-fluoro-5-[3-methyl-2,6-dioxo-4-(trifluoromethyl)-1,2,3,6-tetrahydropyrimidin-1-yl]phenoxy}phenol.

$^1$H-NMR (CDCl$_3$/300 MHz) δ (ppm): 3.52 (s, 3H), 5.5 to 5.8 (b, 1H), 6.32 (s, 1H), 6.4 to 6.5 (m, 1H), 6.5 to 6.6 (m, 2H), 6.93 (d, 1H, J=6.7 Hz), 7.17 (dd, 1H, J=8.3 Hz, 7.9 Hz), 7.38 (d, 1H, J=9.0 Hz),

INTERMEDIATE PRODUCTION EXAMPLE 3

Production of 2-{2-chloro-4-fluoro-5-[3-methyl-2,6-dioxo-4-(trifluoromethyl)-1,2,3,6-tetrahydropyrimidin-1-yl]phenoxy}phenol First Process:

A mixture of 4.05 g of 2-benzyloxyphenol and 9.5 ml of N,N-dimethylformamide was added dropwise into a mixture of 0.80 g of sodium hydride and 20 ml of N,N-dimethylformamide while cooling with ice, and the mixture was stirred for 30 minutes. A mixture of 7.1 g of 2,5-difluoro-4-[3-methyl-2,6-dioxo-4-(trifluoromethyl)-1,2,3,6-tetrahydropyrimidin-1-yl]nitrobenzene (described later, produced in Intermediate Production Example 4) and 17 ml of N,N-dimethylformamide was added dropwise at the same temperature, and stirred for 1 hour. This reaction solution was poured into ice water, and extracted with ethyl acetate. The organic layer was washed once with 1N hydrochloric acid and once with saturated saline and dried over anhydrous magnesium sulfate, and concentrated. The residue was subjected to silica gel column chromatography to obtain 8.6 g of 2-(2-benzyloxyphenoxy)-5-fluoro-4-[3-methyl-2,6-dioxo-4-(trifluoromethyl)-1,2,3,6-tetrahydropyrimidin-1-yl]nitrobenzene.

$^1$H-NMR (CDCl$_3$/250 MHz) δ (ppm): 3.52 (q, 3H, J=1.1 Hz), 5.01 (s, 2H), 6.31 (s, 1H), 6.81 (d, 1H, J=6.0 Hz), 6.9 to 7.1 (m, 2H), 7.1 to 7.4 (m, 7H), 7.78 (d, 1H, J=8.7 Hz)

Second Process:

To a of 8.6 g of an iron powder, 27 ml of acetic acid and 2.7 ml of water was added dropwise a solution of 8.6 g of 2-(2-benzyloxyphenoxy)-5-fluoro-4-[3-methyl-2,6-dioxo-4-(trifluoromethyl)-1,2,3,6-tetrahydropyrimidin-1-yl] nitrobenzene in 23 ml of acetic acid, while maintaining the temperature of the reaction solution at 35° C. or lower. After completion of the addition, the mixture was stirred for 2 hours, then, the reaction solution was filtrated through Celite and diluted with ethyl acetate. The mixture was neutralized with saturated aqueous sodium bicarbonate, the organic layer was washed with saturated saline, dried over anhydrous magnesium sulfate, and concentrated, then, the resulted residue was subjected to silica gel column chromatography to obtain 6.46 g of 2-(2-benzyloxyphenoxy)-5-fluoro-4-[3-methyl-2,6-dioxo-4-(trifluoromethyl)-1,2,3,6-tetrahydropyrimidin-1-yl]aniline.

$^1$H-NMR (CDCl$_3$/250 MHz) δ (ppm): 3.50 (q, 3H, J=1.2 Hz), 5.06 (s, 2H), 6.29 (s, 1H), 6.57 (dd, 1H, J=8.5, 1.6 Hz), 6.9 to 7.0 (m, 1H), 7.0 to 7.1 (m, 3H), 7.2 to 7.4 (m, 6H)

Third Process:

4.46 g of isoamyl nitrite was added dropwise to a mixture of 6.46 g of 2-(2-benzyloxyphenoxy)-5-fluoro-4-[3-methyl-2,6-dioxo-4-(trifluoromethyl)-1,2,3,6-tetrahydropyrimidin-1-yl]aniline, 2.45 g of copper (I) chloride, 5.04 g of copper (II) chloride, and 90 ml of acetonitrile at room temperature, and the mixture was stirred for 1 hour. This reaction solution was poured into 2% hydrochloric acid, and extracted with ethyl acetate. The organic layer was washed with saturated saline, dried over anhydrous magnesium sulfate, and concentrated. The residue was subjected to silica gel column chromatography to obtain 4.6 g of ([2-{2-chloro-4-fluoro-5-[3-methyl-2,6-dioxo-4-(trifluoromethyl)-1,2,3,6-tetrahydropyrimidin-1-yl]phenoxy}phenoxy]methyl) benzene.

Melting Point: 50.8° C.

Fourth Process:

To 4.5 g of ([2-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene, were added 230 ml of ethyl acetate and 0.46 g of 10% palladium/carbon, and the mixture was stirred for 5 hours at room temperature under hydrogen atmosphere. The reaction system was purged with nitrogen, then, the reaction solution was filtrated through Celite, the filtrate was concentrated to obtain 3.57 g of 2-{2-chloro-4-fluoro-5-[3-methyl-2,6-dioxo-4-(trifluoromethyl)-1,2,3,6-tetrahydropyrimidin-1 -yl] phenoxy}phenol.

Melting Point: 55.4° C.

INTERMEDIATE PRODUCTION EXAMPLE 4

Production of 2,5-difluoro-4-[3-methyl-2,6-dioxo-4-(trifluoromethyl)-1,2,3,6-tetrahydropyrimidin-1-yl] nitrobenzene 1.77 g of 2,4,5-trifluoronitrobenzene and 1.94 g of 3-methyl-2,6-dioxo-4-(trifluoromethyl)-1,2,3,6-tetrahydropyrimidine were dissolved in 10 ml of dimethyl sulfoxide, and 1.52 g of anhydrous potassium carbonate was added to this at room temperature, then, the mixture was stirred for 1 hour at 80° C. The reaction solution was allowed to cool to room temperature, then, the reaction solution was poured into ice water, and extracted with ethyl acetate. The organic layer was washed with saturated saline, dried over anhydrous magnesium sulfate, and concentrated. The residue was subjected to silica gel column chromatography to obtain 1.51 g of 2,5 difluoro-4-[3-methyl-2,6-dioxo-4-(trifluoromethyl)-1,2,3,6-tetrahydropyrimidin-1-yl] nitrobenzene.

Melting Point: 150° C.

INTERMEDIATE PRODUCTION EXAMPLE 5

Production of methyl [2-{2-chloro-4-fluoro-5-[2,6-dioxo-4-(trifluoromethyl)-1,2,3,6-tetrahydropyrimidin-1-yl] phenoxy}phenoxy]acetate First Process:

2.73 g of 2-methoxyphenol and 5.5 g of potassium carbonate were added to 20 ml of N,N-dimethylformamide, and the mixture was heated to 60° C. Into this mixture was added dropwise a solution comprising 4.3 g of N-(2,5-difluoro-4-nitrophenyl)acetamide and 30 ml of N,N-dimethylformamide at temperature from 60 to 65° C. The temperature of the mixture was kept for 1 hour while stirring, then, the mixture was cooled to room temperature, poured into water, extracted with ethyl acetate, and the organic layer was washed with dilute hydrochloric acid, washed with water, dried over magnesium sulfate, and concentrated to obtain 5.52 g of N-[2-fluoro-5-(2-methoxyphenoxy)-4-nitrophenyl]acetamide.

$^1$H-NMR (250 MHz, CDCl$_3$) δ (ppm): 2.16 (3H, s), 3.78 (3H, s), 6.85 to 7.22 (4H, m), 7.75 to 7.83 (1H, br), 7.83 (1H, d, J=10.7 Hz), 8.04 (1H, d, J=6.9 Hz)

Second Process:

5.4 g of N-[2-fluoro-5-(2-methoxyphenoxy)-4-nitrophenyl]acetamide was dissolved in 50 mol of methylene chloride, then, 4.7 g of boron tribromide was added under ice cooling. The mixture was stirred for 2 hours under the same temperature, conc. hydrochloric acid was added to the solution and the resulted mixture was poured into water, extracted with ethyl acetate, the organic layer was washed with water, dried over magnesium sulfate, concentrated, and the resulted crystal was washed with t-butyl methyl ether to obtain 3.2 g of N-[2-fluoro-5-(2-hydroxyphenoxy)-4 -nitrophenyl]acetamide.

$^1$H-NMR (300 MHz, CDCl$_3$) δ (ppm): 2.20 (3H, s), 6.33 (1H, bs), 6.86 to 7.23 (4H, m), 7.63 (1H, bs), 7.81 (1H, d, J=10.3 Hz), 8.34 (1H, d, J=6.7 Hz)

Third Process:

3.02 g of N-[2-fluoro-5-(2-hydroxyphenoxy)-4-nitrophenyl]acetamide was dissolved in 20 ml of N,N-dimethylformamide, then, 1.5 g of potassium carbonate was added, and the mixture was stirred for 1 hour at room temperature. Then, 1.6 g of methyl bromoacetate was added at room temperature. The mixture was stirred for 2 hours under the same condition, poured into water, extracted with ethyl acetate, and the organic layer was washed with dilute hydrochloric acid, washed with water, dried over magnesium sulfate and concentrated, and the resulted crystal was washed with t-butyl methyl ether to obtain 3.01 g of methyl [2-(5-acetylamino-4-fluoro-2-nitrophenoxy)phenoxy] acetate.

$^1$H-NMR (250 MHz, CDCl$_3$) δ (ppm): 2.16 (3H, s), 3.73 (3H, s), 4.62 (2H, s), 6.95 to 7.26 (4H, m), 7.71 (1H, bs), 7.85 (1H, d, J=10.7 Hz), 8.06 (1H, d, J=6.9 Hz)

Fourth Process:

Into a mixture of 40 ml of acetic acid and 40 ml of water was added 2.2 g of an iron powder, and the mixture was heated to 80° C. Into the mixture was added 3.0 g of methyl [2-(5-acetylamino-4-fluoro-2-nitrophenoxy)phenoxy] acetate, and the mixture was heated for 30 minutes under reflux. Thereafter, the mixture was poured into water, extracted with ethyl acetate, the organic layer was washed with water, and washed with saturated aqueous sodium bicarbonate, dried over magnesium sulfate, and concentrated to obtain 2.01 g of methyl [2-(5-acetylamino-2-amino-4-fluorophenoxy)phenoxy]acetate.

$^1$H-NMR (250 MHz, CDCl$_3$) δ (ppm): 2.11 (3H, s), 3.31 to 4.15 (2H, br), 3.76 (3H, s), 4.71 (2H, s), 6.54 (1H, d, J=11.9 Hz), 6.90 to 7.01 (4H, m), 7.17 (1H, bs), 7.69 (1H, d, J=7.54 Hz)

Fifth Process:

To 30 ml of conc. hydrochloric acid was added 2.0 g of methyl [2-(5-acetylamino-2-amino-4-fluorophenoxy)

phenoxy]acetate, and the mixture was stirred for 1 hour at room temperature. Thereafter, a mixture of 0.42 g of sodium nitrite and 3 ml of water was added under ice cool. The mixture was stirred for 1 hour under the same condition, then, 40 ml of t-butyl methyl ether was added, then, 0.85 g of copper (I) chloride was added. The mixture was stirred for 30 minutes, then, water was added to this, and extracted with t-butyl methyl ether, and the organic layer was washed with water, dried over magnesium sulfate and concentrated, and the resulted residue was purified by column chromatography (eluent: hexane/ethyl acetate=2/1) to obtain 0.52 g of methyl [2-(5-acetylamino-2-chloro-4-fluorophenoxy)phenoxy]acetate.

Melting Point: 138.9° C.

Sixth Process:

Into 10 ml of boron trifluoride methanol complex, methanol solution was added 0.25 g of methyl [2-(5-acetylamino-2-chloro-4-fluorophenoxy)phenoxy]acetate, and the mixture was heated for 3 hours while stirring. Thereafter, the reaction solution was concentrated, the residue was dissolved in ethyl acetate, and washed with saturated aqueous sodium bicarbonate, dried over magnesium sulfate, and concentrated to obtain 0.2 g of methyl [2-(5-amino-2-chloro-4-fluorophenoxy)phenoxy]acetate [Intermediate compound A3-22].

$^1$H-NMR (250 MHz, CDCl$_3$) δ (ppm): 3.74 (3H, s), 3.86 (2H, br), 4.70 (2H, s), 6.36 (1H, d, J=8.21 Hz), 6.83 to 7.09 (5H, m)

Seventh Process:

Into a mixture of methyl [2-(5-amino-2-chloro-4-fluorophenoxy)phenoxy]acetate [Intermediate compound A3-22], methyl chloroformate and tetrahydrofuran is added dropwise pyridine, and the mixture is stirred at room temperature. Dilute hydrochloric acid is added to the reaction solution, and this is extracted with ethyl acetate. The organic layer is washed with saturated saline, dried over anhydrous magnesium sulfate, and concentrated to obtain methyl [2-(2-chloro-4-fluoro-5-methoxycarbonylaminophenoxy)phenoxy]acetate [Intermediate compound A9-22].

Eighth Process:

To ethyl 3-amino-4,4,4-trifluorocrotonate are added N,N-dimethylformamide and sodium hydride and the mixture is stirred at 0° C. Thereafter, to the reaction solution is added a mixture of methyl [2-(2-chloro-4-fluoro-5-methoxycarbonylaminophenoxy)phenoxy]acetate [Intermediate compound A9-22] and N,N-dimethylformamide, and the mixture is stirred at 80° C. Then reaction solution is cooled to room temperature, then, poured into a mixture of hydrochloric acid and ice water, and the deposited crystal is collected by filtration to obtain methyl [2-{2-chloro-4-fluoro-5-[2,6-dioxo-4-(trifluoromethyl)-1,2,3,6-tetrahydropyrimidin-1-yl]phenoxy}phenoxy]acetate.

INTERMEDIATE PRODUCTION EXAMPLE 6

Production of ethyl [2-{2-chloro-4-fluoro-5-[2,6-dioxo-4-(trifluoromethyl)-1,2,3,6-tetrahydropyrimidin-1-yl]phenoxy}phenoxy]acetate First Process:

1.1 g of catechol and 2.76 g of potassium carbonate were added to 20 ml of N,N-dimethylformamide, and the mixture was heated to 60° C. Into this mixture was added dropwise a solution comprising 2.16 g of N-(2,5-difluoro-4-nitrophenyl)acetamide and 10 ml of N,N-dimethylformamide at temperatures from 65 to 70° C. The temperature of the mixture was kept for 1 hour, then, the mixture was cooled to room temperature, poured into water, extracted with ethyl acetate, and the organic layer was washed with dilute hydrochloric acid, washed with water, dried over magnesium sulfate, concentrated, and the resulted crystal was washed with t-butyl methyl ether to obtain 2.56 g of N-[2-fluoro-5-(2-hydroxyphenoxy)-4-nitrophenyl]acetamide.

$^1$H-NMR (300 MHz, CDCl$_3$) δ (ppm): 2.20 (3H, s), 6.33 (1H, bs), 6.86 to 7.23 (4H, m), 7.63 (1H, bs), 7.81 (1H, d, J=10.3 Hz), 8.34 (1H, d, J=6.7 Hz)

Second Process:

Into a mixture of 25 ml of acetic acid and 25 ml of water was added 9.5 g of an iron powder, and the mixture was heated to 80° C. Into the mixture was added dropwise a solution composed of 10.0 g of N-[2-fluoro-5-(2-hydroxyphenoxy)-4-nitrophenyl]acetamide and 100 ml of ethyl acetate. The mixture was heated for 1 hour under reflux, then, poured into water, extracted with ethyl acetate, the organic layer was washed with water, and washed with saturated aqueous sodium bicarbonate, dried over magnesium sulfate, and concentrated to obtain 7.42 g of N-[4-amino-2-fluoro-5-(2-hydroxyphenoxy)phenyl]acetamide.

$^1$H-NMR (250 MHz, CDCl$_3$) δ (ppm): 2.16 (3H, s), 6.48 (1H, d, J=11.6 Hz), 6.74 to 6.78 (2H, m), 6.93 to 6.96 (2H, m), 7.35 (1H, bs), 7.47 (1H, d, J=7.4 Hz)

Third Process:

7.4 g of N-[4-amino-2-fluoro-5-(2-hydroxyphenoxy)phenyl]acetamide was dissolved in 30 ml of acetonitrile, then, 5.42 g of copper (II) chloride was added and the mixture was stirred at room temperature. To this was added dropwise a solution composed of 4.16 g of t-butyl nitrite and 5 ml of acetonitrile around room temperature. The mixture was stirred for 1 hour at room temperature, then, poured into water, extracted with ethyl acetate, the organic layer was washed with dilute hydrochloric acid, washed with water, dried over magnesium sulfate and concentrated, and the resulted residue was purified by silica gel column chromatography (eluent: hexane/ethyl acetate=2/1) to obtain 3.92 g of N-[4-chloro-2-fluoro-5-(2-hydroxyphenoxy)phenyl]acetamide.

$^1$H-NMR (250 MHz, CDCl$_3$) δ (ppm): 2.19 (3H, s), 5.72 (1H, s), 6.70 to 6.84 (2H, m), 7.01 to 7.03 (2H, m), 7.23 (1H, d, J=10.3 Hz), 7.34 (1H, bs), 8.18 (2H, d, J=7.4 Hz).

Fourth Process:

N-[4-chloro-2-fluoro-5-(2-hydroxyphenoxy)phenyl]acetamide is dissolved in N,N-dimethylformamide, then, potassium carbonate is added and the mixture is stirred at room temperature. Then, ethyl bromoacetate is added at room temperature. The mixture is stirred under the same temperature, poured into water, extracted with ethyl acetate, the organic layer is washed with dilute hydrochloric acid, washed with water, dried over magnesium sulfate and concentrated, and the resulted crystal is washed with t-butyl methyl ether to obtain ethyl [2-(5-acetylamino-2-chloro-4-fluorophenoxy)phenoxy]acetate.

Fifth Process:

Into a boron trifluoride methanol complex, methanol solution is added ethyl [2-(5-acetylamino-2-chloro-4-fluorophenoxy)phenoxy]acetate, and the mixture is heated while stirring. Thereafter, the reaction solution is concentrated, the residue is dissolved in ethyl acetate, and washed with saturated aqueous sodium bicarbonate, dried over magnesium sulfate, and concentrated to obtain ethyl [2-(5-amino-2-chloro-4-fluorophenoxy)phenoxy]acetate [Intermediate compound A3-23].

Sixth Process:

Into a mixture of ethyl [2-(5-amino-2-chloro-4-fluorophenoxy)phenoxy]acetate [Intermediate compound A3-23], ethyl chloroformate and tetrahydrofuran is added dropwise pyridine, and the mixture is stirred at room temperature. Dilute hydrochloric acid is added to the reaction solution, and this is extracted with ethyl acetate. The organic layer is washed with saturated saline, dried over anhydrous magnesium sulfate, and concentrated to obtain ethyl [2-(2-chloro-4-fluoro-5-ethoxycarbonylaminophenoxy)phenoxy]acetate [Intermediate compound A8-23].

Seventh Process:

To ethyl 3-amino-4,4,4-trifluorocrotonate are added N,N-dimethylformamide and sodium hydride and the mixture is stirred at 0° C. Thereafter, to the reaction solution is added a mixture of ethyl [2-(2-chloro-4-fluoro-5-ethoxycarbonylaminophenoxy)phenoxy]acetate [Intermediate compound A8-23] and N,N-dimethylformamide, and the mixture is stirred at 80° C. Then reaction solution is cooled to room temperature, then, poured into a mixture of hydrochloric acid and ice water, and the deposited crystal is collected by filtration to obtain ethyl [2-{2-chloro-5-[2,6-dioxo-4-(trifluoromethyl)-1,2,3,6-tetrahydropyrimidin-1-yl]-4-fluorophenoxy}phenoxy]acetate.s

INTERMEDIATE PRODUCTION EXAMPLE 7

Production of ethyl [2-{2-chloro -5-[2,6-dioxo-4-(trifluoromethyl)-1,2,3,6-tetrahydropyrimidin-1-yl]-4-fluorophenoxy}phenoxy]acetate First Process:

Into a mixture of ethyl [2-(5-amino-2-chloro-4-fluorophenoxy)phenoxy]acetate [Intermediate compound A3-23], trichloromethyl chloroformate and toluene is added dropwise activated carbon, and the mixture is heated under reflux. The reaction solution is filtrated and the solvent is distilled off to obtain 4-chloro-2-fluoro-5-{2-(ethoxycarbonylmethoxy)phenoxy}phenyl isocyanate [Intermediate compound A12-23].

Second Process:

To ethyl 3-amino-4,4,4-trifluorocrotonate are added N,N-dimethylformamide and sodium hydride and the mixture is stirred at 0° C. Thereafter, to the reaction solution is added a mixture of 4-chloro-2-fluoro-5-{2-(ethoxycarbonylmethoxy)phenoxy}phenyl isocyanate [Intermediate compound A12-23] and N,N-dimethylformamide, and the mixture is stirred at room temperature. The reaction solution is poured into a mixture of hydrochloric acid and ice water, and the deposited crystal is collected by filtration to obtain ethyl [2-{2-chloro -5-[2,6-dioxo-4-(trifluoromethyl)-1,2,3,6-tetrahydropyrimidin-1-yl]-4-fluorophenoxy}phenoxy]acetate.

INTERMEDIATE PRODUCTION EXAMPLE 8

Production of methyl [2-{2-chloro-5-[2,6-dioxo-4-(trifluoromethyl)-1,2,3,6-tetrahydropyrimidin-1-yl]-4-fluorophenoxy}phenoxy]acetate

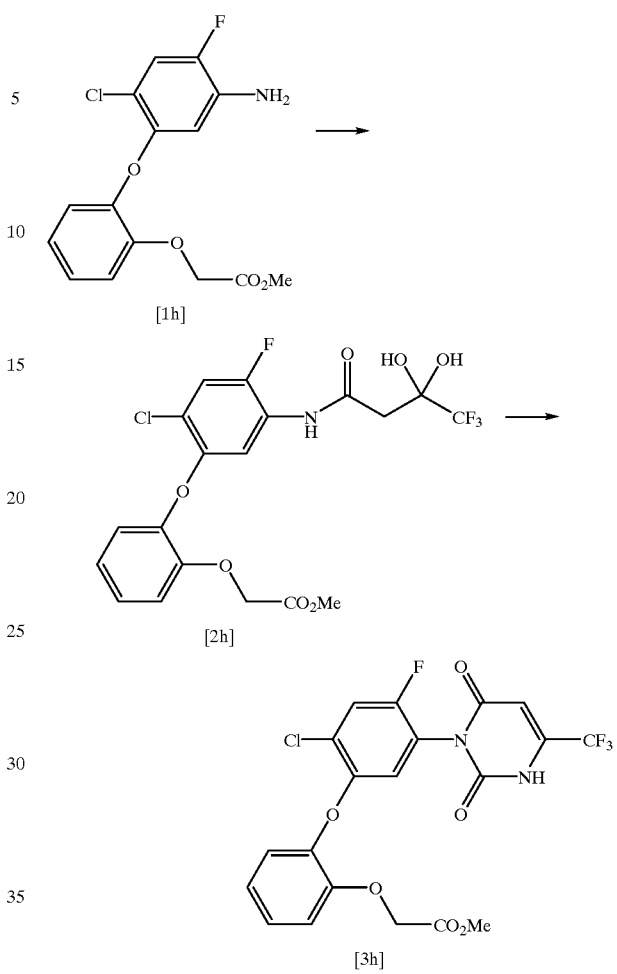

First Process: Production of compound [2h] from compound [1h]

A solution consisting of 4.85 g of compound [1h], 2.88 g of ethyl trifluoroacetoacetate and 40 ml of toluene was subjected to azeotropic reaction with removing ethanol by passing through molecular sieves 5A for 6 hours. After cooling, 50 ml of ethyl acetate was added to the reaction mixture, then, the organic layer was washed with concentrated hydrochloric acid, water and saturated saline, dried over anhydrous sodium sulfate, and concentrated under reduced pressure. The residue was washed with hexane to obtain 5.82 g of crude compound [2h].

m.p.: 165.3° C.

Second process: Production of compound [3h] from compound [2h]

To a solution of 1.0 g of the crude compound [2h] and 3 ml of tetrahydrofuran, 4 ml of acetic acid and 0.87 g of potassium cyanate were added, and the mixture was stirred at room temperature for 6 hours, then, heated under reflux at 120° C. for 2 hours. After cooling, 30 ml of water was added to the reaction mixture and the mixture was extracted with ethyl acetate. The organic layer was washed with saturated aqueous sodium bicarbonate solution, water and saturated saline, and then, dried over anhydrous sodium sulfate, and concentrated under reduced pressure. The residue was subjected to silica gel column chromatography to obtain 0.67 g of compound [3h].

1H-NMR (CDCl$_3$/250 MHz) δ (ppm): 3.72 (3H, s), 4.65 (2H, s), 6.16(1H, s), 6.77(1H, d, J=6.6 Hz), 6.89–7.15 (4H, m), 7.36 (1H, d, J=8.9 Hz)

ethyl [2-{2-chloro-5-[2,6-dioxo-4-(trifluoromethyl)-1,2,3,6-tetrahydropyrimidin-1-yl]-4-fluorophenoxy}phenoxy]acetate is produced from ethyl [2-(5-amino-2-chloro-4-fluorophenoxy)phenoxy]acetate [Intermediate compound A3-23] according to the process of Intermediate Production Example 8.

INTERMEDIATE PRODUCTION EXAMPLE 9
Production of 3-{2-cyano-4-fluoro-5-[3-methyl-2,6-dioxo-4-(trifluoromethyl)-1,2,3,6-tetrahydropyrimidin-1-yl]phenoxy}phenol First process:
The mixture of 3.53 g of 3-methoxyphenol, 5.12 g of anhydrous potassium carbonate, 10 g of 2,5-difluoro-4-[3-methyl-2,6-dioxo-4-(trifluoromethyl)-1,2,3,6-tetrahydropyrimidin-1-yl]nitrobenzen (described above, produced in Intermediate Production Example 4) and 40 ml of N,N-dimethylformamide was stirred at 60 to 70° C. for 2 hours. The reaction mixture was poured into the mixture of aqueous hydrochloric acid solution and ice water and extracted with ethyl acetate. The organic layer was washed with saturated saline, dried over anhydrous magnesium sulfate, and concentrated. The residue was subjected to silica gel column chromatography to obtain 4.17 g of 5-fluoro-2-(3-methoxyphenoxy)-4-[3-methyl-2,6-dioxo-4-(trifluoromethyl)-1,2,3,6-tetrahydropyrimidin-1-yl]nitrobenzene.

$^1$H-NMR (CDCl$_3$/250 MHz) δ (ppm): 3.53 (q, 3H, J=1.2 Hz), 3.79 (s, 3H), 6.33 (s, 1H), 6.6–6.7 (m, 2H), 6.7–6.8 (m, 1H), 7.00 (d, 1H, J=6.1 Hz), 7.2–7.3 (m, 1H), 7.88 (d, 1H, J=8.6 Hz)

Second process:
A solution of 4.17 g of 5-fluoro-2-(3 -methoxyphenoxy)-4-[3-methyl-2,6-dioxo-4-(trifluoromethyl)-1,2,3,6-tetrahydropyrimidin-1-yl]nitrobenzene in 10 ml of acetic acid was added dropwise over 20 minutes to a mixture of 4.5 g of iron powder, 10 ml of acetic acid and 1 ml of water. After the addition, the mixture was stirred for 2 hours, filtered through celite and diluted with ethyl acetate. The resultant was washed with water 2 times, the organic layer was washed with saturated aqueous sodium bicarbonate solution and saturated saline, dried over anhydrous magnesium sulfate, and concentrated. The residue was subjected to silica gel column chromatography to obtain 3.67 g of 5-fluoro-2-(3-methoxyphenoxy)-4-[3-methyl-2,6-dioxo-4-(trifluoromethyl)-1,2,3,6-tetrahydropyrimidin-1-yl]aniline.

$^1$H-NMR (CDCl$_3$/300 MHz) δ (ppm): 3.52 (q, 3H, J=1.0 Hz), 3.76 (s, 3H), 4.0–4.2 (b, 2H), 6.31 (s, 1H), 6.5–6.7 (m, 4H), 6.73 (d, 1H, J=7.0 Hz), 7.1–7.3 (m, 1H)

Third process:
To a mixture of 213 mg of 5-fluoro-2-(3-methoxyphenoxy)-4-[3-methyl-2,6-dioxo-4-(trifluoromethyl)-1,2,3,6-tetrahydropyrimidin-1-yl]aniline, 93 mg of copper (I) bromide and 1 ml of acetonitrile, 57 mg of t-butyl nitrite was added dropwise over 1 hour at 0° C. The mixture was stirred for 30 minutes, then, stirred at room temperature and stirred for 10 hours. The reaction mixture was poured into 2% hydrochloric acid and extracted with ethyl acetate. The organic layer was washed with saturated saline, dried over anhydrous magnesium sulfate, and concentrated. The residue was subjected to silica gel column chromatography to obtain 75 mg of 5-fluoro-2-(3-methoxyphenoxy)-4-[3-methyl-2,6-dioxo-4-(trifluoromethyl)-1,2,3,6-tetrahydropyrimidin-1-yl]bromobenzene.

$^1$H-NMR (CDCl$_3$/300 MHz) δ (ppm): 3.52 (q, 3H, J=1.2 Hz), 3.77 (s, 3H), 6.31 (s, 1H), 6.5–6.6 (m, 1H), 6.59 (s. 1H), 6.6–6.7 (m, 1H), 6.86 (d, 1H, J=6.7 Hz), 7.22 (dd, 1H, J=9.0, 8.7 Hz), 7.54 (d, 1H, J=8.8 Hz)

Forth Process:
A mixture of 75 mg of 5-fluoro-2-(3-methoxyphenoxy)-4-[3-methyl-2,6-dioxo-4-(trifluoromethyl)-1,2,3,6-tetrahydropyrimidin-1-yl]bromobenzene, 27 mg of copper cyanide and 0.5 ml of N-methyl-2-pyrrolidone was stirred at 170 to 180° C. for 2 hours. The reaction mixture was cooled to room temperature, water was added to the mixture and the resultant was extracted with ethyl acetate. The organic layer was dried over anhydrous magnesium sulfate, and concentrated. The residue was subjected to silica gel column chromatography to obtain 57 mg of 5-fluoro-2-(3-methoxyphenoxy)-4-[3-methyl-2,6-dioxo-4-(trifluoromethyl)-1,2,3,6-tetrahydropyrimidin-1 -yl]cyanobenzene.

$^1$H-NMR (CDCl$_3$/300 MHz) δ (ppm): 3.52 (q, 3H, J=1.0 Hz), 3.79 (s, 3H), 6.31 (s, 1H), 6.31 (s. 1H), 6.67 (s, 1H), 6.6–6.7 (m, 1H), 6.7–6.8 (m, 1H), 6.84 (d, 1H, J=5.8 Hz), 7.29 (dd, 1H, J=9.1, 8.6 Hz), 7.53 (d, 1H, J=8.4 Hz)

Fifth Process:
To a solution of 57 mg of 5-fluoro-2-(3-methoxyphenoxy)-4-[3-methyl-2,6-dioxo-4-(trifluoromethyl)-1,2,3,6-tetrahydropyrimidin-1-yl]cyanobenzene in 0.6 ml of chloroform, 48 µl of boron tribromide was added dropwise at 0° C. After the addition, the temperature of the reaction mixture was raised to room temperature and stirred for 1 hour. The mixture was cooled to 0° C. and 1 ml of methanol was added thereto. The solvent was removed under reduced pressure, the resultant was diluted with ethyl acetate, and then, saturated aqueous sodium bicarbonate solution was added thereto to be pH 4. The resultant was extracted with ethyl acetate. The organic layer was washed with saturated saline, dried over anhydrous magnesium sulfate, and concentrated. The residue was subjected to silica gel column chromatography to obtain 36 mg of 3-{2-cyano-4-fluoro-5-[3-methyl-2,6-dioxo-4-(trifluoromethyl)-1,2,3,6-tetrahydropyrimidin-1-yl]phenoxy}phenol.

$^1$H-NMR (CDCl$_3$/300 MHz) δ (ppm): 3.52 (q, 3H, J=1.0 Hz), 6.32 (s, 1H), 6.3–6.5 (b, 1H), 6.5–6.6 (m, 1H), 6.6–6.7 (m, 2H), 6.87 (d, 1H, J=5.8 Hz), 7.21 (dd, 1H, J=8.3, 8.1 Hz), 7.51 (d, 1H, J=8.4 Hz)

INTERMEDIATE PRODUCTION EXAMPLE 10
Production of 5-fluoro-2-{2-(methoxycarbonyl)methoxyphenoxy}-4-[3-methyl-2,6-dioxo-4-(trifluoromethyl)-1,2,3,6-tetrahydropyrimidin-1-yl]aniline To a solution of 19 g of iron powder, 60 ml of acetic acid and 6 ml of water, a solution of 19.12 g of 5-fluoro-2-{2-(methoxycarbonyl)methoxyphenoxy}-4-[3-methyl-2,6-dioxo-4-(trifluoromethyl)-1,2,3,6-tetrahydropyrimidin-1-yl]nitrobenzene [Compound 4-19 of the present invention] in 60 ml of acetic acid was added dropwise under ice cooling. After the addition, the temperature of the reaction mixture was raised to room temperature and the mixture was stirred for 4 hours. The reaction mixture was filtered with sellaite and diluted with ethyl acetate. The dilution was washed with water, saturated aqueous sodium bicarbonate solution and saturated saline, dried over anhydrous magnesium sulfate, and concentrated. The residue was subjected to silica gel column chromatography to obtain 15.16 g of 5-fluoro-2-{2-(methoxycarbonyl)methoxyphenoxy}-4-[3-methyl-2,6-dioxo-4-(trifluoromethyl)-1,2,3,6-tetrahydropyrimidin-1-yl]aniline.

$^1$H-NMR (CDCl$_3$/250 MHz) δ (ppm): 3.51 (q, 3H, J=0.9 Hz), 3.76 (s, 3H), 4.2–4.4 (b, 2H), 4.69 (s, 2H), 6.29 (s, 1H), 6.6–6.7 (m, 2H), 6.9–7.1 (m, 4H)

INTERMEDIATE PRODUCTION EXAMPLE 11
Production of methyl [2-(2-chloro-4-fluoro-5-methoxycarbonylaminophenoxy)phenoxy]acetate [Intermediate compound A9-22]

First Process:

4-chloro-2-fluoro-5-(2-hydroxyphenoxy)aniline [Intermediate Compound A3-4] was produced from N-[4-chloro-2-fluoro-5-(2-hydroxyphenoxy)phenyl]acetamide (produced in Intermediate Production Example 6, Third Process) according to the process of Sixth Process of Intermediate Production Example 5.

$^1$H-NMR (CDCl$_3$/300 MHz) δ (ppm): 3.76 (bs, 2H), 5.78 (bs, 1H), 6.41 (d, 1H, J=8.3 Hz), 6.7–6.9 (m, 2H), 7.0–7.1 (m, 2H), 7.09 (d, 1H, J=10.2 Hz)

Second process:

Into a mixture of 4-chloro-2-fluoro-5-(2-hydroxyphenoxy)aniline [Intermediate Compound A3-4], methyl chloroformate and tetrahydrofuran is added dropwise N,N-dimethylaniline, and the mixture is stirred at room temperature. Dilute hydrochloric acid is added to the reaction solution, and this is extracted with ethyl acetate. The organic layer is washed with saturated saline, dried over anhydrous magnesium sulfate, and concentrated to obtain 2-(2-chloro-4-fluoro-5-methoxycarbonylaminophenoxy)phenol [Intermediate compound A9-4].

Third process:

2-(2-chloro-4-fluoro-5-methoxycarbonylaminophenoxy)phenol [Intermediate compound A9-4] is dissolved in N,N-dimethylformamide, then, potassium carbonate is added, and the mixture is stirred for 1 hour at room temperature. Then, methyl bromoacetate is added at room temperature. The mixture is stirred at 60° C. for 2 hours, poured into water, extracted with ethyl acetate, and the organic layer is washed with dilute hydrochloric acid and water, dried over magnesium sulfate and concentrated to obtain methyl [2-(2-chloro-4-fluoro-5-methoxycarbonylaminophenoxy)phenoxy]acetate [Intermediate compound A9-22].

Next, some compounds of the present invention will be exemplified. Specific compounds are specified by compound numbers described in Tables 1 to 5. The compounds of the present invention are not limited to these exemplified compounds.

Compound [I-1] (compound numbers are described in Table 1)

TABLE 1

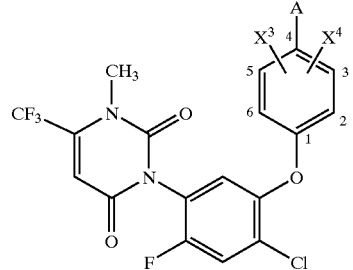

[I-1]

| Compound No | X$^3$ | X$^4$ | A |
|---|---|---|---|
| 1-1 | H | H | OCH(CH$_3$)CO$_2$CH$_3$ |
| 1-2 | H | H | OCH(CH$_3$)CO$_2$CH$_2$CH$_3$ |
| 1-3 | H | H | OCH(CH$_3$)CO$_2$CH$_2$CH$_2$CH$_3$ |
| 1-4 | H | H | OCH(CH$_3$)CO$_2$CH$_2$CH$_2$CH$_2$CH$_3$ |
| 1-5 | H | H | OCH(CH$_3$)CO$_2$CH(CH$_3$)$_2$ |
| 1-6 | H | H | OCH(CH$_3$)CO$_2$C(CH$_3$)$_3$ |
| 1-7 | H | H | OCH(CH$_3$)CO$_2$CH$_2$CH$_2$F |
| 1-8 | H | H | OCH(CH$_3$)CO$_2$CH$_2$CH$_2$Cl |
| 1-9 | H | H | OCH(CH$_3$)CO$_2$CH$_2$CCl$_3$ |
| 1-10 | H | H | OCH(CH$_3$)CO$_2$CH$_2$CH=CH$_2$ |
| 1-11 | H | H | OCH$_2$CO$_2$CH$_3$ |

TABLE 1-continued

[I-1]

| Compound No | X$^3$ | X$^4$ | A |
|---|---|---|---|
| 1-12 | H | H | OCH$_2$CO$_2$CH$_2$CH$_3$ |
| 1-13 | H | H | OCH$_2$CO$_2$CH$_2$CH$_2$CH$_3$ |
| 1-14 | H | H | OCH$_2$CO$_2$CH$_2$CH$_2$CH$_2$CH$_3$ |
| 1-15 | H | H | OCH$_2$CO$_2$CH(CH$_3$)$_2$ |
| 1-16 | H | H | OCH$_2$CO$_2$C(CH$_3$)$_3$ |
| 1-17 | H | H | OCH$_2$CO$_2$CH$_2$CH$_2$F |
| 1-18 | H | H | OCH$_2$CO$_2$CH$_2$CH$_2$Cl |
| 1-19 | H | H | OCH$_2$CO$_2$CH$_2$CCl$_3$ |
| 1-20 | H | H | OCH$_2$CO$_2$CH$_2$CH=CH$_2$ |
| 1-21 | H | H | SCH(CH$_3$)CO$_2$CH$_3$ |
| 1-22 | H | H | SCH(CH$_3$)CO$_2$CH$_2$CH$_3$ |
| 1-23 | H | H | SCH(CH$_3$)CO$_2$CH$_2$CH$_2$CH$_3$ |
| 1-24 | H | H | SCH(CH$_3$)CO$_2$CH$_2$CH$_2$CH$_3$ |
| 1-25 | H | H | SCH(CH$_3$)CO$_2$CH(CH$_3$)$_2$ |
| 1-26 | H | H | SCH(CH$_3$)CO$_2$C(CH$_3$)$_3$ |
| 1-27 | H | H | SCH(CH$_3$)CO$_2$CH$_2$CH$_2$F |
| 1-28 | H | H | SCH(CH$_3$)CO$_2$CH$_2$CH$_2$Cl |
| 1-29 | H | H | SCH(CH$_3$)CO$_2$CH$_2$CCl$_3$ |
| 1-30 | H | H | SCH(CH$_3$)CO$_2$CH$_2$CH=CH$_2$ |
| 1-31 | H | H | SCH$_2$CO$_2$CH$_3$ |
| 1-32 | H | H | SCH$_2$CO$_2$CH$_2$CH$_3$ |
| 1-33 | H | H | SCH$_2$CO$_2$CH$_2$CH$_2$CH$_3$ |
| 1-34 | H | H | SCH$_2$CO$_2$CH$_2$CH$_2$CH$_2$CH$_3$ |
| 1-35 | H | H | SCH$_2$CO$_2$CH(CH$_3$)$_2$ |
| 1-36 | H | H | SCH$_2$CO$_2$C(CH$_3$)$_3$ |
| 1-37 | H | H | SCH$_2$CO$_2$CH$_2$CH$_2$F |
| 1-38 | H | H | SCH$_2$CO$_2$CH$_2$CH$_2$Cl |
| 1-39 | H | H | SCH$_2$CO$_2$CH$_2$CCl$_3$ |
| 1-40 | H | H | SCH$_2$CO$_2$CH$_2$CH=CH$_2$ |
| 1-41 | 3-CH$_3$ | H | OCH(CH$_3$)CO$_2$CH$_3$ |
| 1-42 | 3-CH$_3$ | H | OCH(CH$_3$)CO$_2$CH$_2$CH$_3$ |
| 1-43 | 3-CH$_3$ | H | OCH(CH$_3$)CO$_2$CH$_2$CH$_2$CH$_3$ |
| 1-44 | 3-CH$_3$ | H | OCH(CH$_3$)CO$_2$CH$_2$CH$_2$CH$_2$CH$_3$ |
| 1-45 | 3-CH$_3$ | H | OCH(CH$_3$)CO$_2$CH(CH$_3$)$_2$ |
| 1-46 | 3-CH$_3$ | H | OCH(CH$_3$)CO$_2$C(CH$_3$)$_3$ |
| 1-47 | 3-CH$_3$ | H | OCH(CH$_3$)CO$_2$CH$_2$CH$_2$F |
| 1-48 | 3-CH$_3$ | H | OCH(CH$_3$)CO$_2$CH$_2$CH$_2$Cl |
| 1-49 | 3-CH$_3$ | H | OCH(CH$_3$)CO$_2$CH$_2$CCl$_3$ |
| 1-50 | 3-CH$_3$ | H | OCH(CH$_3$)CO$_2$CH$_2$CH=CH$_2$ |
| 1-51 | 3-CH$_3$ | H | OCH$_2$CO$_2$CH$_3$ |
| 1-52 | 3-CH$_3$ | H | OCH$_2$CO$_2$CH$_2$CH$_3$ |
| 1-53 | 3-CH$_3$ | H | OCH$_2$CO$_2$CH$_2$CH$_2$CH$_3$ |
| 1-54 | 3-CH$_3$ | H | OCH$_2$CO$_2$CH$_2$CH$_2$CH$_2$CH$_3$ |
| 1-55 | 3-CH$_3$ | H | OCH$_2$CO$_2$CH(CH$_3$)$_2$ |
| 1-56 | 3-CH$_3$ | H | OCH$_2$CO$_2$C(CH$_3$)$_3$ |
| 1-57 | 3-CH$_3$ | H | OCH$_2$CO$_2$CH$_2$CH$_2$F |
| 1-58 | 3-CH$_3$ | H | OCH$_2$CO$_2$CH$_2$CH$_2$Cl |
| 1-59 | 3-CH$_3$ | H | OCH$_2$CO$_2$CH$_2$CCl$_3$ |
| 1-60 | 3-CH$_3$ | H | OCH$_2$CO$_2$CH$_2$CH=CH$_2$ |
| 1-61 | 2-CH$_3$ | H | OCH(CH$_3$)CO$_2$CH$_2$CH$_2$CH$_3$ |
| 1-62 | 2-CH$_3$ | H | OCH(CH$_3$)CO$_2$CH$_3$ |
| 1-63 | 2-CH$_3$ | H | OCH(CH$_3$)CO$_2$CH$_2$CH$_3$ |
| 1-64 | 2-CH$_3$ | H | OCH(CH$_3$)CO$_2$CH$_2$CH$_2$CH$_3$ |
| 1-65 | 2-CH$_3$ | H | OCH(CH$_3$)CO$_2$CH(CH$_3$)$_2$ |
| 1-66 | 2-CH$_3$ | H | OCH(CH$_3$)CO$_2$C(CH$_3$)$_3$ |
| 1-67 | 2-CH$_3$ | H | OCH(CH$_3$)CO$_2$CH$_2$CH$_2$F |
| 1-68 | 2-CH$_3$ | H | OCH(CH$_3$)CO$_2$CH$_2$CH$_2$Cl |
| 1-69 | 2-CH$_3$ | H | OCH(CH$_3$)CO$_2$CH$_2$CCl$_3$ |
| 1-70 | 2-CH$_3$ | H | OCH(CH$_3$)CO$_2$CH$_2$CH=CH$_2$ |
| 1-71 | 2-CH$_3$ | H | OCH$_2$CO$_2$CH$_2$CH$_2$CH$_3$ |
| 1-72 | 2-CH$_3$ | H | OCH$_2$CO$_2$CH$_3$ |

TABLE 1-continued

[I-1]

| Compound No | X³ | X⁴ | A |
|---|---|---|---|
| 1-73 | 2-CH₃ | H | OCH₂CO₂CH₂CH₃ |
| 1-74 | 2-CH₃ | H | OCH₂CO₂CH₂CH₂CH₃ |
| 1-75 | 2-CH₃ | H | OCH₂CO₂CH(CH₃)₂ |
| 1-76 | 2-CH₃ | H | OCH₂CO₂C(CH₃)₃ |
| 1-77 | 2-CH₃ | H | OCH₂CO₂CH₂CH₂F |
| 1-78 | 2-CH₃ | H | OCH₂CO₂CH₂CH₂Cl |
| 1-79 | 2-CH₃ | H | OCH₂CO₂CH₂CCl₃ |
| 1-80 | 2-CH₃ | H | OCH₂CO₂CH₂CH=CH₂ |
| 1-81 | 3-OCH₃ | H | OCH(CH₃)CO₂CH₃ |
| 1-82 | 3-OCH₃ | H | OCH(CH₃)CO₂CH₂CH₃ |
| 1-83 | 3-OCH₃ | H | OCH(CH₃)CO₂CH₂CH₂CH₃ |
| 1-84 | 3-OCH₃ | H | OCH(CH₃)CO₂CH₂CH₂CH₂CH₃ |
| 1-85 | 3-OCH₃ | H | OCH(CH₃)CO₂CH(CH₃)₂ |
| 1-86 | 3-OCH₃ | H | OCH(CH₃)CO₂C(CH₃)₃ |
| 1-87 | 3-OCH₃ | H | OCH(CH₃)CO₂CH₂CH₂F |
| 1-88 | 3-OCH₃ | H | OCH(CH₃)CO₂CH₂CH₂Cl |
| 1-89 | 3-OCH₃ | H | OCH(CH₃)CO₂CH₂CCl₃ |
| 1-90 | 3-OCH₃ | H | OCH(CH₃)CO₂CH₂CH=CH₂ |
| 1-91 | 3-OCH₃ | H | OCH₂CO₂CH₃ |
| 1-92 | 3-OCH₃ | H | OCH₂CO₂CH₂CH₃ |
| 1-93 | 3-OCH₃ | H | OCH₂CO₂CH₂CH₂CH₃ |
| 1-94 | 3-OCH₃ | H | OCH₂CO₂CH₂CH₂CH₂CH₃ |
| 1-95 | 3-OCH₃ | H | OCH₂CO₂CH(CH₃)₂ |
| 1-96 | 3-OCH₃ | H | OCH₂CO₂C(CH₃)₃ |
| 1-97 | 3-OCH₃ | H | OCH₂CO₂CH₂CH₂F |
| 1-98 | 3-OCH₃ | H | OCH₂CO₂CH₂CH₂Cl |
| 1-99 | 3-OCH₃ | H | OCH₂CO₂CH₂CCl₃ |
| 1-100 | 3-OCH₃ | H | OCH₂CO₂CH₂CH=CH₂ |
| 1-101 | 2-OCH₃ | H | OCH(CH₃)CO₂CH₃ |
| 1-102 | 2-OCH₃ | H | OCH(CH₃)CO₂CH₂CH₃ |
| 1-103 | 2-OCH₃ | H | OCH(CH₃)CO₂CH₂CH₂CH₃ |
| 1-104 | 2-OCH₃ | H | OCH(CH₃)CO₂CH₂CH₂CH₂CH₃ |
| 1-105 | 2-OCH₃ | H | OCH(CH₃)CO₂CH(CH₃)₂ |
| 1-106 | 2-OCH₃ | H | OCH(CH₃)CO₂C(CH₃)₃ |
| 1-107 | 2-OCH₃ | H | OCH(CH₃)CO₂CH₂CH₂F |
| 1-108 | 2-OCH₃ | H | OCH(CH₃)CO₂CH₂CH₂Cl |
| 1-109 | 2-OCH₃ | H | OCH(CH₃)CO₂CH₂CCl₃ |
| 1-110 | 2-OCH₃ | H | OCH(CH₃)CO₂CH₂CH=CH₂ |
| 1-111 | 2-OCH₃ | H | OCH₂CO₂CH₃ |
| 1-112 | 2-OCH₃ | H | OCH₂CO₂CH₂CH₃ |
| 1-113 | 2-OCH₃ | H | OCH₂CO₂CH₂CH₂CH₃ |
| 1-114 | 2-OCH₃ | H | OCH₂CO₂CH₂CH₂CH₂CH₃ |
| 1-115 | 2-OCH₃ | H | OCH₂CO₂CH(CH₃)₂ |
| 1-116 | 2-OCH₃ | H | OCH₂CO₂C(CH₃)₃ |
| 1-117 | 2-OCH₃ | H | OCH₂CO₂CH₂CH₃F |
| 1-118 | 2-OCH₃ | H | OCH₂CO₂CH₂CH₂Cl |
| 1-119 | 2-OCH₃ | H | OCH₂CO₂CH₂CCl₃ |
| 1-120 | 2-OCH₃ | H | OCH₂CO₂CH₂CH=CH₂ |
| 1-121 | 3-Cl | H | OCH(CH₃)CO₂CH₃ |
| 1-122 | 3-Cl | H | OCH(CH₃)CO₂CH₂CH₃ |
| 1-123 | 3-Cl | H | OCH(CH₃)CO₂CH₂CH₂CH₃ |
| 1-124 | 3-Cl | H | OCH(CH₃)CO₂CH₂CH₂CH₂CH₃ |
| 1-125 | 3-Cl | H | OCH(CH₃)CO₂CH(CH₃)₂ |
| 1-126 | 3-Cl | H | OCH(CH₃)CO₂C(CH₃)₃ |
| 1-127 | 3-Cl | H | OCH(CH₃)CO₂CO₂CH₂F |
| 1-128 | 3-Cl | H | OCH(CH₃)CO₂CH₂CH₂Cl |
| 1-129 | 3-Cl | H | OCH(CH₃)CO₂CH₂CCl₃ |
| 1-130 | 3-Cl | H | OCH(CH₃)CO₂CH₂CH=CH₂ |
| 1-131 | 3-Cl | H | OCH₂CO₂CH₃ |
| 1-132 | 3-Cl | H | OCH₂CO₂CH₂CH₃ |
| 1-133 | 3-Cl | H | OCH₂CO₂CH₂CH₂CH₃ |
| 1-134 | 3-Cl | H | OCH₂CO₂CH₂CH₂CH₂CH₃ |
| 1-135 | 3-Cl | H | OCH₂CO₂CH(CH₃)₂ |
| 1-136 | 3-Cl | H | OCH₂CO₂C(CH₃)₃ |
| 1-137 | 3-Cl | H | OCH₂CO₂CH₂CH₂F |
| 1-138 | 3-Cl | H | OCH₂CO₂CH₂CH₂Cl |
| 1-139 | 3-Cl | H | OCH₂CO₂CH₂CCl₃ |
| 1-140 | 3-Cl | H | OCH₂CO₂CH₂CH=CH₂ |
| 1-141 | 2-Cl | H | OCH(CH₃)CO₂CH₃ |
| 1-142 | 2-Cl | H | OCH(CH₃)CO₂CH₂CH₃ |
| 1-143 | 2-Cl | H | OCH(CH₃)CO₂CH₂CH₂CH₃ |
| 1-144 | 2-Cl | H | OCH(CH₃)CO₂CH₂CH₂CH₂CH₃ |
| 1-145 | 2-Cl | H | OCH(CH₃)CO₂CH(CH₃)₂ |
| 1-146 | 2-Cl | H | OCH(CH₃)CO₂C(CH₃)₃ |
| 1-147 | 2-Cl | H | OCH(CH₃)CO₂CH₂CH₂F |
| 1-148 | 2-Cl | H | OCH(CH₃)CO₂CH₂CH₂Cl |
| 1-149 | 2-Cl | H | OCH(CH₃)CO₂CH₂CCl₃ |
| 1-150 | 2-Cl | H | OCH(CH₃)CO₂CH₂CH=CH₂ |
| 1-151 | 2-Cl | H | OCH₂CO₂CH₃ |
| 1-152 | 2-Cl | H | OCH₂CO₂CH₂CH₃ |
| 1-153 | 2-Cl | H | OCH₂CO₂CH₂CH₂CH₃ |
| 1-154 | 2-Cl | H | OCH₂CO₂CH₂CH₂CH₂CH₃ |
| 1-155 | 2-Cl | H | OCH₂CO₂CH(CH₃)₂ |
| 1-156 | 2-Cl | H | OCH₂CO₂C(CH₃)₃ |
| 1-157 | 2-Cl | H | OCH₂CO₂CH₂CH₂F |
| 1-158 | 2-Cl | H | OCH₂CO₂CH₂CH₂Cl |
| 1-159 | 2-Cl | H | OCH₂CO₂CH₂CCl₃ |
| 1-160 | 2-Cl | H | OCH₂CO₂CH₂CH=CH₂ |
| 1-161 | H | H | NHCH(CH₃)CO₂CH₃ |
| 1-162 | H | H | NHCH(CH₃)CO₂CH₂CH₃ |
| 1-163 | H | H | NHCH(CH₃)CO₂CH₂CH₂CH₃ |
| 1-164 | H | H | NHCH(CH₃)CO₂CH₂CH₂CH₂CH₃ |
| 1-165 | H | H | NHCH(CH₃)CO₂CH(CH₃)₂ |
| 1-166 | H | H | NHCH(CH₃)CO₂C(CH₃)₃ |
| 1-167 | H | H | NHCH(CH₃)CO₂CH₂CH₂F |
| 1-168 | H | H | NHCH(CH₃)CO₂CH₂CH₂Cl |
| 1-169 | H | H | NHCH(CH₃)CO₂CH₂CCl₃ |
| 1-170 | H | H | NHCH(CH₃)CO₂CH₂CH=CH₂ |
| 1-171 | H | H | NHCH₂CO₂CH₃ |
| 1-172 | H | H | NHCH₂CO₂CH₂CH₃ |
| 1-173 | H | H | NHCH₂CO₂CH₂CH₂CH₃ |
| 1-174 | H | H | NHCH₂CO₂CH₂CH₂CH₂CH₃ |
| 1-175 | H | H | NHCH₂CO₂CH(CH₃)₂ |
| 1-176 | H | H | NHCH₂CO₂C(CH₃)₃ |
| 1-177 | H | H | NHCH₂CO₂CH₂CH₂F |
| 1-178 | H | H | NHCH₂CO₂CH₂CH₂Cl |
| 1-179 | H | H | NHCH₂CO₂CH₂CCl₃ |
| 1-180 | H | H | NHCH₂CO₂CH₂CH=CH₂ |
| 1-181 | H | H | N(CH₃)CH(CH₃)CO₂CH₃ |
| 1-182 | H | H | N(CH₃)CH(CH₃)CO₂CH₂CH₃ |
| 1-183 | H | H | N(CH₃)CH₂CO₂CH₃ |
| 1-184 | H | H | N(CH₃)CH₂CO₂CH₂CH₃ |
| 1-185 | H | H | N(CH₃)CH₂CO₂CH₂CH₂CH₃ |
| 1-186 | H | H | OCH(CH₃)CO₂CH₂CH₂CH=CH₂ |
| 1-187 | H | H | OCH(CH₃)CO₂CH₂CH(CH₃)₂ |
| 1-188 | H | H | OCH(CH₃)CO₂CH(CH₃)CH₂CH₃ |
| 1-189 | H | H | OCH(CH₃)CO₂CH₂CH₂CH₂CH₂CH₃ |
| 1-190 | H | H | OCH(CH₃)CO₂CH₂CH₂CH(CH₃)₂ |
| 1-191 | H | H | OCH(CH₃)CO₂CH₂CH(CH₃)CH₂CH₃ |
| 1-192 | H | H | OCH(CH₃)CO₂CH(CH₃)CH₂CH₂CH₃ |
| 1-193 | H | H | OCH(CH₃)CO₂C(CH₃)₂CH₂CH₃ |
| 1-194 | H | H | OCH(CH₃)CO₂CH(CH₃)CH(CH₃)₂ |

TABLE 1-continued

[I-1]

| Compound No | X³ | X⁴ | A |
|---|---|---|---|
| 1-195 | H | H | OCH($CH_3$)$CO_2CH_2C(CH_3)_3$ |
| 1-196 | H | H | OCH($CH_3$)$CO_2CH_2C\equiv CH$ |
| 1-197 | H | H | OCH($CH_3$)$CO_2CH_2CH_2CH=CH_2$ |
| 1-198 | H | H | OCH$_2CO_2CH_2CH(CH_3)_2$ |
| 1-199 | H | H | OCH$_2CO_2CH(CH_3)CH_2CH_3$ |
| 1-200 | H | H | OCH$_2CO_2CH_2CH_2CH_2CH_2CH_3$ |
| 1-201 | H | H | OCH$_2CO_2CH_2C\equiv CH$ |

Compound of the general formula [I-2] (compound numbers are described in Table 2)

TABLE 2

[I-2]

| Compound No | X³ | X⁴ | A |
|---|---|---|---|
| 2-1 | H | H | OCH($CH_3$)$CO_2CH_3$ |
| 2-2 | H | H | OCH($CH_3$)$CO_2CH_2CH_3$ |
| 2-3 | H | H | OCH($CH_3$)$CO_2CH_2CH_2CH_3$ |
| 2-4 | H | H | OCH($CH_3$)$CO_2CH_2CH_2CH_2CH_3$ |
| 2-5 | H | H | OCH($CH_3$)$CO_2CH(CH_3)_2$ |
| 2-6 | H | H | OCH($CH_3$)$CO_2C(CH_3)_3$ |
| 2-7 | H | H | OCH($CH_3$)$CO_2CH_2CH_2F$ |
| 2-8 | H | H | OCH($CH_3$)$CO_2CH_2CH_2Cl$ |
| 2-9 | H | H | OCH($CH_3$)$CO_2CH_2CCl_3$ |
| 2-10 | H | H | OCH($CH_3$)$CO_2CH_2CH=CH_2$ |
| 2-11 | H | H | OCH$_2CO_2CH_3$ |
| 2-12 | H | H | OCH$_2CO_2CH_2CH_3$ |
| 2-13 | H | H | OCH$_2CO_2CH_2CH_2CH_3$ |
| 2-14 | H | H | OCH$_2CO_2CH_2CH_2CH_2CH_3$ |
| 2-15 | H | H | OCH$_2CO_2CH(CH_3)_2$ |
| 2-16 | H | H | OCH$_2CO_2C(CH_3)_3$ |
| 2-17 | H | H | OCH$_2CO_2CH_2CH_2F$ |
| 2-18 | H | H | OCH$_2CO_2CH_2CH_2Cl$ |
| 2-19 | H | H | OCH$_2CO_2CH_2CCl_3$ |
| 2-20 | H | H | OCH$_2CO_2CH_2CH=CH_2$ |
| 2-21 | H | H | SCH($CH_3$)$CO_2CH_3$ |
| 2-22 | H | H | SCH($CH_3$)$CO_2CH_2CH_3$ |
| 2-23 | H | H | SCH($CH_3$)$CO_2CH_2CH_2CH_2CH_3$ |
| 2-24 | H | H | SCH($CH_3$)$CO_2CH_2CH_2CH_3$ |
| 2-25 | H | H | SCH($CH_3$)$CO_2CH(CH_3)_2$ |
| 2-26 | H | H | SCH($CH_3$)$CO_2C(CH_3)_3$ |
| 2-27 | H | H | SCH($CH_3$)$CO_2CH_2CH_2F$ |
| 2-28 | H | H | SCH($CH_3$)$CO_2CH_2CH_2Cl$ |
| 2-29 | H | H | SCH($CH_3$)$CO_2CH_2CCl_3$ |
| 2-30 | H | H | SCH($CH_3$)$CO_2CH_2CH=CH_2$ |
| 2-31 | H | H | SCH$_2CO_2CH_3$ |

TABLE 2-continued

[I-2]

| Compound No | X³ | X⁴ | A |
|---|---|---|---|
| 2-32 | H | H | SCH$_2CO_2CH_2CH_3$ |
| 2-33 | H | H | SCH$_2CO_2CH_2CH_2CH_3$ |
| 2-34 | H | H | SCH$_2CO_2CH_2CH_2CH_2CH_3$ |
| 2-35 | H | H | SCH$_2CO_2CH(CH_3)_2$ |
| 2-36 | H | H | SCH$_2CO_2C(CH_3)_3$ |
| 2-37 | H | H | SCH$_2CO_2CH_2CH_2F$ |
| 2-38 | H | H | SCH$_2CO_2CH_2CH_2Cl$ |
| 2-39 | H | H | SCH$_2CO_2CH_2CCl_3$ |
| 2-40 | H | H | SCH$_2CO_2CH_2CH=CH_2$ |
| 2-41 | 4-$CH_3$ | H | OCH($CH_3$)$CO_2CH_3$ |
| 2-42 | 4-$CH_3$ | H | OCH($CH_3$)$CO_2CH_2CH_3$ |
| 2-43 | 4-$CH_3$ | H | OCH($CH_3$)$CO_2CH_2CH_2CH_3$ |
| 2-44 | 4-$CH_3$ | H | OCH($CH_3$)$CO_2CH_2CH_2CH_2CH_3$ |
| 2-45 | 4-$CH_3$ | H | OCH($CH_3$)$CO_2CH(CH_3)_2$ |
| 2-46 | 4-$CH_3$ | H | OCH($CH_3$)$CO_2C(CH_3)_3$ |
| 2-47 | 4-$CH_3$ | H | OCH($CH_3$)$CO_2CH_2CH_2F$ |
| 2-48 | 4-$CH_3$ | H | OCH($CH_3$)$CO_2CH_2CH_2Cl$ |
| 2-49 | 4-$CH_3$ | H | OCH($CH_3$)$CO_2CH_2CCl_3$ |
| 2-50 | 4-$CH_3$ | H | OCH($CH_3$)$CO_2CH_2CH=CH_2$ |
| 2-51 | 4-$CH_3$ | H | OCH$_2CO_2CH_3$ |
| 2-52 | 4-$CH_3$ | H | OCH$_2CO_2CH_2CH_3$ |
| 2-53 | 4-$CH_3$ | H | OCH$_2CO_2CH_2CH_2CH_3$ |
| 2-54 | 4-$CH_3$ | H | OCH$_2CO_2CH_2CH_2CH_2CH_3$ |
| 2-55 | 4-$CH_3$ | H | OCH$_2CO_2CH(CH_3)_2$ |
| 2-56 | 4-$CH_3$ | H | OCH$_2CO_2C(CH_3)_3$ |
| 2-57 | 4-$CH_3$ | H | OCH$_2CO_2CH_2CH_2F$ |
| 2-58 | 4-$CH_3$ | H | OCH$_2CO_2CH_2CH_2Cl$ |
| 2-59 | 4-$CH_3$ | H | OCH$_2CO_2CH_2CCl_3$ |
| 2-60 | 4-$CH_3$ | H | OCH$_2CO_2CH_2CH=CH_2$ |
| 2-61 | 2-$CH_3$ | H | OCH($CH_3$)$CO_2CH_2CH_2CH_3$ |
| 2-62 | 2-$CH_3$ | H | OCH($CH_3$)$CO_2CH_3$ |
| 2-63 | 2-$CH_3$ | H | OCH($CH_3$)$CO_2CH_2CH_3$ |
| 2-64 | 2-$CH_3$ | H | OCH($CH_3$)$CO_2CH_2CH_2CH_3$ |
| 2-65 | 2-$CH_3$ | H | OCH($CH_3$)$CO_2CH(CH_3)_2$ |
| 2-66 | 2-$CH_3$ | H | OCH($CH_3$)$CO_2C(CH_3)_3$ |
| 2-67 | 2-$CH_3$ | H | OCH($CH_3$)$CO_2CH_2CH_2F$ |
| 2-68 | 2-$CH_3$ | H | OCH($CH_3$)$CO_2CH_2CH_2Cl$ |
| 2-69 | 2-$CH_3$ | H | OCH($CH_3$)$CO_2CH_2CCl_3$ |
| 2-70 | 2-$CH_3$ | H | OCH($CH_3$)$CO_2CH_2CH=CH_2$ |
| 2-71 | 2-$CH_3$ | H | OCH$_2CO_2CH_2CH_2CH_3$ |
| 2-72 | 2-$CH_3$ | H | OCH$_2CO_2CH_3$ |
| 2-73 | 2-$CH_3$ | H | OCH$_2CO_2CH_2CH_3$ |
| 2-74 | 2-$CH_3$ | H | OCH$_2CO_2CH_2CH_2CH_3$ |
| 2-75 | 2-$CH_3$ | H | OCH$_2CO_2CH(CH_3)_2$ |
| 2-76 | 2-$CH_3$ | H | OCH$_2CO_2C(CH_3)_3$ |
| 2-77 | 2-$CH_3$ | H | OCH$_2CO_2CH_2CH_2F$ |
| 2-78 | 2-$CH_3$ | H | OCH$_2CO_2CH_2CH_2Cl$ |
| 2-79 | 2-$CH_3$ | H | OCH$_2CO_2CH_2CCl_3$ |
| 2-80 | 2-$CH_3$ | H | OCH$_2CO_2CH_2CH=CH_2$ |
| 2-81 | 4-$OCH_3$ | H | OCH($CH_3$)$CO_2CH_3$ |
| 2-82 | 4-$OCH_3$ | H | OCH($CH_3$)$CO_2CH_2CH_3$ |
| 2-83 | 4-$OCH_3$ | H | OCH($CH_3$)$CO_2CH_2CH_2CH_3$ |
| 2-84 | 4-$OCH_3$ | H | OCH($CH_3$)$CO_2CH_2CH_2CH_2CH_3$ |
| 2-85 | 4-$OCH_3$ | H | OCH($CH_3$)$CO_2CH(CH_3)_2$ |
| 2-86 | 4-$OCH_3$ | H | OCH($CH_3$)$CO_2C(CH_3)_3$ |
| 2-87 | 4-$OCH_3$ | H | OCH($CH_3$)$CO_2CH_2CH_2F$ |
| 2-88 | 4-$OCH_3$ | H | OCH($CH_3$)$CO_2CH_2CH_2Cl$ |
| 2-89 | 4-$OCH_3$ | H | OCH($CH_3$)$CO_2CH_2CCl_3$ |
| 2-90 | 4-$OCH_3$ | H | OCH($CH_3$)$CO_2CH_2CH=CH_2$ |
| 2-91 | 4-$OCH_3$ | H | OCH$_2CO_2CH_3$ |
| 2-92 | 4-$OCH_3$ | H | OCH$_2CO_2CH_2CH_3$ |
| 2-93 | 4-$OCH_3$ | H | OCH$_2CO_2CH_2CH_2CH_3$ |

TABLE 2-continued

[I-2]

| Compound No | X³ | X⁴ | A |
|---|---|---|---|
| 2-94 | 4-OCH₃ | H | OCH₂CO₂CH₂CH₂CH₂CH₃ |
| 2-95 | 4-OCH₃ | H | OCH₂CO₂CH(CH₃)₂ |
| 2-96 | 4-OCH₃ | H | OCH₂CO₂C(CH₃)₃ |
| 2-97 | 4-OCH₃ | H | OCH₂CO₂CH₂CH₂F |
| 2-98 | 4-OCH₃ | H | OCH₂CO₂CH₂CH₂Cl |
| 2-99 | 4-OCH₃ | H | OCH₂CO₂CH₂CCl₃ |
| 2-100 | 4-OCH₃ | H | OCH₂CO₂CH₂CH=CH₂ |
| 2-101 | 2-OCH₃ | H | OCH(CH₃)CO₂CH₃ |
| 2-102 | 2-OCH₃ | H | OCH(CH₃)CO₂CH₂CH₃ |
| 2-103 | 2-OCH₃ | H | OCH(CH₃)CO₂CH₂CH₂CH₃ |
| 2-104 | 2-OCH₃ | H | OCH(CH₃)CO₂CH₂CH₂CH₂CH₃ |
| 2-105 | 2-OCH₃ | H | OCH(CH₃)CO₂CH(CH₃)₂ |
| 2-106 | 2-OCH₃ | H | OCH(CH₃)CO₂C(CH₃)₃ |
| 2-107 | 2-OCH₃ | H | OCH(CH₃)CO₂CH₂CH₂F |
| 2-108 | 2-OCH₃ | H | OCH(CH₃)CO₂CH₂CH₂Cl |
| 2-109 | 2-OCH₃ | H | OCH(CH₃)CO₂CH₂CCl₃ |
| 2-110 | 2-OCH₃ | H | OCH(CH₃)CO₂CH₂CH=CH₂ |
| 2-111 | 2-OCH₃ | H | OCH₂CO₂CH₃ |
| 2-112 | 2-OCH₃ | H | OCH₂CO₂CH₂CH₃ |
| 2-113 | 2-OCH₃ | H | OCH₂CO₂CH₂CH₂CH₃ |
| 2-114 | 2-OCH₃ | H | OCH₂CO₂CH₂CH₂CH₂CH₃ |
| 2-115 | 2-OCH₃ | H | OCH₂CO₂CH(CH₃)₂ |
| 2-116 | 2-OCH₃ | H | OCH₂CO₂C(CH₃)₃ |
| 2-117 | 2-OCH₃ | H | OCH₂CO₂CH₂CH₂F |
| 2-118 | 2-OCH₃ | H | OCH₂CO₂CH₂CH₂Cl |
| 2-119 | 2-OCH₃ | H | OCH₂CO₂CH₂CCl₃ |
| 2-120 | 2-OCH₃ | H | OCH₂CO₂CH₂CH=CH₂ |
| 2-121 | 4-Cl | H | OCH(CH₃)CO₂CH₃ |
| 2-122 | 4-Cl | H | OCH(CH₃)CO₂CH₂CH₃ |
| 2-123 | 4-Cl | H | OCH(CH₃)CO₂CH₂CH₂CH₃ |
| 2-124 | 4-Cl | H | OCH(CH₃)CO₂CH₂CH₂CH₂CH₃ |
| 2-125 | 4-Cl | H | OCH(CH₃)CO₂CH(CH₃)₂ |
| 2-126 | 4-Cl | H | OCH(CH₃)CO₂C(CH₃)₃ |
| 2-127 | 4-Cl | H | OCH(CH₃)CO₂CH₂CH₂F |
| 2-128 | 4-Cl | H | OCH(CH₃)CO₂CH₂CH₂Cl |
| 2-129 | 4-Cl | H | OCH(CH₃)CO₂CH₂CCl₃ |
| 2-130 | 4-Cl | H | OCH(CH₃)CO₂CH₂CH=CH₂ |
| 2-131 | 4-Cl | H | OCH₂CO₂CH₃ |
| 2-132 | 4-Cl | H | OCH₂CO₂CH₂CH₃ |
| 2-133 | 4-Cl | H | OCH₂CO₂CH₂CH₂CH₃ |
| 2-134 | 4-Cl | H | OCH₂CO₂CH₂CH₂CH₂CH₃ |
| 2-135 | 4-Cl | H | OCH₂CO₂CH(CH₃)₂ |
| 2-136 | 4-Cl | H | OCH₂CO₂C(CH₃)₃ |
| 2-137 | 4-Cl | H | OCH₂CO₂CH₂CH₂F |
| 2-138 | 4-Cl | H | OCH₂CO₂CH₂CH₂Cl |
| 2-139 | 4-Cl | H | OCH₂CO₂CH₂CCl₃ |
| 2-140 | 4-Cl | H | OCH₂CO₂CH₂CH=CH₂ |
| 2-141 | 2-Cl | H | OCH(CH₃)CO₂CH₃ |
| 2-142 | 2-Cl | H | OCH(CH₃)CO₂CH₂CH₃ |
| 2-143 | 2-Cl | H | OCH(CH₃)CO₂CH₂CH₂CH₃ |
| 2-144 | 2-Cl | H | OCH(CH₃)CO₂CH₂CH₂CH₂CH₃ |
| 2-145 | 2-Cl | H | OCH(CH₃)CO₂CH(CH₃)₂ |
| 2-146 | 2-Cl | H | OCH(CH₃)CO₂C(CH₃)₃ |
| 2-147 | 2-Cl | H | OCH(CH₃)CO₂CH₂CH₂F |
| 2-148 | 2-Cl | H | OCH(CH₃)CO₂CH₂CH₂Cl |
| 2-149 | 2-Cl | H | OCH(CH₃)CO₂CH₂CCl₃ |
| 2-150 | 2-Cl | H | OCH(CH₃)CO₂CH₂CH=CH₂ |
| 2-151 | 2-Cl | H | OCH₂CO₂CH₃ |
| 2-152 | 2-Cl | H | OCH₂CO₂CH₂CH₃ |
| 2-153 | 2-Cl | H | OCH₂CO₂CH₂CH₂CH₃ |
| 2-154 | 2-Cl | H | OCH₂CO₂CH₂CH₂CH₂CH₃ |
| 2-155 | 2-Cl | H | OCH₂CO₂CH(CH₃)₂ |
| 2-156 | 2-Cl | H | OCH₂CO₂C(CH₃)₃ |
| 2-157 | 2-Cl | H | OCH₂CO₂CH₂CH₂F |
| 2-158 | 2-Cl | H | OCH₂CO₂CH₂CH₂Cl |
| 2-159 | 2-Cl | H | OCH₂CO₂CH₂CCl₃ |
| 2-160 | 2-Cl | H | OCH₂CO₂CH₂CH=CH₂ |
| 2-161 | H | H | NHCH(CH₃)CO₂CH₃ |
| 2-162 | H | H | NHCH(CH₃)CO₂CH₂CH₃ |
| 2-163 | H | H | NHCH(CH₃)CO₂CH₂CH₂CH₃ |
| 2-164 | H | H | NHCH(CH₃)CO₂CH₂CH₂CH₂CH₃ |
| 2-165 | H | H | NHCH(CH₃)CO₂CH(CH₃)₂ |
| 2-166 | H | H | NHCH(CH₃)CO₂C(CH₃)₃ |
| 2-167 | H | H | NHCH(CH₃)CO₂CH₂CH₂F |
| 2-168 | H | H | NHCH(CH₃)CO₂CH₂CH₂Cl |
| 2-169 | H | H | NHCH(CH₃)CO₂CH₂CCl₃ |
| 2-170 | H | H | NHCH(CH₃)CO₂CH₂CH=CH₂ |
| 2-171 | H | H | NHCH₂CO₂CH₃ |
| 2-172 | H | H | NHCH₂CO₂CH₂CH₃ |
| 2-173 | H | H | NHCH₂CO₂CH₂CH₂CH₃ |
| 2-174 | H | H | NHCH₂CO₂CH₂CH₂CH₂CH₃ |
| 2-175 | H | H | NHCH₂CO₂CH(CH₃)₂ |
| 2-176 | H | H | NHCH₂CO₂C(CH₃)₃ |
| 2-177 | H | H | NHCH₂CO₂CH₂CH₂F |
| 2-178 | H | H | NHCH₂CO₂CH₂CH₂Cl |
| 2-179 | H | H | NHCH₂CO₂CH₂CCl₃ |
| 2-180 | H | H | NHCH₂CO₂CH₂CH=CH₂ |
| 2-181 | H | H | N(CH₃)CH(CH₃)CO₂CH₃ |
| 2-182 | H | H | N(CH₃)CH(CH₃)CO₂CH₂CH₃ |
| 2-183 | H | H | N(CH₃)CH₂CO₂CH₃ |
| 2-184 | H | H | N(CH₃)CH₂CO₂CH₂CH₃ |
| 2-185 | H | H | N(CH₃)CH₂CO₂CH₂CH₂CH₃ |
| 2-186 | H | H | OCH(CH₃)CO₂CH₂CH₂CH=CH₂ |
| 2-187 | H | H | OCH(CH₃)CO₂CH(CH₃)₂ |
| 2-188 | H | H | OCH(CH₃)CO₂CH(CH₃)CH₂CH₃ |
| 2-189 | H | H | OCH(CH₃)CO₂CH₂CH₂CH₂CH₂CH₃ |
| 2-190 | H | H | OCH(CH₃)CO₂CH₂CH₂CH(CH₃)₂ |
| 2-191 | H | H | OCH(CH₃)CO₂CH(CH₃)CH₂CH₃ |
| 2-192 | H | H | OCH(CH₃)CO₂CH(CH₃)CH₂CH₂CH₃ |
| 2-193 | H | H | OCH(CH₃)CO₂C(CH₃)₂CH₂CH₃ |
| 2-194 | H | H | OCH(CH₃)CO₂CH(CH₃)CH(CH₃)₂ |
| 2-195 | H | H | OCH(CH₃)CO₂CH₂C(CH₃)₃ |
| 2-196 | H | H | OCH(CH₃)CO₂CH₂C≡CH |
| 2-197 | H | H | OCH(CH₃)CO₂CH₂CH₂CH=CH₂ |
| 2-198 | H | H | OCH₂CO₂CH₂CH(CH₃)₂ |
| 2-199 | H | H | OCH₂CO₂CH(CH₃)CH₂CH₃ |
| 2-200 | H | H | OCH₂CO₂CH₂CH₂CH₂CH₂CH₃ |
| 2-201 | H | H | OCH₂CO₂CH₂C≡CH |

Compound of the general formula [I-3] (compound numbers are described in Table 3)

TABLE 3 [I-3]

| Compound No | $X^3$ | $X^4$ | A |
|---|---|---|---|
| 3-1 | H | H | $OCH(CH_3)CO_2CH_3$ |
| 3-2 | H | H | $OCH(CH_3)CO_2CH_2CH_3$ |
| 3-3 | H | H | $OCH(CH_3)CO_2CH_2CH_2CH_3$ |
| 3-4 | H | H | $OCH(CH_3)CO_2CH_2CH_2CH_2CH_3$ |
| 3-5 | H | H | $OCH(CH_3)CO_2CH(CH_3)_2$ |
| 3-6 | H | H | $OCH(CH_3)CO_2C(CH_3)_3$ |
| 3-7 | H | H | $OCH(CH_3)CO_2CH_2CH_2F$ |
| 3-8 | H | H | $OCH(CH_3)CO_2CH_2CH_2Cl$ |
| 3-9 | H | H | $OCH(CH_3)CO_2CH_2CCl_3$ |
| 3-10 | H | H | $OCH(CH_3)CO_2CH_2CH=CH_2$ |
| 3-11 | H | H | $OCH_2CO_2CH_3$ |
| 3-12 | H | H | $OCH_2CO_2CH_2CH_3$ |
| 3-13 | H | H | $OCH_2CO_2CH_2CH_2CH_3$ |
| 3-14 | H | H | $OCH_2CO_2CH_2CH_2CH_2CH_3$ |
| 3-15 | H | H | $OCH_2CO_2CH(CH_3)_2$ |
| 3-16 | H | H | $OCH_2CO_2C(CH_3)_3$ |
| 3-17 | H | H | $OCH_2CO_2CH_2CH_2F$ |
| 3-18 | H | H | $OCH_2CO_2CH_2CH_2Cl$ |
| 3-19 | H | H | $OCH_2CO_2CH_2CCl_3$ |
| 3-20 | H | H | $OCH_2CO_2CH_2CH=CH_2$ |
| 3-21 | H | H | $SCH(CH_3)CO_2CH_3$ |
| 3-22 | H | H | $SCH(CH_3)CO_2CH_2CH_3$ |
| 3-23 | H | H | $SCH(CH_3)CO_2CH_2CH_2CH_2CH_3$ |
| 3-24 | H | H | $SCH(CH_3)CO_2CH_2CH_2CH_3$ |
| 3-25 | H | H | $SCH(CH_3)CO_2CH(CH_3)_2$ |
| 3-26 | H | H | $SCH(CH_3)CO_2C(CH_3)_3$ |
| 3-27 | H | H | $SCH(CH_3)CO_2CH_2CH_2F$ |
| 3-28 | H | H | $SCH(CH_3)CO_2CH_2CH_2Cl$ |
| 3-29 | H | H | $SCH(CH_3)CO_2CH_2CCl_3$ |
| 3-30 | H | H | $SCH(CH_3)CO_2CH_2CH=CH_2$ |
| 3-31 | H | H | $SCH_2CO_2CH_3$ |
| 3-32 | H | H | $SCH_2CO_2CH_2CH_3$ |
| 3-33 | H | H | $SCH_2CO_2CH_2CH_2CH_3$ |
| 3-34 | H | H | $SCH_2CO_2CH_2CH_2CH_2CH_3$ |
| 3-35 | H | H | $SCH_2CO_2CH(CH_3)_2$ |
| 3-36 | H | H | $SCH_2CO_2C(CH_3)_3$ |
| 3-37 | H | H | $SCH_2CO_2CH_2CH_2F$ |
| 3-38 | H | H | $SCH_2CO_2CH_2CH_2Cl$ |
| 3-39 | H | H | $SCH_2CO_2CH_2CCl_3$ |
| 3-40 | H | H | $SCH_2CO_2CH_2CH=CH_2$ |
| 3-41 | 3-$CH_3$ | H | $OCH(CH_3)CO_2CH_3$ |
| 3-42 | 3-$CH_3$ | H | $OCH(CH_3)CO_2CH_2CH_3$ |
| 3-43 | 3-$CH_3$ | H | $OCH(CH_3)CO_2CH_2CH_2CH_3$ |
| 3-44 | 3-$CH_3$ | H | $OCH(CH_3)CO_2CH_2CH_2CH_2CH_3$ |
| 3-45 | 3-$CH_3$ | H | $OCH(CH_3)CO_2CH(CH_3)_2$ |
| 3-46 | 3-$CH_3$ | H | $OCH(CH_3)CO_2C(CH_3)_3$ |
| 3-47 | 3-$CH_3$ | H | $OCH(CH_3)CO_2CH_2CH_2F$ |
| 3-48 | 3-$CH_3$ | H | $OCH(CH_3)CO_2CH_2CH_2Cl$ |
| 3-49 | 3-$CH_3$ | H | $OCH(CH_3)CO_2CH_2CCl_3$ |
| 3-50 | 3-$CH_3$ | H | $OCH(CH_3)CO_2CH_2CH=CH_2$ |
| 3-51 | 3-$CH_3$ | H | $OCH_2CO_2CH_3$ |
| 3-52 | 3-$CH_3$ | H | $OCH_2CO_2CH_2CH_3$ |
| 3-53 | 3-$CH_3$ | H | $OCH_2CO_2CH_2CH_2CH_3$ |
| 3-54 | 3-$CH_3$ | H | $OCH_2CO_2CH_2CH_2CH_2CH_3$ |
| 3-55 | 3-$CH_3$ | H | $OCH_2CO_2CH(CH_3)_2$ |
| 3-56 | 3-$CH_3$ | H | $OCH_2CO_2C(CH_3)_3$ |
| 3-57 | 3-$CH_3$ | H | $OCH_2CO_2CH_2CH_2F$ |
| 3-58 | 3-$CH_3$ | H | $OCH_2CO_2CH_2CH_2Cl$ |
| 3-59 | 3-$CH_3$ | H | $OCH_2CO_2CH_2CCl_3$ |
| 3-60 | 3-$CH_3$ | H | $OCH_2CO_2CH_2CH=CH_2$ |
| 3-61 | 4-$CH_3$ | H | $OCH(CH_3)CO_2CH_2CH_2CH_2CH_3$ |
| 3-62 | 4-$CH_3$ | H | $OCH(CH_3)CO_2CH_3$ |
| 3-63 | 4-$CH_3$ | H | $OCH(CH_3)CO_2CH_2CH_3$ |
| 3-64 | 4-$CH_3$ | H | $OCH(CH_3)CO_2CH_2CH_2CH_3$ |
| 3-65 | 4-$CH_3$ | H | $OCH(CH_3)CO_2CH(CH_3)_2$ |
| 3-66 | 4-$CH_3$ | H | $OCH(CH_3)CO_2C(CH_3)_3$ |
| 3-67 | 4-$CH_3$ | H | $OCH(CH_3)CO_2CH_2CH_2F$ |
| 3-68 | 4-$CH_3$ | H | $OCH(CH_3)CO_2CH_2CH_2Cl$ |
| 3-69 | 4-$CH_3$ | H | $OCH(CH_3)CO_2CH_2CCl_3$ |
| 3-70 | 4-$CH_3$ | H | $OCH(CH_3)CO_2CH_2CH=CH_2$ |
| 3-71 | 4-$CH_3$ | H | $OCH_2CO_2CH_2CH_2CH_2CH_3$ |
| 3-72 | 4-$CH_3$ | H | $OCH_2CO_2CH_3$ |
| 3-73 | 4-$CH_3$ | H | $OCH_2CO_2CH_2CH_3$ |
| 3-74 | 4-$CH_3$ | H | $OCH_2CO_2CH_2CH_2CH_3$ |
| 3-75 | 4-$CH_3$ | H | $OCH_2CO_2CH(CH_3)_2$ |
| 3-76 | 4-$CH_3$ | H | $OCH_2CO_2C(CH_3)_3$ |
| 3-77 | 4-$CH_3$ | H | $OCH_2CO_2CH_2CH_2F$ |
| 3-78 | 4-$CH_3$ | H | $OCH_2CO_2CH_2CH_2Cl$ |
| 3-79 | 4-$CH_3$ | H | $OCH_2CO_2CH_2CCl_3$ |
| 3-80 | 4-$CH_3$ | H | $OCH_2CO_2CH_2CH=CH_2$ |
| 3-81 | 3-$OCH_3$ | H | $OCH(CH_3)CO_2CH_3$ |
| 3-82 | 3-$OCH_3$ | H | $OCH(CH_3)CO_2CH_2CH_3$ |
| 3-83 | 3-$OCH_3$ | H | $OCH(CH_3)CO_2CH_2CH_2CH_3$ |
| 3-84 | 3-$OCH_3$ | H | $OCH(CH_3)CO_2CH_2CH_2CH_2CH_3$ |
| 3-85 | 3-$OCH_3$ | H | $OCH(CH_3)CO_2CH(CH_3)_2$ |
| 3-86 | 3-$OCH_3$ | H | $OCH(CH_3)CO_2C(CH_3)_3$ |
| 3-87 | 3-$OCH_3$ | H | $OCH(CH_3)CO_2CH_2CH_2F$ |
| 3-88 | 3-$OCH_3$ | H | $OCH(CH_3)CO_2CH_2CH_2Cl$ |
| 3-89 | 3-$OCH_3$ | H | $OCH(CH_3)CO_2CH_2CCl_3$ |
| 3-90 | 3-$OCH_3$ | H | $OCH(CH_3)CO_2CH_2CH=CH_2$ |
| 3-91 | 3-$OCH_3$ | H | $OCH_2CO_2CH_3$ |
| 3-92 | 3-$OCH_3$ | H | $OCH_2CO_2CH_2CH_3$ |
| 3-93 | 3-$OCH_3$ | H | $OCH_2CO_2CH_2CH_2CH_3$ |
| 3-94 | 3-$OCH_3$ | H | $OCH_2CO_2CH_2CH_2CH_2CH_3$ |
| 3-95 | 3-$OCH_3$ | H | $OCH_2CO_2CH(CH_3)_2$ |
| 3-96 | 3-$OCH_3$ | H | $OCH_2CO_2C(CH_3)_3$ |
| 3-97 | 3-$OCH_3$ | H | $OCH_2CO_2CH_2CH_2F$ |
| 3-98 | 3-$OCH_3$ | H | $OCH_2CO_2CH_2CH_2Cl$ |
| 3-99 | 3-$OCH_3$ | H | $OCH_2CO_2CH_2CCl_3$ |
| 3-100 | 3-$OCH_3$ | H | $OCH_2CO_2CH_2CH=CH_2$ |
| 3-101 | 4-$OCH_3$ | H | $OCH(CH_3)CO_2CH_3$ |
| 3-102 | 4-$OCH_3$ | H | $OCH(CH_3)CO_2CH_2CH_3$ |
| 3-103 | 4-$OCH_3$ | H | $OCH(CH_3)CO_2CH_2CH_2CH_3$ |
| 3-104 | 4-$OCH_3$ | H | $OCH(CH_3)CO_2CH_2CH_2CH_2CH_3$ |
| 3-105 | 4-$OCH_3$ | H | $OCH(CH_3)CO_2CH(CH_3)_2$ |
| 3-106 | 4-$OCH_3$ | H | $OCH(CH_3)CO_2C(CH_3)_3$ |
| 3-107 | 4-$OCH_3$ | H | $OCH(CH_3)CO_2CH_2CH_2F$ |
| 3-108 | 4-$OCH_3$ | H | $OCH(CH_3)CO_2CH_2CH_2Cl$ |
| 3-109 | 4-$OCH_3$ | H | $OCH(CH_3)CO_2CH_2CCl_3$ |
| 3-110 | 4-$OCH_3$ | H | $OCH(CH_3)CO_2CH_2CH=CH_2$ |
| 3-111 | 4-$OCH_3$ | H | $OCH_2CO_2CH_3$ |
| 3-112 | 4-$OCH_3$ | H | $OCH_2CO_2CH_2CH_3$ |
| 3-113 | 4-$OCH_3$ | H | $OCH_2CO_2CH_2CH_2CH_3$ |
| 3-114 | 4-$OCH_3$ | H | $OCH_2CO_2CH_2CH_2CH_2CH_3$ |
| 3-115 | 4-$OCH_3$ | H | $OCH_2CO_2CH(CH_3)_2$ |
| 3-116 | 4-$OCH_3$ | H | $OCH_2CO_2C(CH_3)_3$ |
| 3-117 | 4-$OCH_3$ | H | $OCH_2CO_2CH_2CH_2F$ |
| 3-118 | 4-$OCH_3$ | H | $OCH_2CO_2CH_2CH_2Cl$ |
| 3-119 | 4-$OCH_3$ | H | $OCH_2CO_2CH_2CCl_3$ |
| 3-120 | 4-$OCH_3$ | H | $OCH_2CO_2CH_2CH=CH_2$ |
| 3-121 | 3-Cl | H | $OCH(CH_3)CO_2CH_3$ |
| 3-122 | 3-Cl | H | $OCH(CH_3)CO_2CH_2CH_3$ |

TABLE 3-continued

[I-3]

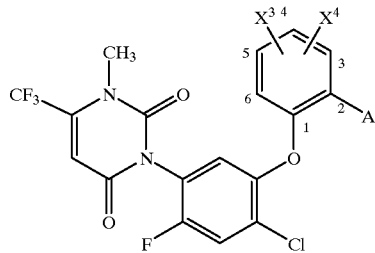

| Compound No | X³ | X⁴ | A |
|---|---|---|---|
| 3-123 | 3-Cl | H | OCH(CH₃)CO₂CH₂CH₂CH₃ |
| 3-124 | 3-Cl | H | OCH(CH₃)CO₂CH₂CH₂CH₂CH₃ |
| 3-125 | 3-Cl | H | OCH(CH₃)CO₂CH(CH₃)₂ |
| 3-126 | 3-Cl | H | OCH(CH₃)CO₂C(CH₃)₃ |
| 3-127 | 3-Cl | H | OCH(CH₃)CO₂CH₂CH₂F |
| 3-128 | 3-Cl | H | OCH(CH₃)CO₂CH₂CH₂Cl |
| 3-129 | 3-Cl | H | OCH(CH₃)CO₂CH₂CCl₃ |
| 3-130 | 3-Cl | H | OCH(CH₃)CO₂CH₂CH=CH₂ |
| 3-131 | 3-Cl | H | OCH₂CO₂CH₃ |
| 3-132 | 3-Cl | H | OCH₂CO₂CH₂CH₃ |
| 3-133 | 3-Cl | H | OCH₂CO₂CH₂CH₂CH₃ |
| 3-134 | 3-Cl | H | OCH₂CO₂CH₂CH₂CH₂CH₃ |
| 3-135 | 3-Cl | H | OCH₂CO₂CH(CH₃)₂ |
| 3-136 | 3-Cl | H | OCH₂CO₂C(CH₃)₃ |
| 3-137 | 3-Cl | H | OCH₂CO₂CH₂CH₂F |
| 3-138 | 3-Cl | H | OCH₂CO₂CH₂CH₂Cl |
| 3-139 | 3-Cl | H | OCH₂CO₂CH₂CCl₃ |
| 3-140 | 3-Cl | H | OCH₂CO₂CH₂CH=CH₂ |
| 3-141 | 4-Cl | H | OCH(CH₃)CO₂CH₃ |
| 3-142 | 4-Cl | H | OCH(CH₃)CO₂CH₂CH₃ |
| 3-143 | 4-Cl | H | OCH(CH₃)CO₂CH₂CH₂CH₃ |
| 3-144 | 4-Cl | H | OCH(CH₃)CO₂CH₂CH₂CH₂CH₃ |
| 3-145 | 4-Cl | H | OCH(CH₃)CO₂CH(CH₃)₂ |
| 3-146 | 4-Cl | H | OCH(CH₃)CO₂C(CH₃)₃ |
| 3-147 | 4-Cl | H | OCH(CH₃)CO₂CH₂CH₂F |
| 3-148 | 4-Cl | H | OCH(CH₃)CO₂CH₂CH₂Cl |
| 3-149 | 4-Cl | H | OCH(CH₃)CO₂CH₂CCl₃ |
| 3-150 | 4-Cl | H | OCH(CH₃)CO₂CH₂CH=CH₂ |
| 3-151 | 4-Cl | H | OCH₂CO₂CH₃ |
| 3-152 | 4-Cl | H | OCH₂CO₂CH₂CH₃ |
| 3-153 | 4-Cl | H | OCH₂CO₂CH₂CH₂CH₃ |
| 3-154 | 4-Cl | H | OCH₂CO₂CH₂CH₂CH₂CH₃ |
| 3-155 | 4-Cl | H | OCH₂CO₂CH(CH₃)₂ |
| 3-156 | 4-Cl | H | OCH₂CO₂C(CH₃)₃ |
| 3-157 | 4-Cl | H | OCH₂CO₂CH₂CH₂F |
| 3-158 | 4-Cl | H | OCH₂CO₂CH₂CH₂Cl |
| 3-159 | 4-Cl | H | OCH₂CO₂CH₂CCl₃ |
| 3-160 | 4-Cl | H | OCH₂CO₂CH₂CH=CH₂ |
| 3-161 | H | H | NHCH(CH₃)CO₂CH₃ |
| 3-162 | H | H | NHCH(CH₃)CO₂CH₂CH₃ |
| 3-163 | H | H | NHCH(CH₃)CO₂CH₂CH₂CH₃ |
| 3-164 | H | H | NHCH(CH₃)CO₂CH₂CH₂CH₂CH₃ |
| 3-165 | H | H | NHCH(CH₃)CO₂CH(CH₃)₂ |
| 3-166 | H | H | NHCH(CH₃)CO₂C(CH₃)₃ |
| 3-167 | H | H | NHCH(CH₃)CO₂CH₂CH₂F |
| 3-168 | H | H | NHCH(CH₃)CO₂CH₂CH₂Cl |
| 3-169 | H | H | NHCH(CH₃)CO₂CH₂CCl₃ |
| 3-170 | H | H | NHCH(CH₃)CO₂CH₂CH=CH₂ |
| 3-171 | H | H | NHCH₂CO₂CH₃ |
| 3-172 | H | H | NHCH₂CO₂CH₂CH₃ |
| 3-173 | H | H | NHCH₂CO₂CH₂CH₂CH₃ |
| 3-174 | H | H | NHCH₂CO₂CH₂CH₂CH₂CH₃ |
| 3-175 | H | H | NHCH₂CO₂CH(CH₃)₂ |
| 3-176 | H | H | NHCH₂CO₂C(CH₃)₃ |
| 3-177 | H | H | NHCH₂CO₂CH₂CH₂F |
| 3-178 | H | H | NHCH₂CO₂CH₂CH₂Cl |
| 3-179 | H | H | NHCH₂CO₂CH₂CCl₃ |
| 3-180 | H | H | NHCH₂CO₂CH₂CH=CH₂ |
| 3-181 | H | H | N(CH₃)CH(CH₃)CO₂CH₃ |
| 3-182 | H | H | N(CH₃)CH(CH₃)CO₂CH₂CH₃ |
| 3-183 | H | H | N(CH₃)CH₂CO₂CH₃ |
| 3-184 | H | H | N(CH₃)CH₂CO₂CH₂CH₃ |

TABLE 3-continued

[I-3]

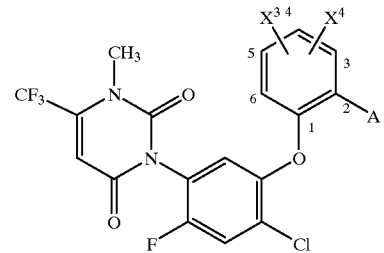

| Compound No | X³ | X⁴ | A |
|---|---|---|---|
| 3-185 | H | H | N(CH₃)CH₂CO₂CH₂CH₂CH₃ |
| 3-186 | H | H | OCH(CH₃)CO₂CH₂CH₂CH=CH₂ |
| 3-187 | H | H | OCH(CH₃)CO₂CH₂CH(CH₃)₂ |
| 3-188 | H | H | OCH(CH₃)CO₂CH(CH₃)CH₂CH₃ |
| 3-189 | H | H | OCH(CH₃)CO₂CH₂CH₂CH₂CH₂CH₃ |
| 3-190 | H | H | OCH(CH₃)CO₂CH₂CH₂CH(CH₃)₂ |
| 3-191 | H | H | OCH(CH₃)CO₂CH₂CH(CH₃)CH₂CH₃ |
| 3-192 | H | H | OCH(CH₃)CO₂CH(CH₃)CH₂CH₂CH₃ |
| 3-193 | H | H | OCH(CH₃)CO₂C(CH₃)₂CH₂CH₃ |
| 3-194 | H | H | OCH(CH₃)CO₂CH(CH₃)CH(CH₃)₂ |
| 3-195 | H | H | OCH(CH₃)CO₂CH₂C(CH₃)₃ |
| 3-196 | H | H | OCH(CH₃)CO₂CH₂C≡CH |
| 3-197 | H | H | OCH(CH₃)CO₂CH₂CH=CH₂ |
| 3-198 | H | H | OCH₂CO₂CH₂CH(CH₃)₂ |
| 3-199 | H | H | OCH₂CO₂CH(CH₃)CH₂CH₃ |
| 3-200 | H | H | OCH₂CO₂CH₂CH₂CH₂CH₂CH₃ |
| 3-201 | H | H | OCH₂CO₂CH₂C≡CH |

Compound of the formula [I-4] (compound numbers are described in Table 4)

TABLE 4

[I-4]

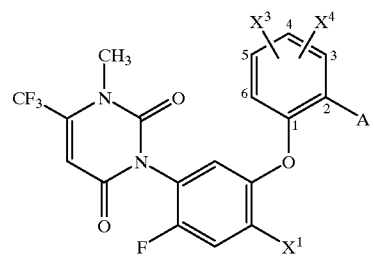

| Compound No | X¹ | X³ | X⁴ | A |
|---|---|---|---|---|
| 4-1 | NO₂ | H | H | OCH(CH₃)CO₂H |
| 4-2 | F | H | H | OCH(CH₃)CO₂H |
| 4-3 | Br | H | H | OCH(CH₃)CO₂H |
| 4-4 | CN | H | H | OCH(CH₃)CO₂H |
| 4-5 | NO₂ | H | H | OCH(CH₃)CO₂CH₃ |
| 4-6 | Br | H | H | OCH(CH₃)CO₂CH₃ |
| 4-7 | CN | H | H | OCH(CH₃)CO₂CH₃ |
| 4-8 | NO₂ | H | H | OCH(CH₃)CO₂CH₂CH₃ |
| 4-9 | F | 4-CH₃ | H | OCH(CH₃)CO₂CH₂CH₃ |
| 4-10 | CN | H | H | OCH(CH₃)CO₂CH₂CH₃ |
| 4-11 | Br | H | H | OCH(CH₃)CO₂CH₂CH₂CH₃ |
| 4-12 | CN | 4-CH₃ | H | OCH(CH₃)CO₂CH₂CH₂CH₃ |
| 4-13 | NO₂ | 5-CH₃ | H | OCH(CH₃)CO₂CH₂CH₂CH₂CH₃ |
| 4-14 | CN | H | H | OCH(CH₃)CO₂CH₂CH₂CH₂CH₃ |
| 4-15 | NO₂ | H | H | OCH₂CO₂H |
| 4-16 | F | H | H | OCH₂CO₂H |
| 4-17 | Br | H | H | OCH₂CO₂H |
| 4-18 | CN | H | H | OCH₂CO₂H |
| 4-19 | NO₂ | H | H | OCH₂CO₂CH₃ |
| 4-20 | F | H | H | OCH₂CO₂CH₃ |
| 4-21 | Br | H | H | OCH₂CO₂CH₃ |

TABLE 4-continued

[I-4]

CF₃ structure with CH₃, N, O, F, X¹, and phenyl-O-A substituents (X³, X⁴ on phenyl)

| Compound No | X¹ | X³ | X⁴ | A |
|---|---|---|---|---|
| 4-22 | CN | H | H | OCH₂CO₂CH₃ |
| 4-23 | CN | 4-CH₃ | H | OCH₂CO₂CH₃ |
| 4-24 | NO₂ | 5-CH₃ | H | OCH₂CO₂CH₃ |
| 4-25 | NO₂ | H | H | OCH₂CO₂CH₂CH₃ |
| 4-26 | F | H | H | OCH₂CO₂CH₂CH₃ |
| 4-27 | Br | H | H | OCH₂CO₂CH₂CH₃ |
| 4-28 | CN | H | H | OCH₂CO₂CH₂CH₃ |
| 4-29 | NO₂ | 4-CH₃ | H | OCH₂CO₂CH₂CH₃ |
| 4-30 | CN | 4-CH₃ | H | OCH₂CO₂CH₂CH₃ |
| 4-31 | NO₂ | 5-CH₃ | H | OCH₂CO₂CH₂CH₃ |
| 4-32 | CN | 5-CH₃ | H | OCH(CH₃)CO₂CH₃ |
| 4-33 | NO₂ | H | H | OCH₂CO₂CH₂CH₂CH₃ |
| 4-34 | CN | H | H | OCH₂CO₂CH₂CH₂CH₃ |
| 4-35 | NO₂ | H | H | OCH₂CO₂CH₂CH₂CH₂CH₃ |
| 4-36 | CN | H | H | OCH₂CO₂CH₂CH₂CH₂CH₃ |

Compound of the formula [I-5] (compound numbers are described in Table 5)

TABLE 5

[I-5]

| Compound No | X¹ | X³ | X⁴ | A |
|---|---|---|---|---|
| 5-1 | NO₂ | H | H | OCH(CH₃)CO₂H |
| 5-2 | F | H | H | OCH(CH₃)CO₂H |
| 5-3 | Br | H | H | OCH(CH₃)CO₂H |
| 5-4 | CN | H | H | OCH(CH₃)CO₂H |
| 5-5 | NO₂ | H | H | OCH(CH₃)CO₂CH₃ |
| 5-6 | Br | H | H | OCH(CH₃)CO₂CH₃ |
| 5-7 | CN | H | H | OCH(CH₃)CO₂CH₃ |
| 5-8 | NO₂ | H | H | OCH(CH₃)CO₂CH₂CH₃ |
| 5-9 | F | 4-CH₃ | H | OCH(CH₃)CO₂CH₂CH₃ |
| 5-10 | CN | H | H | OCH(CH₃)CO₂CH₂CH₃ |
| 5-11 | Br | H | H | OCH(CH₃)CO₂CH₂CH₂CH₃ |
| 5-12 | CN | 4-CH₃ | H | OCH(CH₃)CO₂CH₂CH₂CH₃ |
| 5-13 | NO₂ | 5-CH₃ | H | OCH(CH₃)CO₂CH₂CH₂CH₂CH₃ |
| 5-14 | CN | H | H | OCH(CH₃)CO₂CH₂CH₂CH₂CH₃ |
| 5-15 | NO₂ | H | H | OCH₂CO₂H |
| 5-16 | F | H | H | OCH₂CO₂H |
| 5-17 | Br | H | H | OCH₂CO₂H |
| 5-18 | CN | H | H | OCH₂CO₂H |
| 5-19 | NO₂ | H | H | OCH₂CO₂CH₃ |
| 5-20 | F | H | H | OCH₂CO₂CH₃ |
| 5-21 | Br | H | H | OCH₂CO₂CH₃ |
| 5-22 | CN | H | H | OCH₂CO₂CH₃ |
| 5-23 | CN | 4-CH₃ | H | OCH₂CO₂CH₃ |

TABLE 5-continued

[I-5]

| Compound No | X¹ | X³ | X⁴ | A |
|---|---|---|---|---|
| 5-24 | NO₂ | 5-CH₃ | H | OCH₂CO₂CH₃ |
| 5-25 | NO₂ | H | H | OCH₂CO₂CH₂CH₃ |
| 5-26 | F | H | H | OCH₂CO₂CH₂CH₃ |
| 5-27 | Br | H | H | OCH₂CO₂CH₂CH₃ |
| 5-28 | CN | H | H | OCH₂CO₂CH₂CH₃ |
| 5-29 | NO₂ | 4-CH₃ | H | OCH₂CO₂CH₂CH₃ |
| 5-30 | CN | 4-CH₃ | H | OCH₂CO₂CH₂CH₃ |
| 5-31 | NO₂ | 5-CH₃ | H | OCH₂CO₂CH₂CH₃ |
| 5-32 | CN | 5-CH₃ | H | OCH(CH₃)CO₂CH₃ |
| 5-33 | NO₂ | H | H | OCH₂CO₂CH₂CH₂CH₃ |
| 5-34 | CN | H | H | OCH₂CO₂CH₂CH₂CH₃ |
| 5-35 | NO₂ | H | H | OCH₂CO₂CH₂CH₂CH₂CH₃ |
| 5-36 | CN | H | H | OCH₂CO₂CH₂CH₂CH₂CH₃ |

Next, some of the typical intermediates useful for producing the present compound are shown below. The intermediates are specified by combining the formula described below with sub-number which determines combination of substituents as shown in Table 6. (For example, intermediate A1-1 is a compound having a general formula [A1-] wherein the substituents X¹, X² and A are those described in sub-number 1 in Table 6.)

A compound of formula [A1-]

[A1-]

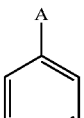

A compound of formula [A2-]

[A2-]

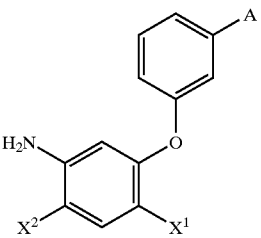

A compound of formula [A3-]

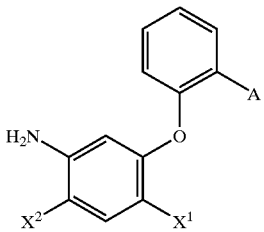
A compound of formula [A4-]
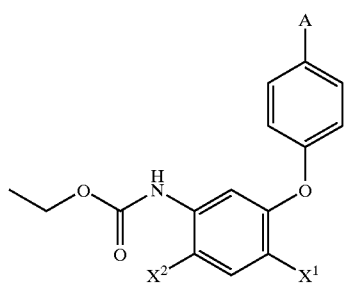
A compound of formula [A5-]
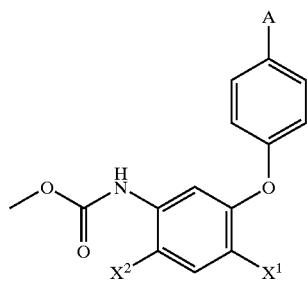
A compound of formula [A6-]
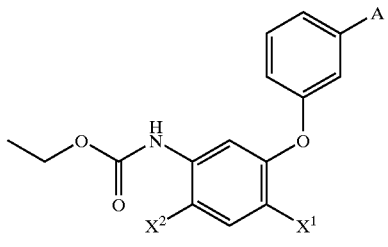
A compound of formula [A7-]
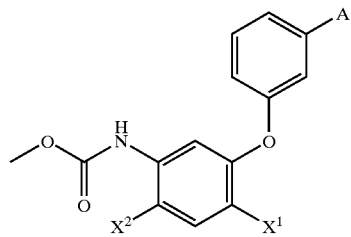
A compound of formula [A8-]
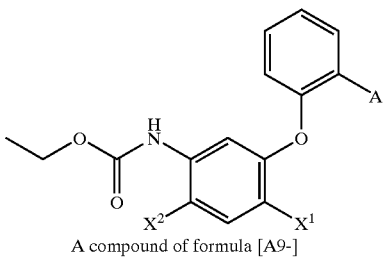
A compound of formula [A9-]
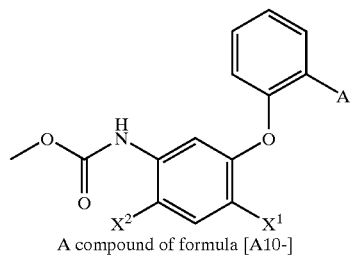
A compound of formula [A10-]
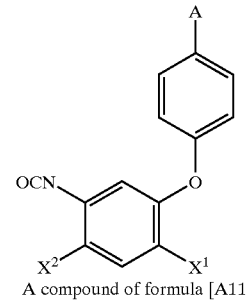
A compound of formula [A11-]
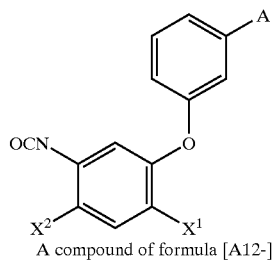
A compound of formula [A12-]
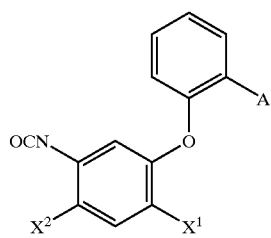
TABLE 6
| sub-number | $X^1$ | $X^2$ | A |
|---|---|---|---|
| 1 | Cl | F | $OCH_3$ |
| 2 | Cl | F | $OCH_2CH_3$ |
| 3 | Cl | F | $OCH(CH_3)_2$ |
| 4 | Cl | F | OH |

TABLE 6-continued

| | | | |
|---|---|---|---|
| 5 | Cl | F | OCH₂Ph |
| 6 | Cl | F | OCH(CH₃)CO₂H |
| 7 | Cl | F | OCH(CH₃)CO₂CH₃ |
| 8 | Cl | F | OCH(CH₃)CO₂CH₂CH₃ |
| 9 | Cl | F | OCH(CH₃)CO₂CH₂CH=CH₂ |
| 10 | Cl | F | OCH(CH₃)CO₂CH₂CH₂CH₂CH₃ |
| 11 | Cl | F | OCH(CH₃)CO₂CH(CH₃)₂ |
| 12 | Cl | F | OCH(CH₃)CO₂CH₂CH(CH₃)₂ |
| 13 | Cl | F | OCH(CH₃)CO₂CH(CH₃)CH₂CH₃ |
| 14 | Cl | F | OCH(CH₃)CO₂CH₂CH₂CH₂CH₂CH₃ |
| 15 | Cl | F | OCH(CH₃)CO₂CH₂CH₂CH(CH₃)₂ |
| 16 | Cl | F | OCH(CH₃)CO₂CH₂CH(CH₃)CH₂CH₃ |
| 17 | Cl | F | OCH(CH₃)CO₂CH(CH₃)CH₂CH₂CH₃ |
| 18 | Cl | F | OCH(CH₃)CO₂CH(CH₃)CH(CH₃)₂ |
| 19 | Cl | F | OCH(CH₃)CO₂CH₂C(CH₃)₃ |
| 20 | Cl | F | OCH(CH₃)CO₂CH₂C≡CH |
| 21 | Cl | F | OCH₂CO₂H |
| 22 | Cl | F | OCH₂CO₂CH₃ |
| 23 | Cl | F | OCH₂CO₂CH₂CH₃ |
| 24 | Cl | F | OCH₂CO₂CH₂CH=CH₂ |
| 25 | Cl | F | OCH₂CO₂CH₂CH₂CH₂CH₃ |
| 26 | Cl | F | OCH(CH₃)CO₂CH(CH₃)₂ |
| 27 | Cl | F | OCH(CH₃)CO₂CH₂CH(CH₃)₂ |
| 28 | Cl | F | OCH(CH₃)CO₂CH(CH₃)CH₂CH₃ |
| 29 | Cl | F | OCH(CH₃)CO₂CH₂CH₂CH₂CH₂CH₃ |
| 30 | Cl | F | OCH(CH₃)CO₂CH₂CH₂CH(CH₃)₂ |
| 31 | Cl | F | OCH(CH₃)CO₂CH₂CH(CH₃)CH₂CH₃ |
| 32 | Cl | F | OCH(CH₃)CO₂CH(CH₃)CH₂CH₂CH₃ |
| 33 | Cl | F | OCH(CH₃)CO₂CH(CH₃)CH(CH₃)₂ |
| 34 | Cl | F | OCH(CH₃)CO₂CH₂C(CH₃)₃ |
| 35 | Cl | F | OCH(CH₃)CO₂CH₂C≡CH |
| 36 | Br | F | OCH₃ |
| 37 | Br | F | OCH₂CH₃ |
| 38 | Br | F | OCH(CH₃)₂ |
| 39 | Br | F | OH |
| 40 | Br | F | OCH₂Ph |
| 41 | Br | F | OCH(CH₃)CO₂H |
| 42 | Br | F | OCH(CH₃)CO₂CH₃ |
| 43 | Br | F | OCH(CH₃)CO₂CH₂CH₃ |
| 44 | Br | F | OCH(CH₃)CO₂CH₂CH=CH₂ |
| 45 | Br | F | OCH(CH₃)CO₂CH₂CH₂CH₂CH₃ |
| 46 | Br | F | OCH(CH₃)CO₂CH(CH₃)₂ |
| 47 | Br | F | OCH(CH₃)CO₂CH₂CH(CH₃)₂ |
| 48 | Br | F | OCH(CH₃)CO₂CH(CH₃)CH₂CH₃ |
| 49 | Br | F | OCH(CH₃)CO₂CH₂CH₂CH₂CH₂CH₃ |
| 50 | Br | F | OCH(CH₃)CO₂CH₂CH₂CH(CH₃)₂ |
| 51 | Br | F | OCH(CH₃)CO₂CH₂CH(CH₃)CH₂CH₃ |
| 52 | Br | F | OCH(CH₃)CO₂CH(CH₃)CH₂CH₂CH₃ |
| 53 | Br | F | OCH(CH₃)CO₂CH(CH₃)CH(CH₃)₂ |
| 54 | Br | F | OCH(CH₃)CO₂CH₂C(CH₃)₃ |
| 55 | Br | F | OCH(CH₃)CO₂CH₂C≡CH |
| 56 | Br | F | OCH₂CO₂H |
| 57 | Br | F | OCH₂CO₂CH₃ |
| 58 | Br | F | OCH₂CO₂CH₂CH₃ |
| 59 | Br | F | OCH₂CO₂CH₂CH=CH₂ |
| 60 | Br | F | OCH₂CO₂CH₂CH₂CH₂CH₃ |
| 61 | Br | F | OCH(CH₃)CO₂CH(CH₃)₂ |
| 62 | Br | F | OCH(CH₃)CO₂CH₂CH(CH₃)₂ |
| 63 | Br | F | OCH(CH₃)CO₂CH(CH₃)CH₂CH₃ |
| 64 | Br | F | OCH(CH₃)CO₂CH₂CH₂CH₂CH₂CH₃ |
| 65 | Br | F | OCH(CH₃)CO₂CH₂CH₂CH(CH₃)₂ |
| 66 | Br | F | OCH(CH₃)CO₂CH₂CH(CH₃)CH₂CH₃ |
| 67 | Br | F | OCH(CH₃)CO₂CH(CH₃)CH₂CH₂CH₃ |
| 68 | Br | F | OCH(CH₃)CO₂CH(CH₃)CH(CH₃)₂ |
| 69 | Br | F | OCH(CH₃)CO₂CH₂C(CH₃)₃ |
| 70 | Br | F | OCH(CH₃)CO₂CH₂C≡CH |
| 71 | NO₂ | F | OCH₃ |
| 72 | NO₂ | F | OCH₂CH₃ |
| 73 | NO₂ | F | OCH(CH₃)₂ |
| 74 | NO₂ | F | OH |
| 75 | NO₂ | F | OCH₂Ph |
| 76 | NO₂ | F | OCH(CH₃)CO₂H |
| 77 | NO₂ | F | OCH(CH₃)CO₂CH₃ |
| 78 | NO₂ | F | OCH(CH₃)CO₂CH₂CH₃ |
| 79 | NO₂ | F | OCH(CH₃)CO₂CH₂CH=CH₂ |
| 80 | NO₂ | F | OCH₂CO₂H |
| 81 | NO₂ | F | OCH₂CO₂CH₃ |
| 82 | NO₂ | F | OCH₂CO₂CH₂CH₃ |
| 83 | NO₂ | F | OCH₂CO₂CH₂CH=CH₂ |
| 84 | CN | F | OCH₃ |
| 85 | CN | F | OCH₂CH₃ |
| 86 | CN | F | OCH(CH₃)₂ |
| 87 | CN | F | OH |
| 88 | CN | F | OCH₂Ph |
| 89 | CN | F | OCH(CH₃)CO₂H |
| 90 | CN | F | OCH(CH₃)CO₂CH₃ |
| 91 | CN | F | OCH(CH₃)CO₂CH₂CH₃ |
| 92 | CN | F | OCH(CH₃)CO₂CH₂CH=CH₂ |
| 93 | CN | F | OCH₂CO₂H |
| 94 | CN | F | OCH₂CO₂CH₃ |
| 95 | CN | F | OCH₂CO₂CH₂CH₃ |
| 96 | CN | F | OCH₂CO₂CH₂CH=CH₂ |

Next, the formulation examples of the present compounds are explained. In the examples, the present compounds are shown as Compound No. in Tables 1 to 5, and "part(s)" shows "part(s) by weight".

FORMULATION EXAMPLE 1

Fifty (50) parts of each of the present compounds 1-1 to 1-201, 2-1 to 2-201, 3-1 to 3-201, 4-1 to 4-36 and 5-1 to 5-36, 3 parts of calcium ligninsulfonate, 2 parts of sodium laurylsulfate, and 45 parts of synthetic hydrated silicon dioxide are well pulverized and mixed, to obtain each of the wettable powders.

FORMULATION EXAMPLE 2

Ten (10) parts of each of the present compound 1-1 to 1-201, 2-1 to 2-201, 3-1 to 3-201, 4-1 to 4-36 and 5-1 to 5-36, 14 parts of polyoxyethylenestyryl phenyl ether, 6 parts of calcium dodecylbenzenesulfonate, 35 parts of xylene, and 35 parts of cyclohexanone are mixed to obtain each of the emulsifiable concentrates.

FORMULATION EXAMPLE 3

Two (2) parts of each of the present compound 1-1 to 1-201, 2-1 to 2-201, 3-1 to 3-201, 4-1 to 4-36 and 5-1 to 5-36, 2 parts of synthetic hydrated silica, 2 parts of calcium ligninsulfonate, 30 parts of bentonite, and 64 parts of kaolin clay are well pulverized and mixed, and after adding water and well kneading, that is granulated and dried to obtain each of the granules.

FORMULATION EXAMPLE 4

Twenty-five (25) parts of each of the present compound 1-1 to 1-201, 2-1 to 2-201, 3-1 to 3-201, 4-1 to 4-36 and 5-1 to 5-36, 50 parts of a 10% aqueous solution of polyvinyl alcohol, and 25 parts of water are mixed, are wet pulverized until the average particle diameter is 5 μm or less, to obtain each of the flowables.

FORMULATION EXAMPLE 5

Five(5) parts of each of the present compound 1-1 to 1-201, 2-1 to 2-201, 3-1 to 3-201, 4-1 to 4-36 and 5-1 to 5-36 is added into 40 parts of 10% aqueous solution of polyvinyl alcohol, and the mixture is emulsified and dispersed until the average diameter is 10 μm or less by homogenizer. Next, 55 parts of water is added to the resultant mixture to obtain each of the concentrated emulsion.

Next, test examples are explained to show that the present compounds are effective as an active ingredient of a herbicide. In the examples, each of the present compounds are shown as Compound No. in Tables 1 to 5.

TEST EXAMPLE 1

A cylindrical plastic pot having a diameter of 10 cm and a depth of 10 cm was filled with soil and then seeded with Ivyleaf morningglory (*Ipomoea hederacea*), velvetleaf (*Abutilon theophrasti*), barnyardgrass (*Echinochloa crus-galli*) and blackgrass (*Alopecurus myosuroides*). These test plants were grown in a greenhouse for 9 days. Then, each of compounds 1-1, 2-1, 3-1, 3-2, 3-11 and 3-12 was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare After the application, the test plants were grown in the greenhouse for 7 days, and the herbicidal activity of the applied composition was determined. As a result, it was determined that the growth of Ivyleaf morningglory, velvetleaf, barnyardgrass and blackgrass was completely controlled when compounds 1-1, 2-1, 3-1, 3-2, 3-11 and 3-12 were applied at the dosage of 125 g/ha, respectively.

TEST EXAMPLE 2

A cylindrical plastic pot having a diameter of 10 cm and a depth of 10 cm was filled with soil and then seeded with Ivyleaf morningglory (*Ipomoea hederacea*), velvetleaf (*Abutilon theophrasti*) and barnyardgrass (*Echinochloa crus-galli*). Then, each of the compounds 1-1, 2-1 and 3-1 was formulated into an emulsifiable concentrate according to Formulation Example 2 and then diluted to the prescribed amount with water, and the dilution was uniformly sprayed over the surface of the soil with a sprayer at a rate of 1000 liters per hectare. After the application, the test plants were grown in the greenhouse for 7 days, and the herbicidal activity of the applied composition was examined. The emergence of ivyleaf morningglory, velvetleaf and barnyardgrass were completely controlled when compounds 1-1, 2-1 and 3-1 were applied at the dosage of 500 g/ha, respectively.

TEST EXAMPLE 3

A cylindrical plastic pot having a diameter of 10 cm and a depth of 10 cm was filled with soil and then seeded with Ivyleaf morningglory (*Ipomoea hederacea*), velvetleaf (*Abutilon theophrasti*) and barnyardgrass (*Echinochloa crus-galli*). These test plants were grown in a greenhouse for 9 days. After then, each of the compounds 3-16, 3-20 and 3-198 was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 7 days, and the herbicidal activity was examined. As a result, it was determined that the growth of Ivyleaf morningglory, velvetleaf and barnyardgrass was completely controlled when compounds 3-16, 3-20 and 3-198 were applied at the dosage of 500 g/ha, respectively.

TEST EXAMPLE 4

A cylindrical plastic pot having a diameter of 10 cm and a depth of 10 cm was filled with soil and then seeded with Ivyleaf morningglory (*Ipomoea hederacea*), velvetleaf (*Abutilon theophrasti*), barnyardgrass (*Echinochloa crus-galli*) and blackgrass (*Alopecurus myosuroides*). Then, each of the compounds 3-2, 3-11, 3-12, 3-16, 3-20 and 3-198 was formulated into an emulsifiable concentrate according to Formulation Example 2 and then diluted to the prescribed amount with water, and the dilution was uniformly sprayed over the surface of the soil with a sprayer at a rate of 1000 liters per hectare. After the application, the test plants were grown in the greenhouse for 7 days, and the herbicidal activity of the applied composition was examined. The emergence of Ivyleaf morningglory, velvetleaf, barnyardgrass and blackgrass were completely controlled when compounds 3-2, 3-11, 3-12, 3-16, 3-20 and 3-198 were applied at the dosage of 2000 g/ha, respectively.

In the following test examples, the herbicidal activity was evaluated at 11 levels with indices of 0 to 10, i.e., designated by the numeral "0", "1", "2", "2", "3", "4", "5", "6", "7", "8", "9" wherein "0" means that there was no or little difference in the degree of germination or growth between the treated and the untreated tested plants at the time of examination, and "10" means that the test plants died complete or their germination or growth was completely inhibited.

TABLE 7

| Compound No | Structure | Note |
|---|---|---|
| A | 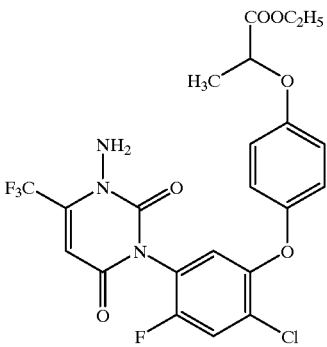 | WO 98/41093 |

TABLE 7-continued

| Compound No | Structure | Note |
|---|---|---|
| B | (structure shown) | WO 97/01541 |
| C | (structure shown) | WO 97/01541 |

TEST EXAMPLE 5

A cylindrical plastic pot having a diameter of 18.5 cm and a depth of 15 cm was filled with soil and then seeded with common chickweed (Stellaria media). These test plants were grown in a greenhouse for 29 days. After then, each of the compound 1-2 and Compound A was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 9 days, and the herbicidal activity was examined. The results are shown in the following Table 8.

TABLE 8

| Compound No | Dosage (g/ha) | Herbicidal activity |
|---|---|---|
| 1-2 | 10 | 10 |
| A | 10 | 5 |

TEST EXAMPLE 6

A plastic pot (27 cm×19 cm×7 cm) was filled with soil and then seeded with Johnsongrass (Sorghum halepense) Giant foxtail (Setaria faberi), barnyardgrass (Echinochloa Crusgalli), large crabgrass (Digitaria sanguinalis), Broadleaf signalgrass (Brachiaria platyphylla) and wild oat (Avena fatua). These test plants were grown in a greenhouse for 25 days. After then, each of the compounds 3-11, 4-22, B and C was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 4 days, and the herbicidal activity was examined. The results are shown in the following Table 9. (In the Table 9, the test plants are shown as follows. Johnsongrass: J, Giant foxtail: GF, Barnyardgrass: B Large crabgrass: LC, Broadleaf signalgrass: BC Wild oat: W

TABLE 9

| Compound No. | Doasage (g/ha) | Herbicidal activity | | | | | |
|---|---|---|---|---|---|---|---|
| | | J | GF | B | LC | BC | W |
| 3-11 | 3.3 | 10 | 9 | 10 | 10 | 10 | 10 |
| | 1 | 9 | 9 | 8 | 9 | 9 | 10 |
| | 0.33 | 8 | 8 | 7 | 8 | 8 | 8 |
| 4-22 | 3.3 | 9 | 10 | 9 | 9 | 9 | 10 |
| | 1 | 8 | 8 | 9 | 9 | 8 | 9 |
| | 0.33 | 8 | 7 | 8 | 9 | 8 | 8 |
| B | 3.3 | 7 | 7 | 7 | 8 | 8 | 7 |
| | 1 | 7 | 5 | 6 | 7 | 6 | 5 |
| | 0.33 | 2 | 3 | 2 | 3 | 2 | 2 |
| C | 3.3 | 6 | 4 | 6 | 5 | 6 | 5 |
| | 1 | 4 | 3 | 4 | 3 | 3 | 3 |
| | 0.33 | 2 | 1 | 1 | 2 | 2 | 1 |

What is claimed is:

1. An uracil compound of the formula [I]:

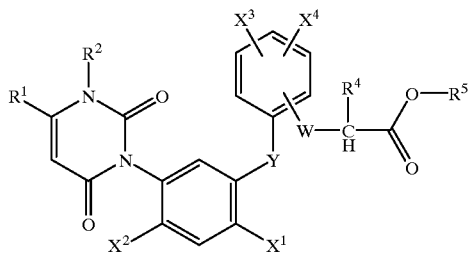

[I]

wherein W represents oxygen, sulfur, imino or $C_1$ to $C_3$ alkylimino; Y represents oxygen, sulfur, imino or $C_1$ to $C_3$ alkylimino; $R^1$ represents $C_1$ to $C_3$ alkyl or $C_1$ to $C_3$ haloalkyl; $R^2$ represents $C_1$ to $C_3$ alkyl; $R^4$ represents hydrogen or methyl; $R^5$ represents $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl or $C_3$ to $C_6$ haloalkynyl; $X^1$ represents halogen, cyano or nitro; $X^2$ represents hydrogen or halogen; and each of $X^3$ and $X^4$ independently represents hydrogen, halogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, $C_3$ to $C_6$ haloalkynyl, $C_1$ to $C_6$ alkoxy $C_1$ to $C_6$ alkyl, $C_1$ to $C_6$ alkoxy, $C_1$ to $C_6$ haloalkoxy, $C_1$ to $C_6$ alkoxycarbonyl $C_1$ to $C_6$ alkoxy or cyano.

2. The uracil compound according to claim 1, wherein $X^1$ is halogen and $X^2$ is halogen.

3. The uracil compound according to claim 1, wherein $X^1$ is chlorine.

4. The uracil compound according to claim 1, wherein $X^2$ is fluorine.

5. The uracil compound according to claim 1 or 2, wherein the substitution position of W is ortho-position of Y on the benzene ring.

6. The uracil compound according to claim 1 or 2, wherein W is oxygen.

7. The uracil compound according to claim 1 or 2, wherein $R^1$ is methyl or trifluoromethyl.

8. The uracil compound according to claim 1 or 2, wherein $R^2$ is methyl.

9. The uracil compound according to claim 1 or 2, wherein $X^3$ and $X^4$ are hydrogen.

10. The uracil compound according to claim 1 or 2, wherein $R^5$ is methyl or ethyl.

11. A herbicidal composition which comprises the uracil compound according to claim 1, and inert carrier or diluent.

12. A method for controlling weeds, which comprises applying an effective amount of the uracil compound according to claim 1 to weeds or a place where the weeds grow or will grow.

13. An uracil compound of the formula [VII]:

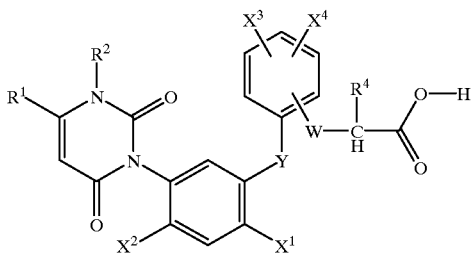

[VII]

wherein W represents oxygen, sulfur, imino or $C_1$ to $C_3$ alkylimino; Y represents oxygen, sulfur imino or $C_1$ to $C_3$ alkylimino; $R^1$ represents $C_1$ to $C_3$ alkyl or $C_1$ to $C_3$ haloalkyl; $R^2$ represents $C_1$ to $C_3$ alkyl; $R^4$ represents hydrogen or methyl; $X^1$ represents halogen, cyano or nitro; $X^2$ represents hydrogen or halogen, and each of $X^3$ and $X^4$ independently represents hydrogen, halogen, $C_1$ to $C_6$ alkyl, $C_1$ to $C_6$ haloalkyl, $C_3$ to $C_6$ haloalkenyl, $C_3$ to $C_6$ alkynyl, $C_3$ to $C_6$ haloalkynyl, $C_1$ to $C_6$ alkoxy $C_1$ to $C_6$ alkyl, $C_1$ to $C_6$ alkoxy, $C_1$ to $C_6$ haloalkoxy, $C_1$ to $C_6$ alkoxycarbonyl $C_1$ to $C_6$ alkoxy or cyano.

14. The uracil compound according to claim 13, wherein the substitution position of W is ortho-position of Y on the benzene ring.

15. The uracil compound according to claim 1, wherein $R^1$ is trifluoromthyl, $R^2$ is methyl, $R^4$ is hydrogen, $R^5$ is methyl, $X^1$ is chlorine, $X^2$ is fluorine, $X^3$ is hydrogen, $X^4$ is hydrogen, W is oxygen, Y is oxygen, and the substitution position of W on the benzene ring is ortho position of Y.

16. The uracil compound according to claim 1, wherein $R^1$ is trifluoomethyl, $R^2$ is methyl, $R^4$ is hydrogen, $R^5$ is ethyl, $X^1$ is chlorine, $X^2$ is fluorine, $X^3$ is hydrogen, $X^4$ is hydrogen, W is oxygen, Y is oxygen, and the substitution position of W on the benzene ring is ortho position of Y.

17. The uracil compound according to claim 3, wherein $X^2$ is fluorine.

18. The uracil compound according to claim 17, wherein $R^1$ is trifluoromethyl and $R^2$ is methyl.

19. The uracil compound according to claim 18, wherein W is oxygen and Y is oxygen or sulfur.

20. The uracil compound according to claim 18, wherein Y is oxygen.

21. The uracil compound according to any one of claims 3, 17, 18 or 19, wherein the substitution position of W is ortho-position of Y on the benzene ring.

22. The uracil compound according to claim 20, wherein the substitution position of W is ortho-position of Y on the benzene ring.

23. The uracil compound according to claim 13, wherein $R^1$ is trifluoromethyl, $R^2$ is methyl, $R^4$ is hydrogen or methyl, $X^1$ is chlorine, $X^2$ is fluorine, $X^3$ is hydrogen, $X^4$ is hydrogen, W is oxygen, Y is oxygen, and the substitution position of W on the benzene ring is ortho-position of Y.

24. A herbicidal composition which comprises the uracil compound according to any one of claims 15, 16, 17, or 22, and inert carrier or diluent.

25. A method for controlling weeds, which comprises applying an effective amount of the uracil compund according to any one of claims 15, 16, 17, or 22 to weeds or a place where the weeds grow or will grow.

26. The uracil compound according to claim 22, wherein $X^3$ is hydrogen and $X^4$ is hydrogen.

27. The uracil compound according to claim 26, wherein $R^4$ is hydrogen.

28. The uracil compound according to claim 1, wherein $X^1$ is nitro.

29. A process for producing an uracil compound of the formula [I]:

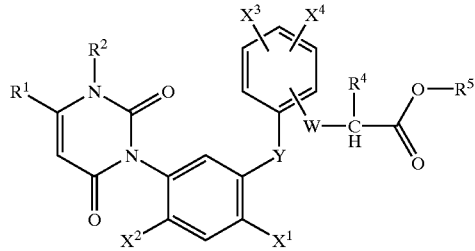

[I]

wherein W represents oxygen, sulfur, imino or $C_1$ to $C_3$ alkylimino; Y represents oxygen, sulfur, imino or $C_1$ to $C_3$ alkylimino; $R^1$ represents $C_1$ to $C_3$ alkyl or $C_1$ to $C_3$ haloalkyl; $R^2$ represents $C_1$ to $C_3$ alkyl; $R^4$ represents hydrogen or methyl; $R^5$ represents $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl or $C_3$ to $C_6$ haloalkynyl; $X^1$ represents halogen, cyano or nitro; $X^2$ represents hydrogen or halogen; and each of $X^3$ and $X^4$ independently represents hydrogen, halogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, $C_3$ to $C_6$ haloalkynyl, $C_1$ to $C_6$ alkoxy $C_1$ to $C_6$ alkyl, $C_1$ to $C_6$ alkoxy, $C_1$ to $C_6$ haloalkoxy, $C_1$ to $C_6$ alkoxycarbonyl $C_1$ to $C_6$ alkoxy or cyano, which comprises reacting a compound of formula [III]:

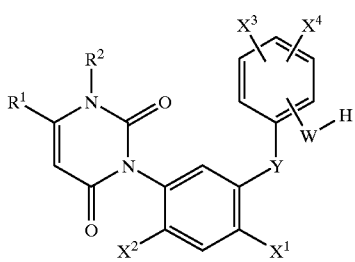

[III]

wherein $R^1$, $R^2$, W, Y, $X^1$, $X^2$, $X^3$ and $X^4$ are the same as defined for formula [I], with a compound of formula [IV]:

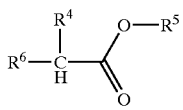

[IV]

wherein $R^4$ and $R^5$ are the same as defined for formula [I], and $R^6$ represents chlorine, bromine, iodine, methanesulfonyloxy and p-toluenesulfonyoxy in the presence of a base.

30. A process for producing an uracil compound of the formula [I]:

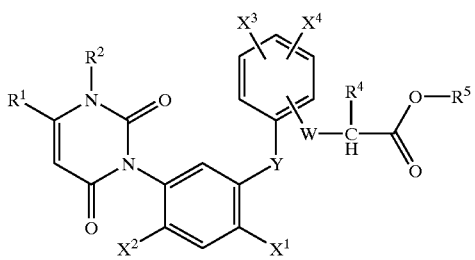

[I]

wherein W represents oxygen, sulfur, imino or $C_1$ to $C_3$ alkylimino; Y represents oxygen, sulfur, imino or $C_1$ to $C_3$ alkylimino; $R^1$ represents $C_1$ to $C_3$ alkyl or $C_1$ to $C_3$ haloalkyl; $R^2$ represents $C_1$ to $C_3$ alkyl; $R^4$ represents hydrogen or methyl; $R^5$ represents $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl or $C_3$ to $C_6$ haloalkynyl; $X^1$ represents halogen, cyano, nitro; $X^2$ represents hydrogen or halogen; and each of $X^3$ and $X^4$ independently represents hydrogen, halogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, $C_3$ to $C_6$ haloalkynyl, $C_1$ to $C_6$ alkoxy $C_1$ to $C_6$ alkyl, $C_1$ to $C_6$ alkoxy, $C_1$ to $C_6$ haloalkoxy, $C_1$ to $C_6$ alkoxycarbonyl $C_1$ to $C_6$ alkoxy or cyano, which comprises reacting a compound of formula [VII]:

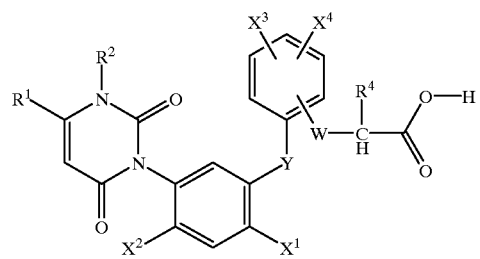

[VII]

wherein $R^1$, $R^2$, W, Y, $X^1$, $X^2$, $X^3$ and $X^4$ are the same as defined for formula [I], with a chlorinating agent to give an acid chloride, and then, reacting the acid chloride with a compound of formula [VIII]:

$$HO-R^5 \quad [VIII]$$

wherein $R^5$ are the same as defined for formula [I] in the presence of a base.

31. A process for producing an uracil compound of the formula [I]:

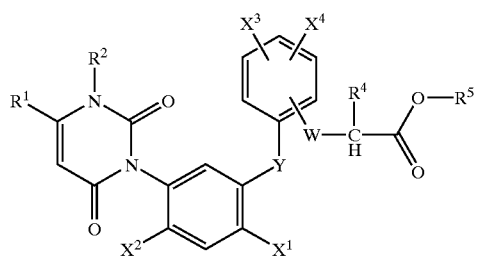

[I]

wherein W represents oxygen, sulfur, imino or $C_1$ to $C_3$ alkylimino; Y represents oxygen, sulfur, imino or $C_1$ to $C_3$ alkylimino; $R^1$ represents $C_1$ to $C_3$ alkyl or $C_1$ to $C_3$ haloalkyl; $R^2$ represents $C_1$ to $C_3$ alkyl; $R^4$ represents hydrogen or methyl; $R^5$ represents $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl or $C_3$ to $C_6$ haloalkynyl; $X^1$ represents halogen, cyano, or nitro; $X^2$ represents hydrogen or halogen; and each of $X^3$ and $X^4$ independently represents hydrogen, halogen, $C_1$ to $C_6$ alkyl, $C_1$ to $C_6$ haloalkyl, $C_3$ to $C_6$ alkenyl, $C_3$ to $C_6$ haloalkenyl, $C_3$ to $C_6$ alkynyl, $C_3$ to $C_6$ haloalkynyl, $C_1$ to $C_6$ alkoxy $C_1$ to $C_6$ alkyl, $C_1$ to $C_6$ alkoxy, $C_1$ to $C_6$ haloalkoxy, $C_1$ to $C_6$ alkoxycarbonyl $C_1$ to $C_6$ alkoxy or cyano, which comprises reacting a compound of formula [XXXI]:

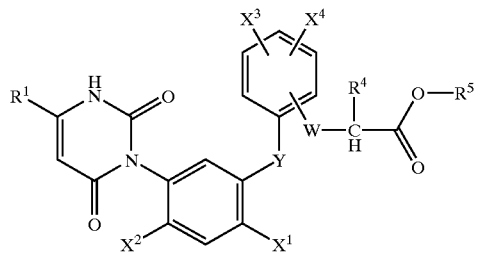

[XXXI]

wherein $R^1$, $R^4$, $R^5$, W, Y, $X^1$, $X^2$, $X^3$ and $X^4$ are the same as defined for formula [I], with a compound of formula [XXXX]:

$$R^{18}-R^2 \quad [XXXX]$$

wherein $R^2$ are the same as defined for formula [I], and $R^{18}$ represents chlorine, bromine, iodine, methanesulfonyloxy and p-toluenesulfonyoxy, in the presence of a base.

32. A herbicidal composition which comprises the uracil compound according to claim 15, and inert carrier or diluent.

33. A herbicidal composition which comprises the uracil compound according to claim 16, and inert carrier or diluent.

34. A herbicidal composition which comprises the uracil compound according to claim 22, and inert carrier or diluent.

35. A herbicidal composition which comprises the uracil compound according to claim 26, and inert carrier or diluent.

36. A herbicidal composition which comprises the uracil compound according to claim 27, and inert carrier or diluent.

37. The method according to claim 12, wherein the weeds are curly dock (*Rumex crispus*), broadleaf dock (*Rumex obtusifolius*), shepherdpurse (*Capsella bursa-pastoris*), common vetch (*Vicia sativa*), sun spurge (*Euphorbia helioscopia*), spotted spurge (*Euphorbia maculata*), Carolina geranium (*Geranium carolinianum*), common dayflower (*Commelina communis*), or field horsetail (*Equisetum arvense*).

38. A method for controlling weeds, which comprises applying an effective amount of the uracil compound according to claim 15 to weeds or a place where the weeds grow or will grow.

39. A method for controlling weeds, which comprises applying an effective amount of the uracil compound according to claim 16 to weeds or a place where the weeds grow or will grow.

40. A method for controlling weeds, which comprises applying an effective amount of the uracil compound according to claim 22 to weeds or a place where the weeds grow or will grow.

41. A method for controlling weeds, which comprises applying an effective amount of the uracil compound according to claim 26 to weeds or a place where the weeds grow or will grow.

42. A method for controlling weeds, which comprises applying an effective amount of the uracil compound according to claim 27 to weeds or a place where the weeds grow or will grow.

43. The method according to claim 12, wherein the weeds are weeds present in the no-tillage cultivation of soybean, corn, wheat.

44. The method according to claim 38, wherein the weeds are weeds present in the no-tillage cultivation of soybean, corn, wheat.

45. The method according to claim 39, wherein the weeds are weeds present in the no-tillage cultivation of soybean, corn, wheat.

46. The method according to claim 40, wherein the weeds are weeds present in the no-tillage cultivation of soybean, corn, wheat.

47. The method according to claim 41, wherein the weeds are weeds present in the no-tillage cultivation of soybean, corn, wheat.

48. The method according to claim 42, wherein the weeds are weeds present in the no-tillage cultivation of soybean, corn, wheat.

* * * * *

UNITED STATES PATENT AND TRADEMARK OFFICE
CERTIFICATE OF CORRECTION

PATENT NO.   : 6,451,740 B2
DATED        : September 17, 2002
INVENTOR(S)  : Yoshitomo Tohyama, Yuzuru Sanemitsu, and Tomohiko Gotou It is certified that error appears in the above-identified patent and that said Letters Patent is hereby corrected as shown below:

Column 103,
Line 57, change "trifluoromthyl" to -- trifluoromethyl --.
Line 62, change "trifluoomethyl" to -- trifluoromethyl --.

Signed and Sealed this

Eighteenth Day of February, 2003

JAMES E. ROGAN
*Director of the United States Patent and Trademark Office*